US012648983B2

(12) United States Patent　　(10) Patent No.:　US 12,648,983 B2
Hill et al.　　　　　　　　　　　　(45) **Date of Patent:　*Jun. 9, 2026**

(54) COMPOSITION AND METHOD HAVING ENHANCED LSESr TO MAINTAIN AND PROMOTE HAIR HEALTH AND GROWTH

(71) Applicant: U.S. NUTRACEUTICALS, INC., Eustis, FL (US)

(72) Inventors: W. Stephen Hill, Ocala, FL (US); Umasudhan Palaniswamy, Sanford, FL (US); Margaret H. Dohnalek, Mount Dora, FL (US); Lawrence T. McCarty, Mount Dora, FL (US); Elizabeth J. Cartwright, Fruitland Park, FL (US)

(73) Assignee: U.S. NUTRACEUTICALS, INC., Eustis, FL (US)

( * ) Notice: Subject to any disclaimer, the term of this patent is extended or adjusted under 35 U.S.C. 154(b) by 812 days.

This patent is subject to a terminal disclaimer.

(21) Appl. No.: 17/818,013

(22) Filed: Aug. 8, 2022

(65) Prior Publication Data

US 2023/0068108 A1　　Mar. 2, 2023

Related U.S. Application Data

(60) Provisional application No. 63/234,308, filed on Aug. 18, 2021.

(51) Int. Cl.
| | |
|---|---|
| *A61K 36/889* | (2006.01) |
| *A61K 31/201* | (2006.01) |
| *A61K 31/506* | (2006.01) |
| *A61K 31/593* | (2006.01) |
| *A61K 33/30* | (2006.01) |
| *A61K 47/44* | (2017.01) |
| *A61P 17/14* | (2006.01) |

(52) U.S. Cl.
CPC .......... *A61K 36/889* (2013.01); *A61K 31/201* (2013.01); *A61K 31/506* (2013.01); *A61K 31/593* (2013.01); *A61K 33/30* (2013.01); *A61K 47/44* (2013.01); *A61P 17/14* (2018.01); *A61K 2236/37* (2013.01)

(58) Field of Classification Search
CPC .............. A61K 2236/37; A61K 31/201; A61K 31/506; A61K 31/593; A61K 33/30; A61K 36/889; A61K 47/44; A61K 9/0014; A61K 9/0053; A61K 2236/39; A61K 2300/00; A61K 2800/92; A61K 31/20; A61K 36/53; A61K 36/63; A61K 8/361; A61K 8/9794; A61K 9/1611; A61K 9/48; A61K 9/485; A61K 9/4866; A61K 9/4875; A61P 17/14; A61P 13/08; A23L 19/00; A23L 29/015; A23L 29/04; A23L 29/294; A23L 29/37; A23L 33/105; A23L 33/12; A23L 5/23; A61Q 5/00; A61Q 7/00
See application file for complete search history.

(56) References Cited

U.S. PATENT DOCUMENTS

| | | | |
|---|---|---|---|
| 5,284,873 A | 2/1994 | Salinero-Rodero et al. | |
| 6,039,950 A | 3/2000 | Khwaja et al. | |
| 6,319,524 B1 | 11/2001 | Gregg, Jr. | |
| 6,669,968 B2 | 12/2003 | Gregg, Jr. | |
| 8,067,470 B2 | 11/2011 | McDaniel | |
| 9,592,264 B2 | 3/2017 | Minatelli et al. | |
| 2011/0054043 A1 | 3/2011 | Funaki et al. | |
| 2021/0290638 A1 | 9/2021 | Prasad | |
| 2023/0054414 A1* | 2/2023 | Hill .......................... A23L 29/04 | |
| 2023/0060769 A1* | 3/2023 | Hill ........................ A61K 31/20 | |
| 2025/0177470 A1* | 6/2025 | Hill ........................ A61K 47/46 | |
| 2025/0177471 A1* | 6/2025 | Hill ...................... A61K 36/889 | |

FOREIGN PATENT DOCUMENTS

| | | | | |
|---|---|---|---|---|
| EP | 0309086 A1 | 3/1989 | | |
| FR | 2556968 A1 | 6/1985 | | |
| FR | 2643375 A1 | 8/1990 | | |
| FR | 2736828 | 1/1997 | | |
| WO | 97/03639 A2 | 2/1997 | | |
| WO | 98/33472 A1 | 8/1998 | | |
| WO | 9921009 | 4/1999 | | |
| WO | WO-03013561 A1 * | 2/2003 | .............. | A61P 17/00 |
| WO | 2014165561 | 10/2014 | | |

(Continued)

OTHER PUBLICATIONS

Marks et al.; "Effects of a saw palmetto herbal blend in men with symptomatic benign prostatic hyperplasia." J. Urol. 163 (2000); pp. 1451-1456. Published in May 2000.*
Catchpole et al.; J. Supercritical Fluids; vol. 22, Issue 2; pp. 129-138. Published Feb. 2002.*
Ortega et al.; J. Supercritical Fluids; vol. 120, Part 1; pp. 132-139. Published online Nov. 9, 2016.*
Abe et al., "Isolation and Pharmacological Characterization of Fatty Acids from Saw Palmetto Extract," Analytical Sciences; vol. 25; Apr. 2009; pp. 553-557.
Abe et al., "Pharmacologically Relevant Receptor Binding Characteristics and 5α-Reductase Inhibitory Activity of Free Fatty Acids Contained in Saw Palmetto Extract," Biol. Pharm. Bulletin; vol. 32, No. 4; Jan. 20, 2009; pp. 646-650.

(Continued)

*Primary Examiner* — Jeffrey T. Palenik
(74) *Attorney, Agent, or Firm* — ALLEN, DYER, DOPPELT + GILCHRIST, PA

(57) ABSTRACT

A composition is formulated in a therapeutic amount to maintain and promote hair health and growth in a human in need thereof. The composition may comprise a shelf stable, supercritical $CO_2$ fluid extracted, enhanced lipidosterolic extract of *Serenoa repens* (LSESr). The enhanced LSESr may have a ratio of free fatty acids to total fatty acids that is greater than about 80.0% and an enrichment of lauric, myristic, oleic and linoleic acids as free fatty acids to total free fatty acids that is greater than about 82.0%. An enrichment of linoleic and linolenic acids together may be greater than about 3.7%.

21 Claims, 47 Drawing Sheets

(56) References Cited

FOREIGN PATENT DOCUMENTS

WO       2022194860       9/2022

OTHER PUBLICATIONS

Cabeza et al., "Effect of ß-Sitosterol as Inhibitor of 5α-Reductase in Hamster Prostate," Proceedings of the Western Pharmacology Society; 46 (2003); pp. 153-155.

Chen et al., "Functional Complexity of Hair Follicle Stem Cell Niche and Therapeutic Targeting of Niche Dysfunction for Hair Regeneration," Journal of Biomedical Science; 27:43 (2020); pp. 1-11.

Di Pietro et al., "NMR Determination of Free Fatty Acids in Vegetable Oils, " Processes; 8, 410; Mar. 31, 2020; pp. 1-15.

Fu et al., "Novel Pathway of Metabolism of α-Linolenic Acid in the Guinea Pig," Pediatric Research; 47 (2000); pp. 414-417.

Liang et al., "Inhibition of Steroid 5x-Reductase by Specific Aliphatic Unsaturated Fatty Acids," Biochemical Journal; vol. 285 (1992); pp. 557-562.

Liu et al., "Anti-Androgenic Activity of Fatty Acids," Chemistry & Biodiversity; vol. 6 (2009); pp. 503-512.

Mistry et al., "Free Fatty-Acid Transport via CD36 Drives ß-Oxidation-Mediated Hematopoietic Stem Cell Response to Infection," Nature Communications; 12:7130 (2021); pp. 1-13.

Prager et al., "A Randomized, Double-Blind, Placebo-Controlled Trial to Determine the Effectiveness of Botanically Derived Inhibitors of 5-α-Reductase in the Treatment of Androgenetic Alopecia," The Journal of Alternative and Complementary Medicine; vol. 8, No. 2; (2002); pp. 143-152.

Raynaud et al., "Inhibition of Type 1 and Type 2 5α-Reductase Activity by Free Fatty Acids, Active Ingredients of Permixon," Journal of Steroid Biochemistry & Molecular Biology; 82; Aug. 2002; pp. 233-239.

Rossi et al., "Comparitive Effectiveness of Finasteride vs. Serenoa Repens in Male Androgenetic Alopecia: A Two-Year Study," International Journal of Immunopathology and Pharmacology; vol. 25, No. 4; Oct. 5, 2012; pp. 1167-1173.

Suzuki et al., "Pharmacological Effects of Saw Palmetto Extract in the Lower Urinary Tract," Acta Pharmacologica Sinica; 30(3); Mar. 2009; pp. 271-281.

Zhu et al., "Serenoa Repens Extracts Promote Hair Regeneration and Repair of Hair Loss Mouse Models by Activating TGF-β and Mitochondrial Signaling Pathway," European Review for Medical and Pharmacological Sciences; 22 (2018); pp. 4000-4008.

Sanchez et al., "5α-Reductase Isozymes and Aromatase MRNA Levels in Plucked Hair From Young Women With Female Pattern Hair Loss," Archives of Dermatological Research; Jan. 2018; 310(1):77-83; Abstract Only (1 page).

U.S. Appl. No. 17/818,010, filed Aug. 8, 2022 Inventors: W. Stephen Hill et al.

U.S. Appl. No. 17/818,011, filed Aug. 8, 2022 Inventors: W. Stephen Hill et al.

Bernichtein et al., "Anti-inflammatory properties of lipidosterolic extract of serenoa repens (permixon) in a mouse model of prostate hyperplasia: anti-inflammatory effects of permixon in prostate hyperplasia", The Prostate, vol. 75, No. 7, Feb. 2015, pp. 706-722.

Bartolome et al., "Supercritical fluid extraction from saw palmetto berries at a pressure range between 300bar and 450bar", The Journal of Supercritical Fluids, vol. 120, Nov. 2016, pp. 132-139.

Indena, "Sabalselect", https://www.ingredientsonline.com/media/wysiwyg/science/SabalSelectSerenoaBrochureRev.pdf, Jan. 2007, pp. 1-6.

Strum, *Serenoa repens* (saw palmetto) for lower urinary tract symptoms (LUTS): the evidence for efficacy and safety of lipidosterolic extracts. Part I, URO, vol. 1, No. 3, Jul. 2021, pp. 118-138.

De Monte et al., "Modern extraction techniques and their impact on the pharmacological profile of Serenoa repens extracts for the treatment of lower urinary tract symptoms", BMC Urology, 2014, pp. 1-11.

Morganti et al., "Effect of gelatin-cystine and serenoa repens extract on free radicals level and hair growth", J. Appl Cosmetol, 16, Jul. 9, 1998, pp. 57-64.

Wessagowit et al., "Treatment of male androgenetic alopecia with topical products containing serenoa repens extract", Australasian Journal of Dermatology, 2015, pp. 1-7.

Masoud et al., "Efficacy and safety of a novel herbal solution for the treatment of androgenetic alopecia and comparision with 5% minoxidil: A double-blind, randomized controlled trial study", Tabriz University of Medical Sciences, Tabriz, Iran, Nov. 2018-Sep. 2019, pp. 1-24.

Panahi et al., "Rosemary oiul vs minoxidil 2% for the treatment of androgenetic alopecia: A randomized comparative trial", Skin Med, Dermatology for the Clinician, vol. 13, issue 1, Jan. 2, 2015, pp. 15-21.

Dhariwala et al., "An overview of herbal alternative in androgenetic alopecia", Wiley Periodicals, Inc., Journal of Cosmetic Dermatology, Feb. 2019, pp. 1-10.

Premanand et al., "Androgen modulation of Wnt/β-catenin signaling in androgenetic alopecia", Archives of Dermatological Research, Jul. 2018, abstract only.

Daszczuk et al., "An intrinsic oscillation of gene networks inside hair follicle stem cells: an additional layer that can modulate hair stem cell activities", Frontiers in Cell and Developmental Biology, Dec. 2020, abstract only.

Csuka et al., "A systematic review on the lipid composition of human hair", International Journal of Dermatology, Feb. 2022, abstract onlly.

Coderch et al., "Exogenous and endogenous lipids of human hair", Skin Research & Technology, vol. 23, issue 4, Nov. 2017, pp. 1-2.

Piccini et al., "Intermediate hari follicles from patients with femal pattern hair loss are associated with nutrient Insufficiency and a quiescent metabolic phenotype" MDPI, Nutrients, Aug. 2022, pp. 1-19.

Scaglione et al., "Comparison of the potency of different brands of serenoa repens extract on 5alpha-reductase types I and II in prostatic co-culture epithelial and fibroblast cells", Pharmacology, 2008, abstract only.

Scaglione et al, "Comparison of the potency of 10 different brands of serenoa repens extracts", European Review for Medical and Pharmacological Sciences, May 2012, abstract only.

Fu et al., "Dihydrotestosterone-induced hair regrowth inhibition by activating androgen receptor in C57BL6 mice simulates androgenetic alopecia", Biomedicine & Pharmacotherapy, Elsevier, 2021, pp. 1-12.

Le Floc'H et al., "Effect of a nutritional supplement on hair loss in women", Journal of Cosmetic Dermatology, 2015, pp. 76-82.

Slominski et al. "Hair follicle pigmentation", The Society for Investigative Dermatology, Inc., 2004, pp. 13-21.

* cited by examiner

5αR Inhibition by Constituents of Saw Palmetto Extract (IC$_{50}$µg/ml)

| Compound | Total α-Reduced Steroids | | DHT |
|---|---|---|---|
| | 5αR-1 | 5αR-2 | Both |
| Free Fatty Acids | | | |
| Medium, Saturated Chains | | | |
| Capric acid (C$_{10}$) | - | 169.8 | - |
| Undecanoic acid (C$_{11}$) | - | 64.6 | - |
| Lauric acid (C$_{12}$) | 16.7 | 18.6-31.1 | 66.2-94.1 |
| Tridecanoic acid (C$_{13}$) | - | 28.5 | - |
| Myristic acid (C$_{14}$) | - | 4.3-146.5 | 56.4-114 |
| Long, Saturated Chains | | | |
| Pentadecanoic acid (C$_{15}$) | - | - | 145 |
| Palmitic acid (C$_{16}$) | >100 | >100 | 223 |
| Stearic acid (C$_{18}$) | >100 | >100 | >370 |
| Long, Unsaturated Chains | | | |
| Palmitoleic acid (C$_{16:1}$) | - | - | 27.5 |
| Oleic acid (C$_{18:1}$) | 4 | >100 | 36.2-54.5 |
| Linoleic acid (C$_{18:2}$) | 13 | 23.6-35 | 32.8-42.1 |
| Linolenic acid (C$_{18:3}$) | - | 27.3 | 2.8-33.4 |
| Octadecatetraenoic acid (C$_{18:4}$) | - | - | 15.8 |
| Arachidonic (C$_{20:4}$) | - | - | 19.8 |
| Esterified Fatty Acids | | | |
| 1-Monolaurin (C$_{12}$) | - | 171.5 | - |
| 2-Monolaurin (C$_{12}$) | - | 127.6 | - |
| Lauric acid ethyl ester (C$_{12}$) | >100 | >100 | - |
| Oleic acid ethyl ester (C$_{18:1}$) | >100 | >100 | - |
| Oxidized Fatty Acids | | | |
| cis-9(10)-Epoxystearic acid | - | 59.7 | - |
| Fatty alcohols | | | |
| Docosanol | >100 | >100 | - |
| Phytosterols | | | |
| Sitosterol | >100 | >100 | 1120 |
| Miscellaneous | | | |
| Tocopherol | >100 | >100 | - |

FIG. 2

5αR Inhibition by Fatty Acid Constituents Found in Saw Palmetto Extract

| | 5αR-1 | 5αR-2 | Both |
|---|---|---|---|
| Free Fatty Acids | | | |
| Medium, Saturated Chains | | | |
| Capric acid ($C_{10}$) | - | None | - |
| Undecanoic acid ($C_{11}$) | - | Moderate | - |
| Lauric acid ($C_{12}$) | Very active | Very active | Moderate |
| Tridecanoic acid ($C_{13}$) | - | Very active | - |
| Myristic acid ($C_{14}$) | - | Very active | Moderate |
| Long, Saturated Chains | | | |
| Pentadecanoic acid ($C_{15}$) | - | - | None |
| Palmitic acid ($C_{16}$) | None | None | None |
| Stearic acid ($C_{18}$) | None | None | None |
| Long, Unsaturated Chains | | | |
| Palmitoleic acid ($C_{16:1}$) | - | - | Very active |
| Oleic acid ($C_{18:1}$) | Very active | None | Very active |
| Linoleic acid ($C_{18:2}$) | Very active | Very active | Very active |
| Linolenic acid ($C_{18:3}$) | - | Very active | Very active |
| Octadecatetraenoic acid ($C_{18:4}$) | - | - | Very active |
| Arachidonic ($C_{20:4}$) | - | - | Very active |
| Esterified Fatty Acids | | | |
| 1-Monolaurin ($C_{12}$) | - | None | - |
| 2-Monolaurin ($C_{12}$) | - | None | - |
| Lauric acid ethyl ester ($C_{12}$) | None | None | - |
| Oleic acid ethyl ester ($C_{18:1}$) | None | None | - |
| Fatty alcohols | | | |
| Docosanol | None | None | - |

FIG. 3

Low Pressure CO₂ Extraction Experiment 1

| Lipid Profile Comparison | | | Exp. 2 | Exp. 3 | Exp. 4 | Exp. 5 | Exp. 6 |
|---|---|---|---|---|---|---|---|
| Product | Permxn 1 (5αR Exp.) | U4868 (Hops) | U4602 (5αR Exp) | Flomentum Soft Gel | USPlus IP | USPlus IP | USPlus IP |
| Lot # | G06743 | 160-001 | #170710 | C2101731 | #210908 | #211022 | #211105 |
| TOTAL FA % | 89.7 | 92.7 | 87.7 | 90.8 | 90.7 | 88.9 | 90.2 |
| Contribution of Fatty Acid as Free Fatty Acids | | | | | | | |
| Caproic | 0.7 | 1.4 | 0.8 | 1.7 | 1.2 | 0.9 | 0.9 |
| Caprylic | 1.6 | 2.0 | 1.4 | 1.9 | 1.8 | 1.5 | 1.4 |
| Capric | 2.2 | 2.4 | 1.7 | 2 | 2.2 | 1.9 | 1.8 |
| Lauric | 27.8 | 28.2 | 23.5 | 23.6 | 25.9 | 25.2 | 24.9 |
| Myristic | 10.5 | 10.9 | 9.2 | 9.5 | 10 | 9.7 | 9.8 |
| Palmitic | 7.6 | 8.1 | 6.6 | 7.3 | 7.6 | 6.6 | 6.7 |
| Stearic | 1.5 | 1.6 | 1.2 | 1.2 | 1.4 | 1.2 | 1.2 |
| Oleic | 23.9 | 27.7 | 20.8 | 25 | 24.6 | 21.4 | 22.0 |
| Linoleic | 3.1 | 3.9 | 3.1 | 2.9 | 3.6 | 3.3 | 3.1 |
| Linolenic | 0.7 | 0.6 | 0.7 | 0.8 | 0.7 | 0.6 | 0.6 |
| TOTAL FFA % | 79.9 | 87.0 | 69.1 | 75.8 | 79.0 | 72.4 | 72.6 |
| Total for the four highlighted FFA: | 65.3 | 70.7 | 56.6 | 61.0 | 64.1 | 59.6 | 59.8 |
| % total for these FFA: | 81.7% | 81.3% | 81.9% | 80.5% | 81.1% | 82.3% § | 82.4% § |
| Contribution % of Free Fatty Acids to Total Fatty Acids | | | | | | | |
| (%) | 89%* | 94% | 79%* | 83% | 87%¥ 87% | 81% | 80% |

Enhanced LSESr Inventive Pre-extraction Handling and CO₂ Extraction Processing

Secondary

*You can achieve the same percentage of free fatty acids to total fatty acids from proportionally lower total fatty acids or higher free fatty acids.
§Hopps process delivered more of these as free fatty acids
So, effectiveness of an extract is to achieve ca. 82% of the free fatty acids contributed by the 4 key biologically important fatty acids.

FIG. 4A

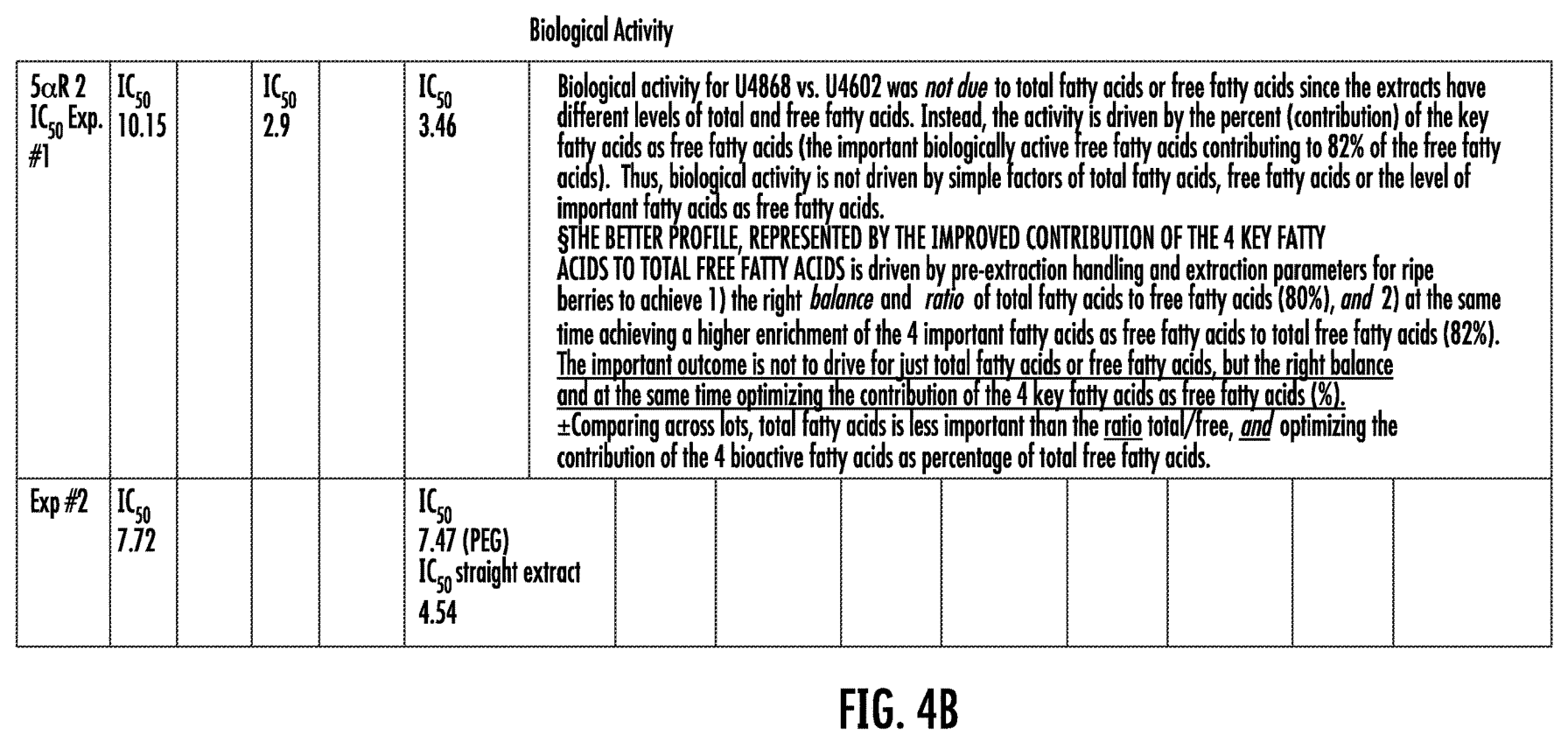

Biological Activity

| 5αR2 IC$_{50}$ Exp. #1 | IC$_{50}$ 10.15 | IC$_{50}$ 2.9 | IC$_{50}$ 3.46 | Biological activity for U4868 vs. U4602 was *not due* to total fatty acids or free fatty acids since the extracts have different levels of total and free fatty acids. Instead, the activity is driven by the percent (contribution) of the key fatty acids as free fatty acids (the important biologically active free fatty acids contributing to 82% of the free fatty acids). Thus, biological activity is not driven by simple factors of total fatty acids, free fatty acids or the level of important fatty acids as free fatty acids.<br><br>§THE BETTER PROFILE, REPRESENTED BY THE IMPROVED CONTRIBUTION OF THE 4 KEY FATTY ACIDS TO TOTAL FREE FATTY ACIDS is driven by pre-extraction handling and extraction parameters for ripe berries to achieve 1) the right *balance* and *ratio* of total fatty acids to free fatty acids (80%), *and* 2) at the same time achieving a higher enrichment of the 4 important fatty acids as free fatty acids to total free fatty acids (82%). The important outcome is not to drive for just total fatty acids or free fatty acids, but the right balance and at the same time optimizing the contribution of the 4 key fatty acids as free fatty acids (%).<br><br>±Comparing across lots, total fatty acids is less important than the ratio total/free, *and* optimizing the contribution of the 4 bioactive fatty acids as percentage of total free fatty acids. |
| Exp #2 | IC$_{50}$ 7.72 | | IC$_{50}$ 7.47 (PEG) IC$_{50}$ straight extract 4.54 | |

FIG. 4B

Reductase Inhibition Data

Valensa did 2 experiments to look at the ability of our LSESr, USPlus, to inhibit 5α-Reductase 2 vs. Permixon. Data were reported as the ability to inhibit enzyme activity ($IC_{50}$).

Experiment 1: Permixon compared to a supercritical extract product, either via conventional UHP-SCCO$_2$ (U4602-1) or slightly modified treatment of ripe dried saw palmetto berries and different extract site (U-4868-1)

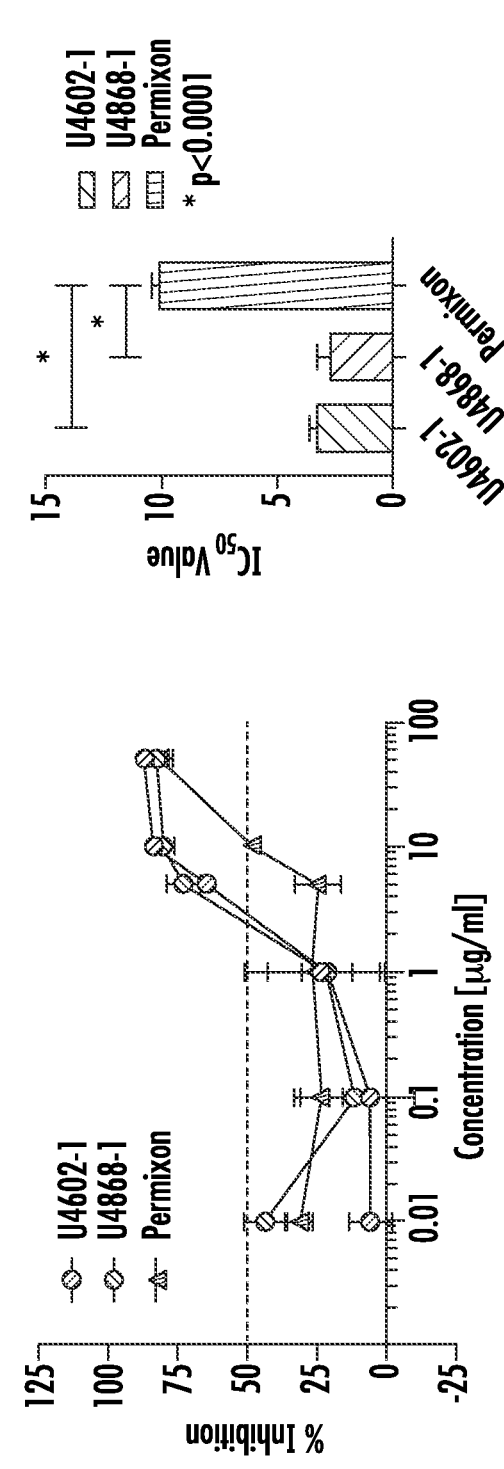

Experiment 1: Inhibition of 5α-Reductase 2

Variable U4602 - typical UHP-SCCO$_2$ extraction: $IC_{50}$ 3.46 µg/ml
Variable U4868 - modified SCCO$_2$ extraction: $IC_{50}$ 2.9 µg/ml
Permixon hexane extract (commercial product) on a pegylated matrix: $IC_{50}$ 10.15 µg/ml

FIG. 5

Experiment 2

In order to determine the possible impact of the Permixon product matrix on the invitro assay, a pegylated and conventional UHP-SCCO$_2$ product were compared to Permixon for the ability to inhibit the 5α-Reductase 2 enzyme.

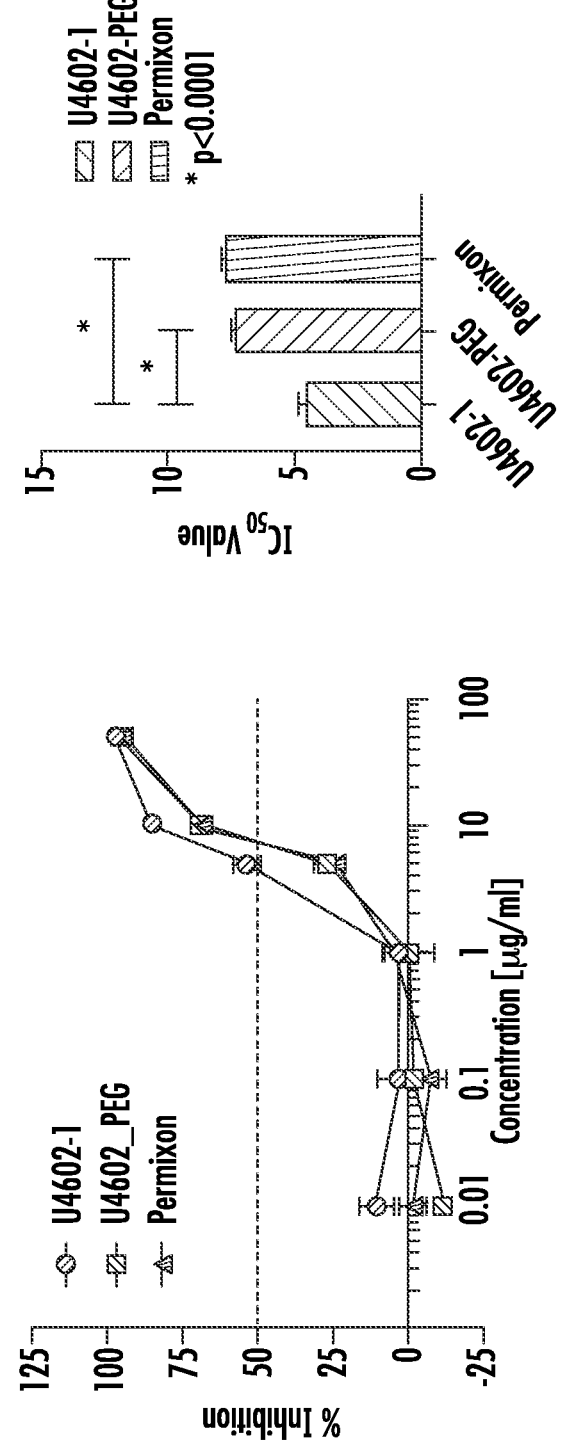

Experiment 2: Inhibition of 5α-Reductase 2

Variable U4602-1 (non-pegylated) produced via typical UHP-SCCO$_2$ extraction: IC$_{50}$ 4.54 μg/ml
Variable U4602-PEG produced via typical UHP-SCCO$_2$ extraction: IC$_{50}$ 7.47 μg/ml
Permixon hexane extract (commercial product) on a pegylated matrix: IC$_{50}$ 7.72 μg/ml

FIG. 6

Inhibition of 5a-Reductase 1
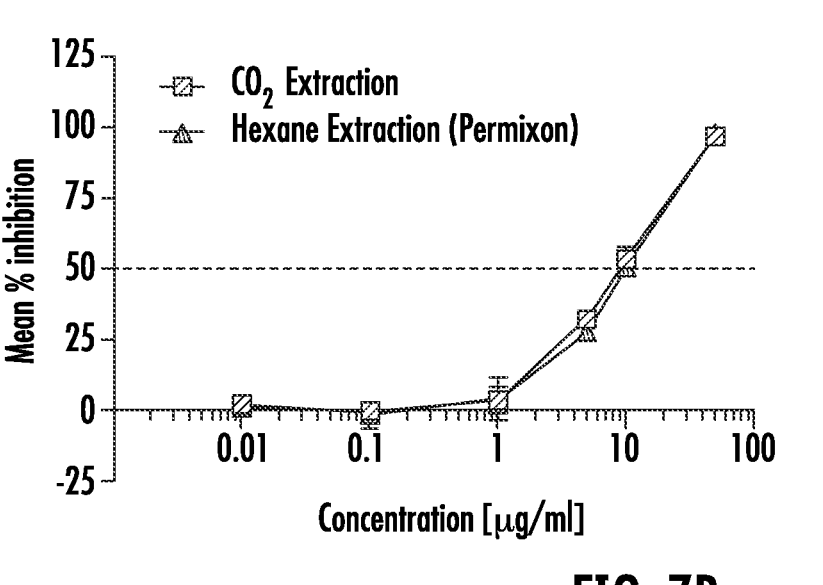
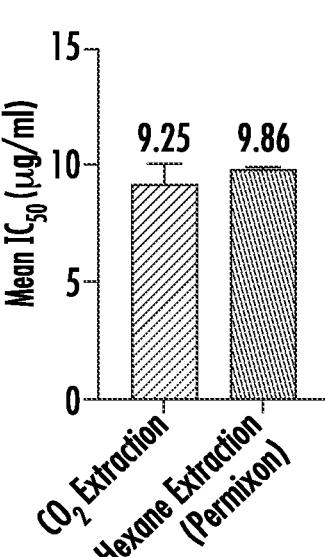
FIG. 7B

Cryogenic Mill amperage Saw Palmetto during production:

Aging impact on FFA with Fine Milled, at Central Florida Ambient warehouse conditions:

December into June

Warehouse Ambient conditions - Milled Saw Palmetto for Aging prior Extraction

*Central Florida*

Temp DegF

| Month | Mean | SEMean | StDev | CVariation | Median | TRMean | Minimum | Maximum | Range | N |
|---|---|---|---|---|---|---|---|---|---|---|
| 12 | 59.73 | 0.14 | 6.64 | 11.12 | 60.44 | 59.83 | 42.44 | 75.20 | 32.76 | 2,166 |
| 1 | 59.56 | 0.14 | 7.41 | 12.44 | 59.90 | 59.56 | 43.88 | 75.74 | 31.86 | 2,711 |
| 2 | 64.49 | 0.15 | 7.79 | 12.08 | 66.20 | 64.83 | 39.92 | 79.52 | 39.60 | 2,688 |
| 3 | 67.90 | 0.13 | 7.21 | 10.62 | 68.36 | 67.93 | 48.92 | 83.30 | 34.38 | 2,976 |
| 4 | 67.94 | 0.21 | 6.97 | 10.26 | 69.98 | 68.22 | 48.92 | 80.06 | 31.14 | 1,118 |
| 5 | 76.40 | 0.10 | 5.01 | 6.56 | 76.64 | 76.43 | 64.40 | 87.98 | 23.58 | 2,531 |
| 6 | 78.25 | 0.27 | 4.36 | 5.58 | 77.72 | 78.23 | 70.88 | 86.00 | 15.12 | 268 |

| Month | Mean | SEMean | StDev | CVariation | Median | TRMean | Minimum | Maximum | Range | N |
|-------|------|--------|-------|------------|--------|--------|---------|---------|-------|---|
| 12 | 77.44 | 0.30 | 13.91 | 17.96 | 81.00 | 78.38 | 36.90 | 96.60 | 59.70 | 2,166 |
| 1 | 75.77 | 0.23 | 12.14 | 16.02 | 77.20 | 76.24 | 44.10 | 95.90 | 51.80 | 2,711 |
| 2 | 77.62 | 0.28 | 14.47 | 18.65 | 80.50 | 78.46 | 31.20 | 97.50 | 66.30 | 2,688 |
| 3 | 74.36 | 0.22 | 12.09 | 16.26 | 77.00 | 74.92 | 33.60 | 93.90 | 60.30 | 2,976 |
| 4 | 67.67 | 0.50 | 16.56 | 24.47 | 71.60 | 68.08 | 34.30 | 92.80 | 58.50 | 1,118 |
| 5 | 67.25 | 0.24 | 12.04 | 17.91 | 68.90 | 67.69 | 30.40 | 91.20 | 60.80 | 2,531 |
| 6 | 70.45 | 0.66 | 10.80 | 15.33 | 73.05 | 71.03 | 42.50 | 86.00 | 43.50 | 268 |

FIG. 10B

For Lauric, Myristic, Oleic, Linoleic, Linolenic FFA & FA, Key Actives for Prostate Health Scatterplot of 5Actives FFA/FA vs Mill & Hold Time days

5 Key FA & FFA when starting berry moisture is Below Spec <10% Moisture

⬚⬚Average of 5Actives FA - 1     ⬚⬚Average of 5Actives FFA - 1     —⊙— Average of 5Actives FFA/FA - 1

Fig. 13: Scatterplot of 5Actives FFA/FA vs time between harvest & Extraction

Test for Equal Variances: 5Actives FFA/FA vs Brackets Hold Time
Multiple comparison intervals for the standard deviation, α = 0.05
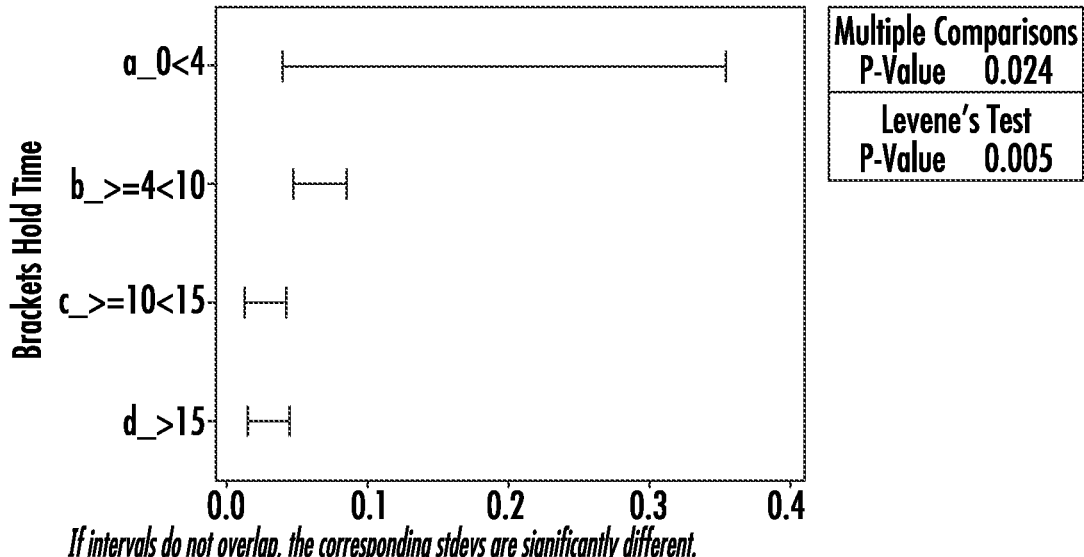
If intervals do not overlap, the corresponding stdevs are significantly different.
FIG. 15
ANOVA Lauric Acid % FFA/FA in Saw Palmetto per Mill & Hold
α = 0.05
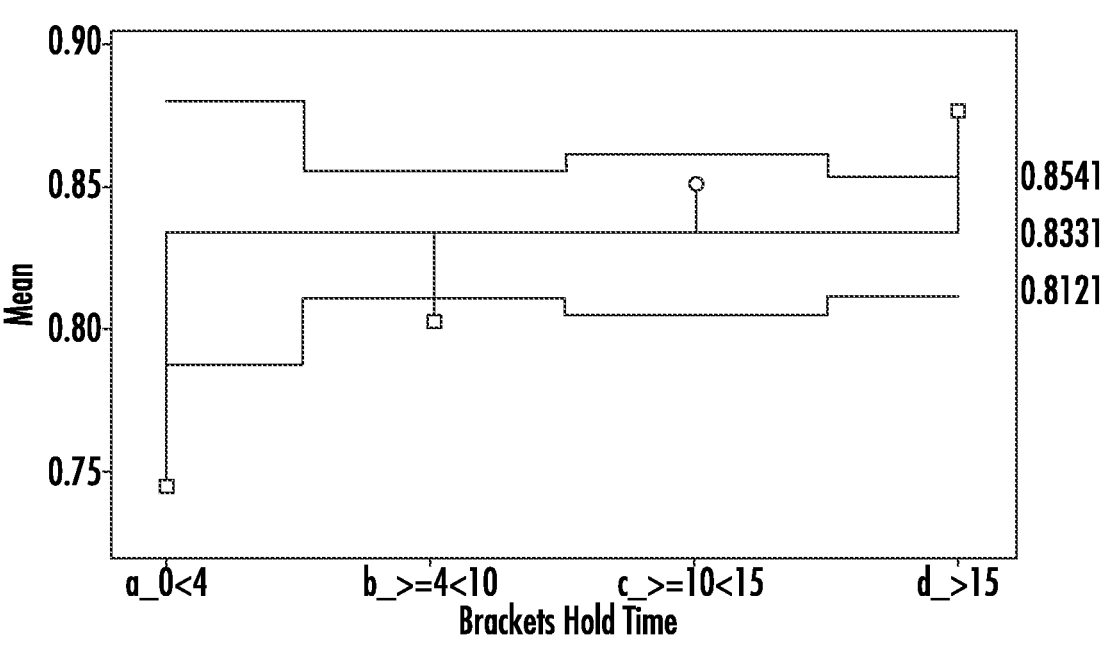
FIG. 16

ANOVA Myristic Acid % FFA/FA in Saw Palmetto per Mill & Hold
$\alpha = 0.05$ 0.8844
0.8660
0.8475

ANOVA Oleic Acid % FFA/FA in Saw Palmetto per Mill & Hold
$\alpha = 0.05$ 0.8510
0.8310
0.8110

%FFA/FA     5 Active Fatty Acids for Prostate Health
Post Mill Hold

| Time Days | Mean | SEMean | StDev | CVariation | Median | TRMean | Minimum | Maximum | Range | N |
|---|---|---|---|---|---|---|---|---|---|---|
| a_0<4 | 74.08% | 3.49% | 8.56% | 11.554 | 75.45% | | 59.75% | 84.88% | 25.13% | 6 |
| b_>=4<10 | 79.91% | 1.31% | 5.69% | 7.120 | 81.94% | 80.34% | 66.03% | 86.55% | 20.51% | 19 |
| c_>=10<15 | 84.77% | 0.54% | 2.02% | 2.379 | 85.11% | 84.79% | 81.62% | 87.77% | 6.15% | 14 |
| d_>15 | 87.42% | 0.49% | 2.24% | 2.563 | 87.80% | 87.63% | 80.65% | 90.30% | 9.65% | 21 |

FIG. 21

%FFA/FA Lauric Acid
Post Mill Hold

| Time Days | Mean | SEMean | StDev | CVariation | Median | TRMean | Minimum | Maximum | Range | N |
|---|---|---|---|---|---|---|---|---|---|---|
| a_0<4 | 74.60% | 3.36% | 8.23% | 11.027 | 75.82% | | 60.98% | 85.29% | 24.32% | 6 |
| b_>=4<10 | 80.05% | 1.44% | 6.26% | 7.819 | 81.64% | 80.77% | 60.87% | 86.87% | 26.00% | 19 |
| c_>=10<15 | 85.05% | 0.52% | 1.93% | 2.267 | 85.51% | 85.11% | 81.75% | 87.59% | 5.83% | 14 |
| d_>15 | 87.58% | 0.52% | 2.38% | 2.717 | 87.97% | 87.86% | 79.69% | 90.22% | 10.52% | 21 |

FIG. 22

%FFA/FA Myristic Acid
Post Mill Hold

| Time Days | Mean | SEMean | StDev | CVariation | Median | TRMean | Minimum | Maximum | Range | N |
|---|---|---|---|---|---|---|---|---|---|---|
| a_0<4 | 80.84% | 3.20% | 7.84% | 9.697 | 84.38% | | 68.18% | 88.50% | 20.31% | 6 |
| b_>=4<10 | 84.41% | 1.25% | 5.44% | 6.449 | 86.11% | 85.01% | 68.81% | 89.91% | 21.10% | 19 |
| c_>=10<15 | 87.91% | 0.36% | 1.36% | 1.551 | 88.18% | 87.94% | 85.45% | 90.00% | 4.55% | 14 |
| d_>15 | 89.34% | 0.40% | 1.82% | 2.034 | 89.19% | 89.47% | 83.65% | 92.59% | 8.94% | 21 |

FIG. 23

%FFA/FA Oleic Acid
Post Mill Hold

| Time Days | Mean | SEMean | StDev | CVariation | Median | TRMean | Minimum | Maximum | Range | N |
|---|---|---|---|---|---|---|---|---|---|---|
| a_0<4 | 73.72% | 3.63% | 8.90% | 12.066 | 75.18% | | 58.72% | 84.53% | 25.81% | 6 |
| b_>=4<10 | 80.03% | 1.25% | 5.43% | 6.787 | 81.41% | 80.36% | 67.95% | 86.51% | 18.55% | 19 |
| c_>=10<15 | 84.67% | 0.60% | 2.25% | 2.659 | 85.05% | 84.70% | 81.00% | 88.00% | 7.00% | 14 |
| d_>15 | 87.50% | 0.49% | 2.27% | 2.591 | 87.97% | 87.67% | 81.37% | 90.48% | 9.11% | 21 |

FIG. 24

%FFA/FA Linoleic Acid
Post Mill Hold

| Time Days | Mean | SEMean | StDev | CVariation | Median | TRMean | Minimum | Maximum | Range | N |
|---|---|---|---|---|---|---|---|---|---|---|
| a_0<4 | 55.41% | 5.62% | 13.77% | 24.860 | 55.65% | | 33.33% | 75.51% | 42.18% | 6 |
| b_>=4<10 | 67.50% | 1.76% | 7.65% | 11.339 | 69.09% | 68.04% | 49.15% | 76.60% | 27.44% | 19 |
| c_>=10<15 | 76.04% | 1.04% | 3.90% | 5.132 | 76.84% | 76.10% | 68.75% | 82.61% | 13.86% | 14 |
| d_>15 | 81.37% | 0.74% | 3.37% | 4.145 | 81.63% | 81.55% | 71.43% | 88.00% | 16.57% | 21 |

FIG. 25

%FFA/FA Linolenic Acid
Post Mill Hold

| Time Days | Mean | SEMean | StDev | CVariation | Median | TRMean | Minimum | Maximum | Range | N |
|---|---|---|---|---|---|---|---|---|---|---|
| a_0<4 | 78.17% | 4.11% | 10.06% | 12.865 | 80.36% | | 66.67% | 87.50% | 20.83% | 6 |
| b_>=4<10 | 80.48% | 2.00% | 8.71% | 10.826 | 83.33% | 80.15% | 66.67% | 100.00% | 33.33% | 19 |
| c_>=10<15 | 87.93% | 1.77% | 6.63% | 7.545 | 85.71% | 87.30% | 83.33% | 100.00% | 16.67% | 14 |
| d_>15 | 87.98% | 1.52% | 6.96% | 7.912 | 85.71% | 87.59% | 83.33% | 100.00% | 16.67% | 21 |

FIG. 26

*If intervals do not overlap, the corresponding stdevs are significantly different.*

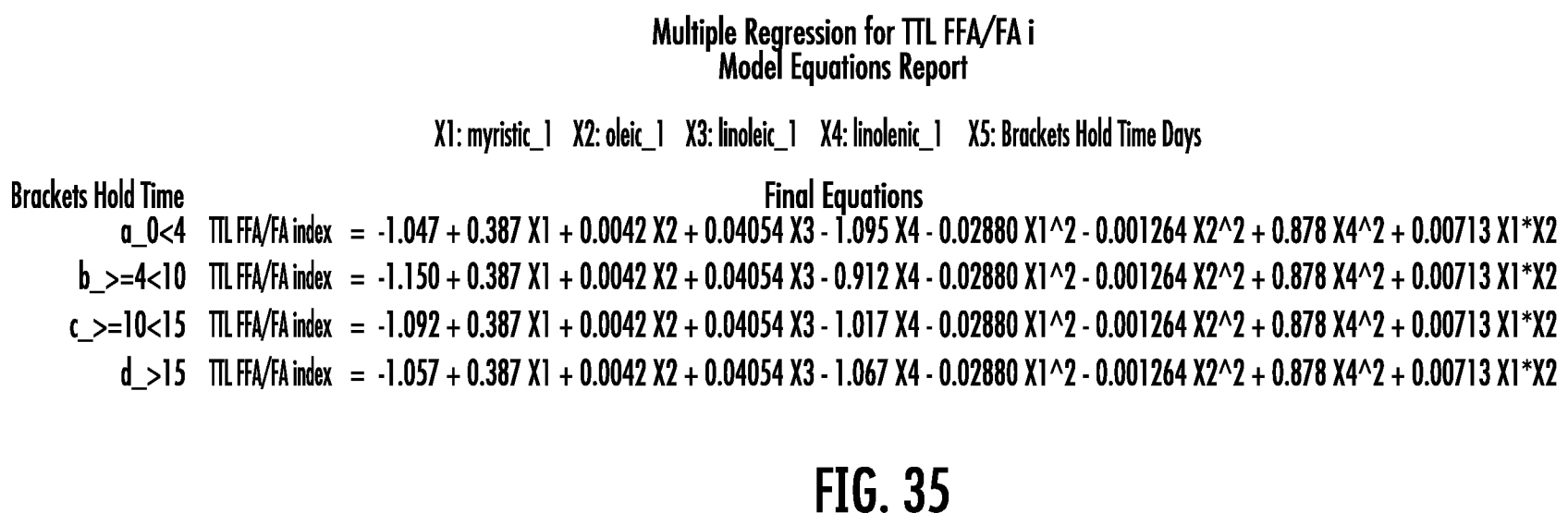

Multiple Regression for TTL FFA/FA i
Model Equations Report

X1: myristic_1   X2: oleic_1   X3: linoleic_1   X4: linolenic_1   X5: Brackets Hold Time Days Final Equations Brackets Hold Time a_0<4    TTL FFA/FA index   = -1.047 + 0.387 X1 + 0.0042 X2 + 0.04054 X3 - 1.095 X4 - 0.02880 X1^2 - 0.001264 X2^2 + 0.878 X4^2 + 0.00713 X1*X2 b_>=4<10    TTL FFA/FA index   = -1.150 + 0.387 X1 + 0.0042 X2 + 0.04054 X3 - 0.912 X4 - 0.02880 X1^2 - 0.001264 X2^2 + 0.878 X4^2 + 0.00713 X1*X2 c_>=10<15    TTL FFA/FA index   = -1.092 + 0.387 X1 + 0.0042 X2 + 0.04054 X3 - 1.017 X4 - 0.02880 X1^2 - 0.001264 X2^2 + 0.878 X4^2 + 0.00713 X1*X2 d_>15    TTL FFA/FA index   = -1.057 + 0.387 X1 + 0.0042 X2 + 0.04054 X3 - 1.067 X4 - 0.02880 X1^2 - 0.001264 X2^2 + 0.878 X4^2 + 0.00713 X1*X2

FIG. 35

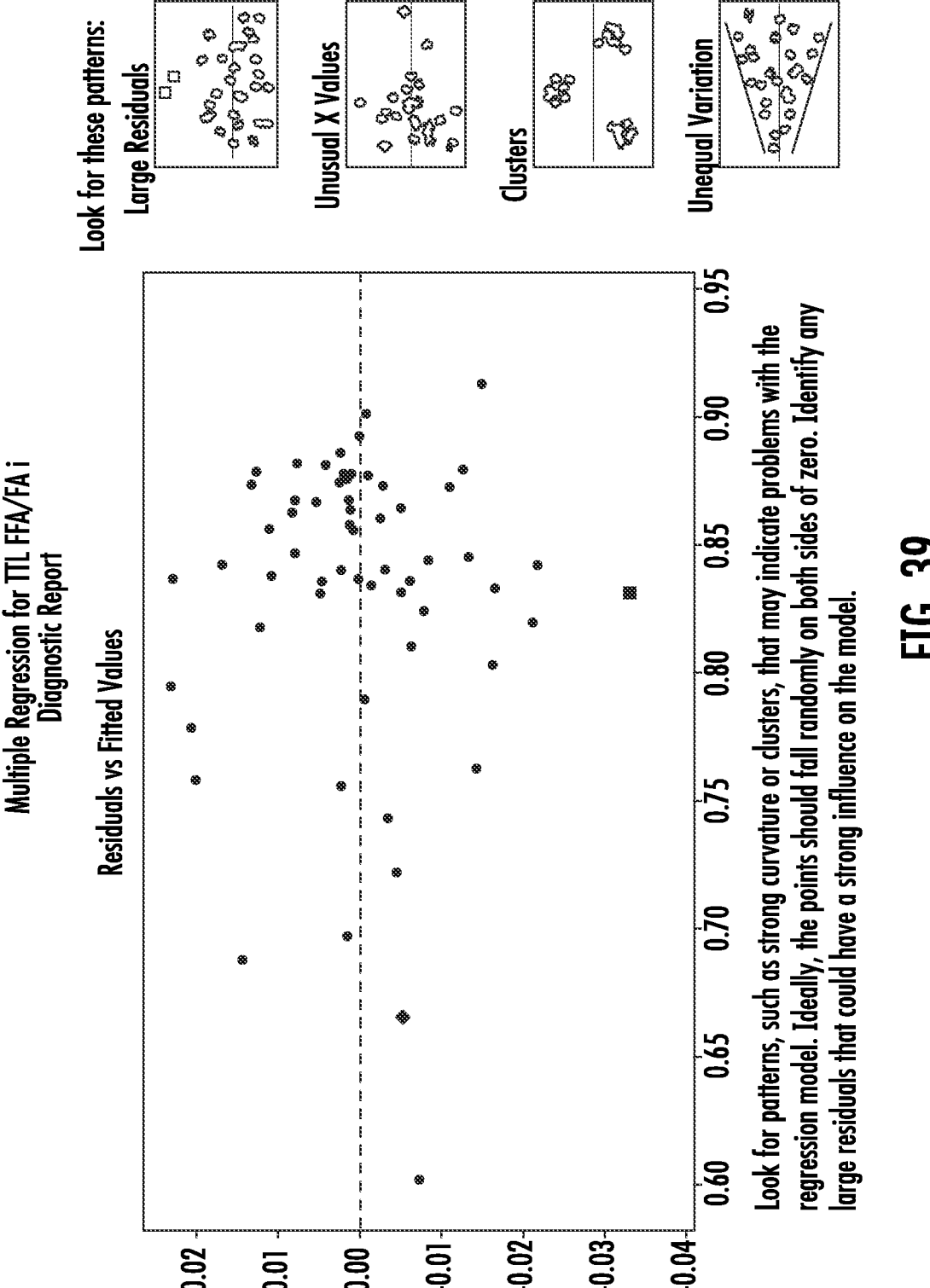

Multiple Regression for TTL FFA/FA i
Diagnostic Report

Residuals vs Fitted Values

Look for these patterns:

Large Residuals

Unusual X Values

Clusters

Unequal Variation

Look for patterns, such as strong curvature or clusters, that may indicate problems with the regression model. Ideally, the points should fall randomly on both sides of zero. Identify any large residuals that could have a strong influence on the model.

FIG. 39

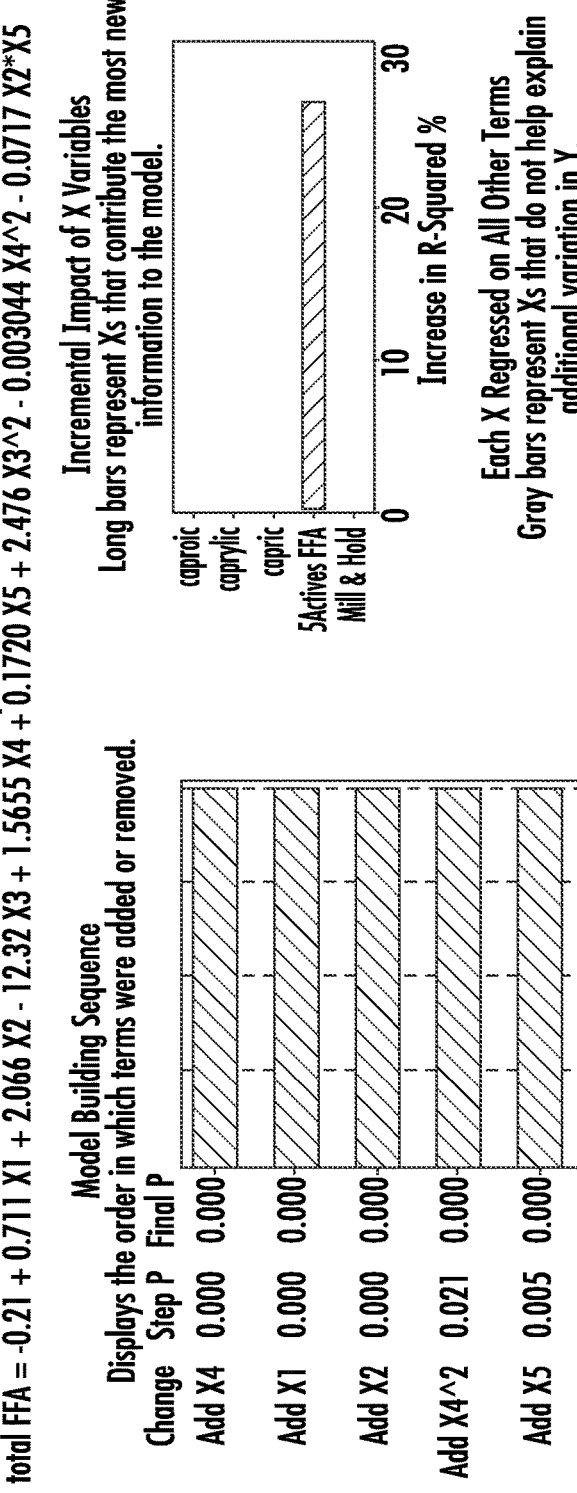

Multiple Regression for total FFA
Model Building Report

X1: caproic    X2: caprylic    X3: capric    X4: 5Actives FFA    X5: Mill & Hold Final Model Equation total FFA = -0.21 + 0.711 X1 + 2.066 X2 - 12.32 X3 + 1.5655 X4 + 0.1720 X5 + 2.476 X3^2 - 0.003044 X4^2 - 0.0717 X2*X5

Incremental Impact of X Variables
Long bars represent Xs that contribute the most new information to the model.

Each X Regressed on All Other Terms
Gray bars represent Xs that do not help explain additional variation in Y.

A gray bar represents an X variable not in the model.

Model Building Sequence
Displays the order in which terms were added or removed.

| Step | Change | Step P | Final P |
|------|--------|--------|---------|
| 1 | Add X4 | 0.000 | 0.000 |
| 2 | Add X1 | 0.000 | 0.000 |
| 3 | Add X2 | 0.000 | 0.000 |
| 4 | Add X4^2 | 0.021 | 0.000 |
| 5 | Add X5 | 0.005 | 0.000 |
|   | Add X2*X5 | 0.002 | 0.000 |
| 6 | Add X3 | 0.018 | 0.018 |
|   | Add X3^2 | 0.006 | 0.006 |

FIG. 40

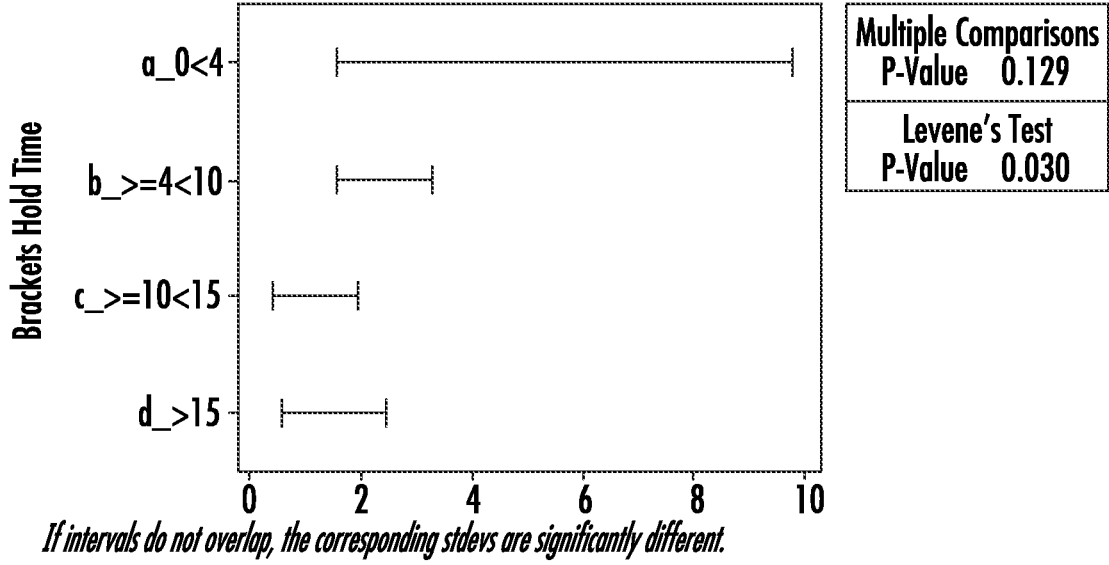
FIG. 51
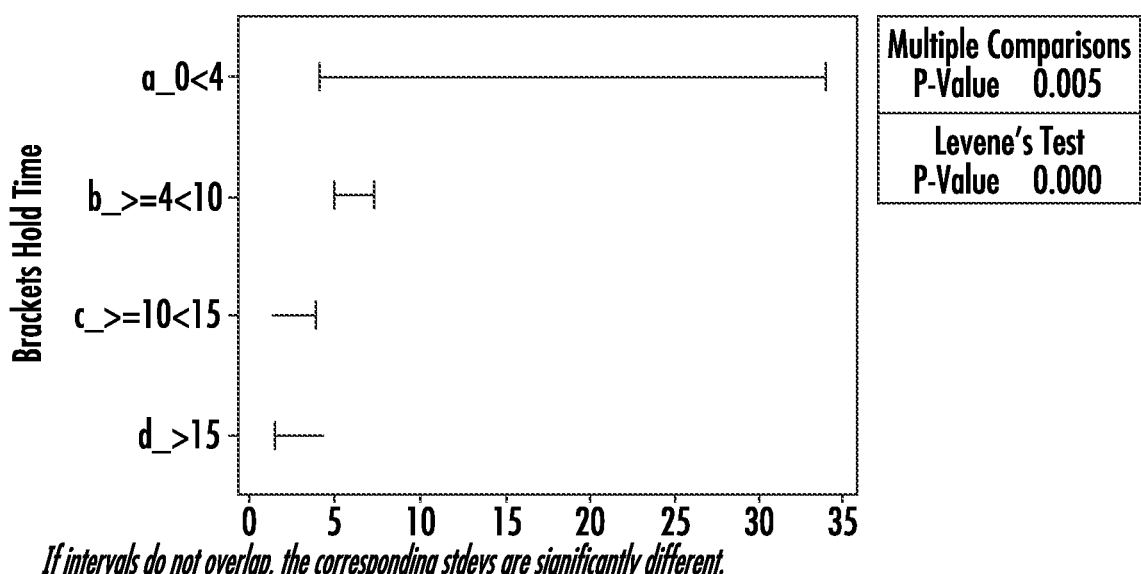
FIG. 52

ANOVA Free Fatty Acids per Mill & Hold
$\alpha = 0.05$
2019 & 2020 harvest Seasons Florida Test for Equal Variances: total FFA vs Brackets Hold Time
Multiple comparison intervals for the standard deviation, $\alpha = 0.05$ If intervals do not overlap, the corresponding stdevs are significantly different.

| Product Lot # | Low Pressure 200131 | High Pressure 300129 |
|---|---|---|
| Extraction Pressure | 250 bar | 500 bar |
| Extraction Temperature | 70 C | 85 C |
| TOTAL FA% | 90.1 | 89.7 |

Contribution of Fatty Acid as Free Fatty Acids

| | Low Pressure | High Pressure |
|---|---|---|
| Caproic | 1.6 | 1.4 |
| Caprylic | 1.9 | 1.7 |
| Capric | 2.1 | 2.0 |
| Lauric | 25.8 | 23.9 |
| Myristic | 10.3 | 9.7 |
| Palmitic | 7.4 | 7.0 |
| Stearic | 1.4 | 1.3 |
| Oleic | 25.2 | 23.9 |
| Linoleic | 3.4 | 3.1 |
| Linolenic | 0.6 | 0.6 |
| TOTAL FFA % | 80.0 | 74.8 |

Low Pressure: Total for the four highlighted FFA: 64.7% — % total for these FFA: 81%

High Pressure: Total for the four highlighted FFA: 60.6% — % total for these FFA: 81%

Contribution % of Free Fatty Acids to Total Fatty Acids

| | Low Pressure | High Pressure |
|---|---|---|
| FFA/TFA | 89% | 83% |

FIG. 56

COMPOSITION AND METHOD HAVING ENHANCED LSESr TO MAINTAIN AND PROMOTE HAIR HEALTH AND GROWTH

PRIORITY APPLICATION(S)

This application is based upon provisional application Ser. No. 63/234,308, filed Aug. 18, 2021, the disclosure which is hereby incorporated by reference in its entirety.

FIELD OF THE INVENTION

This invention relates to the field of nutritional supplements, and more particularly, to a composition comprising a lipidosterolic extract of *Serenoa repens* used to promote urinary and prostate function in men with enlarged prostates, or reduce androgenic hair loss in a patient, and a method for extracting the lipid components and enhancing the free fatty acids from the *Serenoa repens* berries for prostate, skin, and hair health.

BACKGROUND OF THE INVENTION

Saw palmetto (*Serenoa repens*) is a shrubby palm that grows in the southeastern United States and is prolific on pine flatwoods in peninsular Florida and southern Georgia. The saw palmetto grows a seed stalk (spadix) in late spring, which flowers and then develops a hard green fruit about the size of a small olive. The fruit ripens in the summer, turning shades of yellow, orange and black. The ripe fruit is harvested by hand during the late summer and early fall.

Saw palmetto fruit (berries) have been ingested by Native Americans for many centuries. Early in the 20th century, naturopathic physicians in the U.S. began prescribing a tea made from saw palmetto berries as a mild diuretic and for genitourinary problems. It became a popular male tonic, but eventually the therapeutic value of the tea (a water extract) came into question, and in the early 1940's it lost both its popularity and its inclusion in the National Formulary. Research in Europe in the 1960's led to the identification of the beneficial aspects of the lipid portion of the berry and its medically active components, including free fatty acids and sterols.

Saw palmetto was listed in the U.S. Pharmacopeia from 1900 to 1916, and the National Formulary from 1925 to 1942. At various times from 1938 to 1990, Food and Drug Acts and Amendments were passed to address the problems of drug safety and effectiveness. Beginning in 1972, the FDA began evaluating over-the-counter drugs, including herbal preparations. In the U.S., however, it is permissible to sell herbal products only if no claims or statements regarding their value in the prevention or treatment of disease are made.

Saw palmetto berries are a common source for many modern nutraceutical formulations. When the saw palmetto berries are initially harvested, they are usually placed into standard citrus boxes, which are then loaded onto flatbed trailers, and transported by truck to drying facilities. The ripe berries contain approximately 66% water and are dried for several days at about 130-140° F., and after drying, may be stored for several years without deteriorating.

Dried berries are generally bagged and shipped to processing facilities where they are ground into a powder. A therapeutically effective dose can be prepared from a lipidosterolic extract of the dried berries. In Europe, ethanol or hexane solvents are commonly used to isolate the lipidosterolic extract from the berries, leaving a residue of the harsh organic chemicals remaining in the extract. These lipidosterolic extracts, such as the hexanoic extracts, include fatty acids as various esters and free fatty acids, sterols and long-chain (fatty) alcohols. The fatty acids include caproic, caprylic, capric, lauric, myristic, palmitic, palmitoleic, stearic, oleic, linoleic and linolenic acid. Sterols include beta-sitosterol, campesterol, stigmasterol and stigmastanol. Long-chain alcohols include octacosanol, hexacosanol, triacontanol and tetracosanol. Usually, this extract is formulated into a convenient oral dosage form within a gelatin capsule.

Other techniques include the supercritical $CO_2$ extraction of saw palmetto conducted at about 45° C. at about 220 bar to produce an extract SABALSELECT® that may be used without further purification, and includes fatty acids, alcohols and sterols. These saw palmetto extracts vary widely in their final composition with free fatty acids ranging in concentration from about 40% to below about 80%, methyl and ethyl esters ranging from about 1.5% to 16.7%, and glycerides ranging from about 6.8% to about 52.2%.

The fact that the concentration of various fatty acids, esters, and glycerides can vary in a saw palmetto extract makes it challenging to determine the effectiveness of any single saw palmetto extract, thus requiring a biological assay of each manufactured lot produced as a saw palmetto extract. To maintain continuous biological assays of each manufactured lot of saw palmetto extract to determine the impact on efficacy from changes in components, such as individual free fatty acids and ratios of free fatty acids to total fatty acids is complex, inefficient and expensive. Better control over pre-extraction growth, harvesting and processing together with controlled extraction would be advantageous that can be used to obtain a consistent, effective standardized lipid profile.

Lipidosterolic extracts of *Serena repens* (LSESr), may be sold alone, generally in 320 mg softgels, or in a variety of herbal formulations to support urinary and prostate health in men with prostate enlargement. In some instances, saw palmetto extracts have also been used for reducing androgenic hair loss in a patient. Certain saw palmetto extracts, such as Permixon®, are regulated as a prescription drug in France and Germany, and are used by many patients for treatment of benign prostatic hyperplasia (BPH), or enlarged prostate, but has drawbacks as a hexane extract containing residual solvent.

In the United States, however, lipidosterolic extracts of *Serenoa repens* dried fruit are considered dietary supplements which may also provide some health benefits, including benefits associated with promoting urinary and prostate function, improve urinary flow and control, or address hair loss in a patient, including Androgenic Alopecia (AGA), or to promote healthy hair growth. The currently available saw palmetto products, such as Permixon®, are usually lipid extracts removed as the whole lipid composition of the saw palmetto berry. Traditionally, extraction processes have not allowed for the formulation of a saw palmetto extract that include a desired blend of the various lipid fractions, and therefore, it was challenging to custom formulate a LSESr composition to meet customer specifications and have optimal therapeutic value. Although some $CO_2$ extraction processes have yielded beneficial saw palmetto extracts, further control to enhance the percentages and ratios of compositional compounds, including different free fatty acids with a reduction in esters and glycerides, and an extended shelf life and low peroxide value without added antioxidants and stabilizers, would be beneficial for specific applications, such as prostate function, hair growth and health, skin care, such as acne remedies, and other applications.

SUMMARY OF THE INVENTION

In general, a composition may be formulated in a therapeutic amount to maintain and promote hair health and growth in a human in need thereof. The composition may comprise a shelf stable, supercritical $CO_2$ fluid extracted, enhanced lipidosterolic extract of *Serenoa repens* (LSESr). The enhanced LSESr may have a ratio of free fatty acids to total fatty acids that is greater than about 80.0% and an enrichment of lauric, myristic, oleic and linoleic acids as free fatty acids to total free fatty acids that is greater than about 82.0%. An enrichment of linoleic and linolenic acids together may be greater than about 3.7%.

The composition may be formulated as a topical lotion to be applied to the hair. The composition may include any one or more of zinc, vitamin D, rosemary oil and olive oil. The composition may include up to about 5.0% of Minoxidil.

In another example, the enhanced LSESr may have a balance of about 90.0% of total fatty acids to about 72.0% of free fatty acids. The enhanced LSESr may have an enrichment of lauric, myristic, oleic and linoleic free fatty acids to total free fatty acids of about 82.0% to about 84.0%. The enhanced LSESr may have a ratio of free fatty acids to total fatty acids of about 80.0% to about 82.0%. The enhanced LSESr may have a peroxide value that is less than about 3 meg/kg and a shelf stability of at least about 4 years without added antioxidants and stabilizers. The composition may be formulated into an oral dosage form and in a capsule of about 160 mg b.i.d. to about 320 mg, or about minimum 200 mg per dose of enhanced LSESr. The composition may include less than about 0.2 percent w/w of saw palmetto sterols.

A method to maintain and promote hair health and growth in a human includes administering to the human in need thereof a therapeutic amount of a composition that may comprise a shelf stable, supercritical $CO_2$ fluid extracted, enhanced lipidosterolic extract of *Serenoa repens* (LSESr). The enhanced LSESr may have a ratio of free fatty acids to total fatty acids that is greater than about 80.0% and an enrichment of lauric, myristic, oleic and linoleic acids as free fatty acids to total free fatty acids that is greater than about 82.0%. An enrichment of linoleic and linolenic acids together may be greater than about 3.7%.

DESCRIPTION OF THE DRAWINGS

Other objects, features and advantages of the present invention will become apparent from the detailed description of the invention, which follows when considered in light of the accompanying drawings in which:

FIG. 2 is a table showing the 5α-Reductase Type 1 and Type 2 isoenzyme $IC_{50}$ μg/ml inhibition by the free fatty acids found in a saw palmetto extract.

FIG. 3 is another table showing the relative 5α-Reductase Type 1 and Type 2 isoenzyme $IC_{50}$ μg/ml inhibition levels by the individual molecules found in the saw palmetto extract as shown in FIG. 2.

FIG. 4A is a lipid profile comparison among different samples (lots) of experimental LSESr compared to commercially available Permixon® and showing how pre-extraction processing parameters and supercritical $CO_2$ extraction parameters result in the more customized ratio of free fatty acids to total fatty acids such as Extraction Experiment Nos.

5 and 6 as Lot Nos. 211022 and 211105 as examples of the enhanced LSESr of the invention.

FIG. 4B is a table summarizing biological activity for specific samples identified in FIG. 4A and identifying the better profile of Experiment Nos. 5 and 6 as examples of the enhanced LSESr of the invention.

FIG. 5 shows a graph and bar chart for Inhibition Experiment 1 showing the inhibition of 5α-Reductase 2 for two experimental extracts when compared with commercially available Permixon® that contains polyethylene glycol (PEG) in the formulation. The two experimental samples of LSESr produced from supercritical $CO_2$ extractions (U4602) and (U4868) contain pure extract and no PEG in Extraction Experiments 1 and 2.

FIG. 6 is a graph for Inhibition Experiment 2 showing the inhibition of 5α-Reductase Type 2 using the PEG-containing (pegylated) commercially available product Permixon® compared to two samples of extraction experiments as LSESr, e.g., one that is the pure extract (U4602-1; normal) and the other pegylated (U4602-PEG).

Figure 7A:
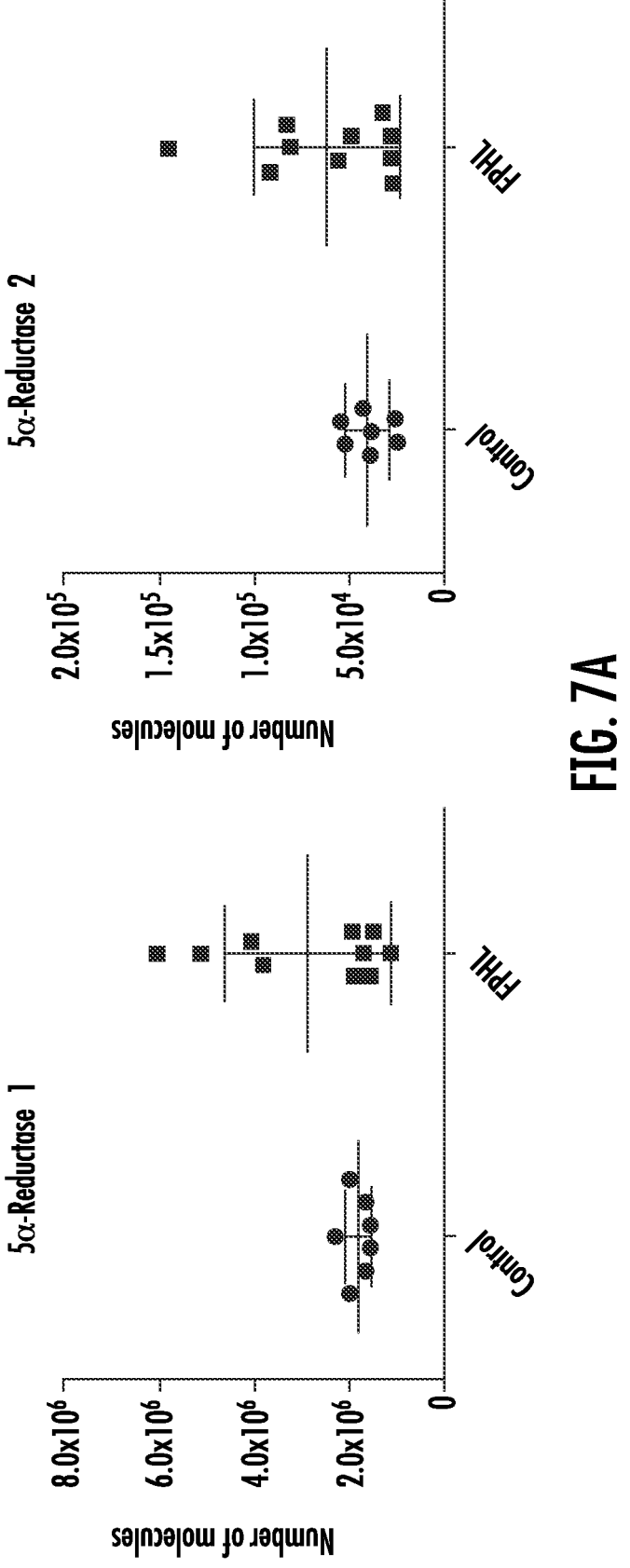

FIG. 7A are graphs showing that 5α-Reductase Type 1 enzymes are present in higher levels in the scalps of women with female pattern hair loss (FPHL), also known as androgenic alopecia (AGA), versus women with normal scalps as shown in the left-hand graph. 5α-Reductase Type 2 enzymes are also overexpressed in women with FPHL as shown in the right-hand graph.

FIG. 7B is a graph and bar chart showing the inhibition of 5α-Reductase Type 1 when compared with a sample from the supercritical $CO_2$ LSESr such as from Extraction Experiments 5 and 6 and commercially available Permixon®.

Figure 7C:
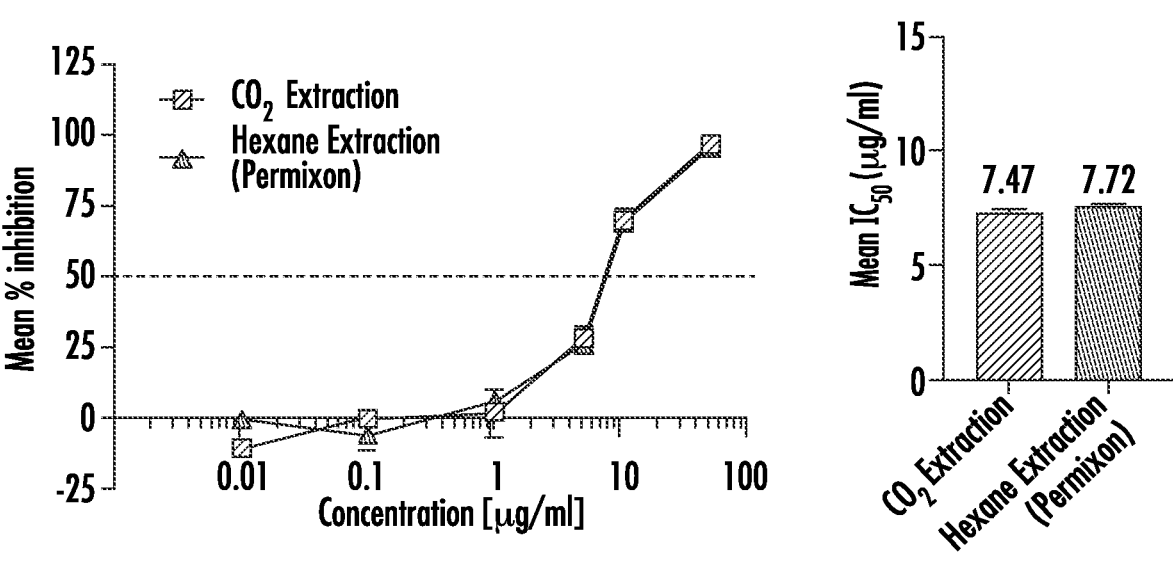

FIG. 7C is a graph and bar chart showing the inhibition of 5α-Reductase Type 2 enzyme when compared with a sample from the supercritical $CO_2$ LSESr such as from Extraction Experiments 5 and 6 and commercially available Permixon®.

Figure 7D:
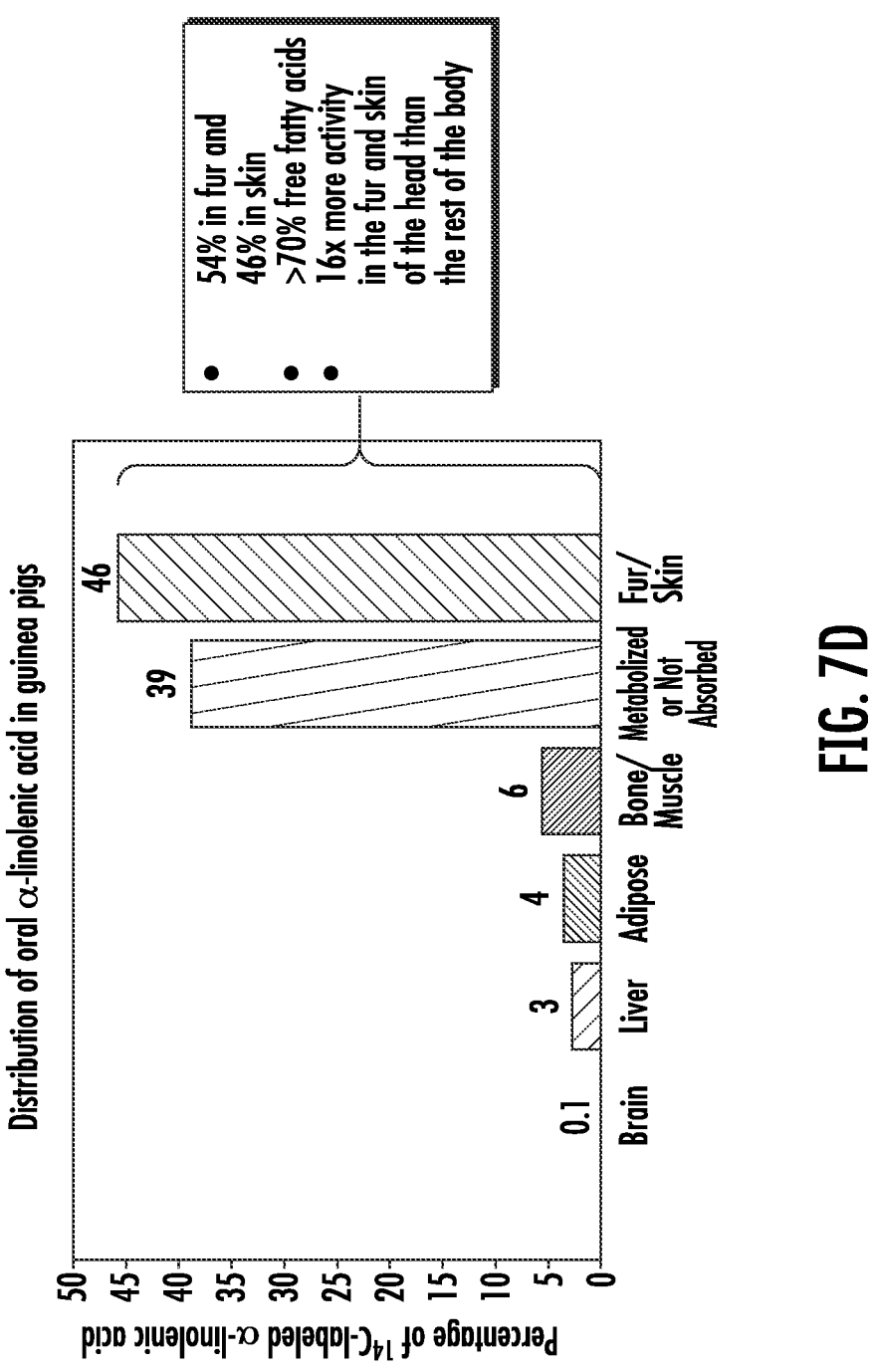

FIG. 7D is a bar chart showing the distribution of oral linolenic acid in guinea pigs and indicating how linolenic acid that may be enhanced such as in the enhanced LSESr of the current invention and is important for hair health and growth.

Figure 8:
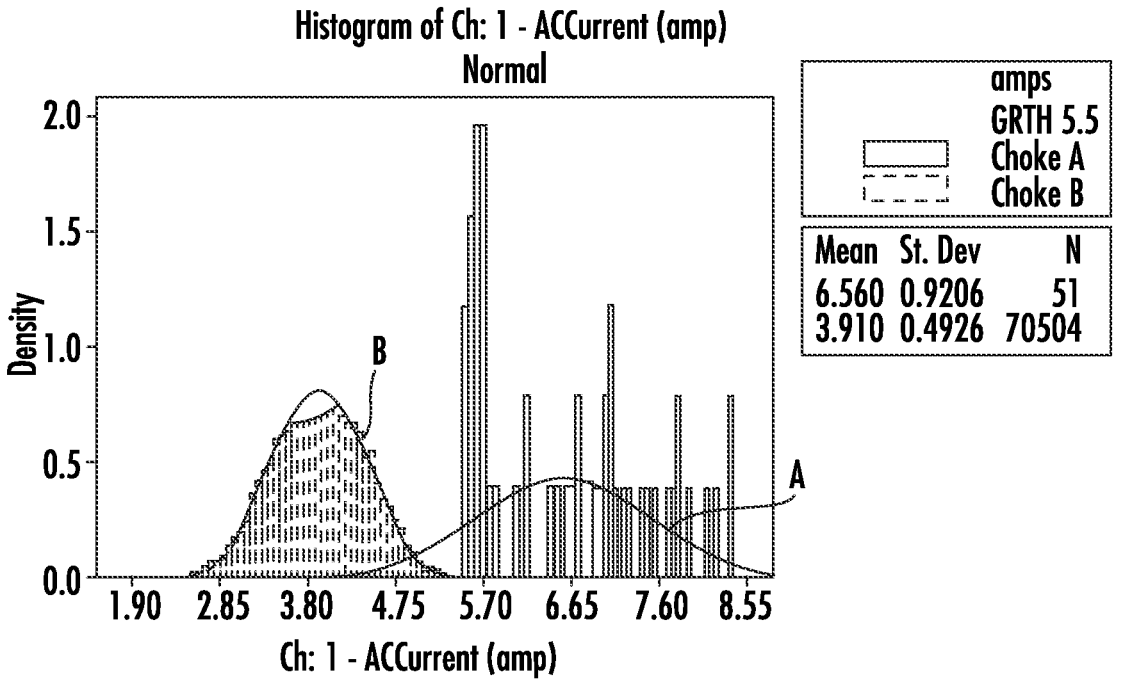

FIG. 8 are graphs showing a histogram of the cryogenic mill amperage in an example of the saw palmetto berry processing for producing the enhanced LSESr.

Figure 9A:
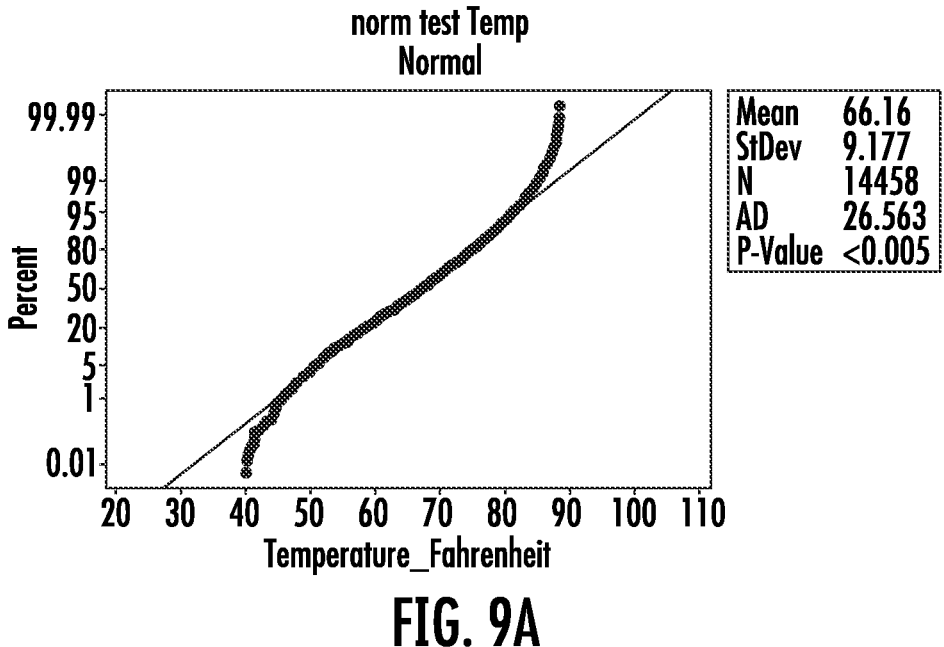
Figure 9B:
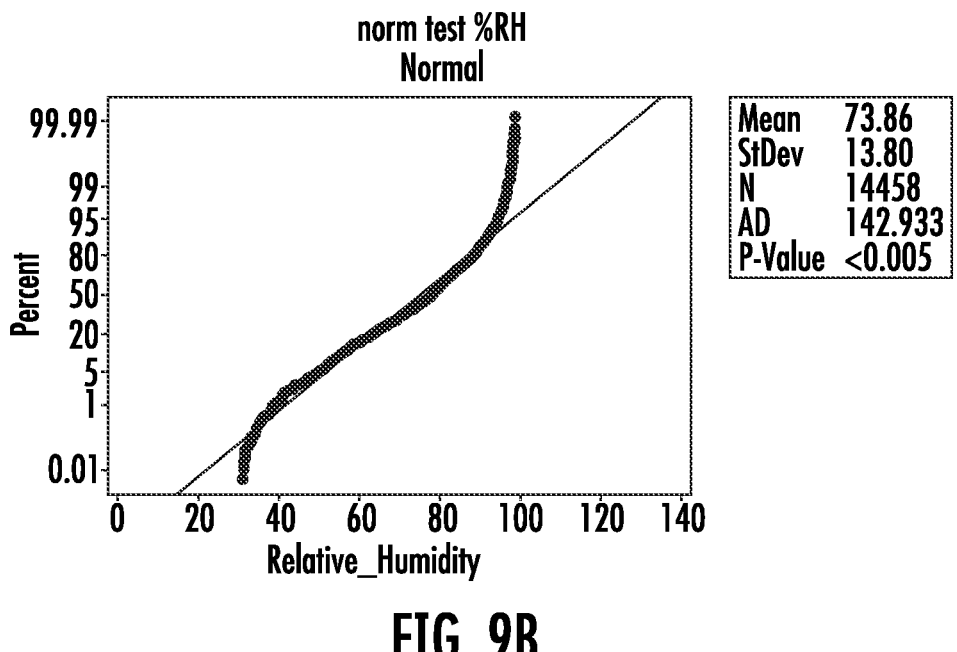

FIGS. 9A and 9B are graphs showing the normative test temperature in degrees Fahrenheit and test percent for relative humidity and showing the aging impact on free fatty acids.

FIGS. 10A and 10B are charts corresponding to the graph and charts of FIGS. 9A and 9B showing the temperature in degrees Fahrenheit and percentage for relative humidity.

Figure 11:
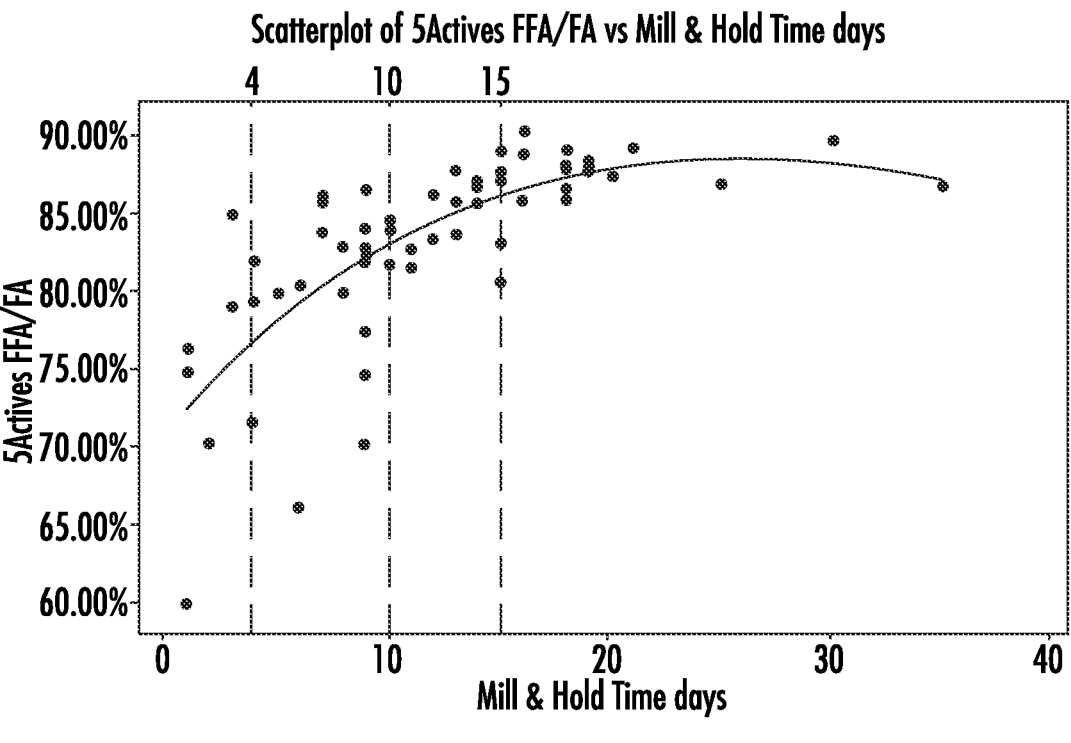

FIG. 11 is a graph showing the scatter plot of the five active free fatty acids as lauric, myristic, oleic, linoleic, and linolenic and the ratio of free fatty acids to fatty acids relative to the mill and hold time in days and showing how about 23 days gave the best ratio.

Figure 12A:
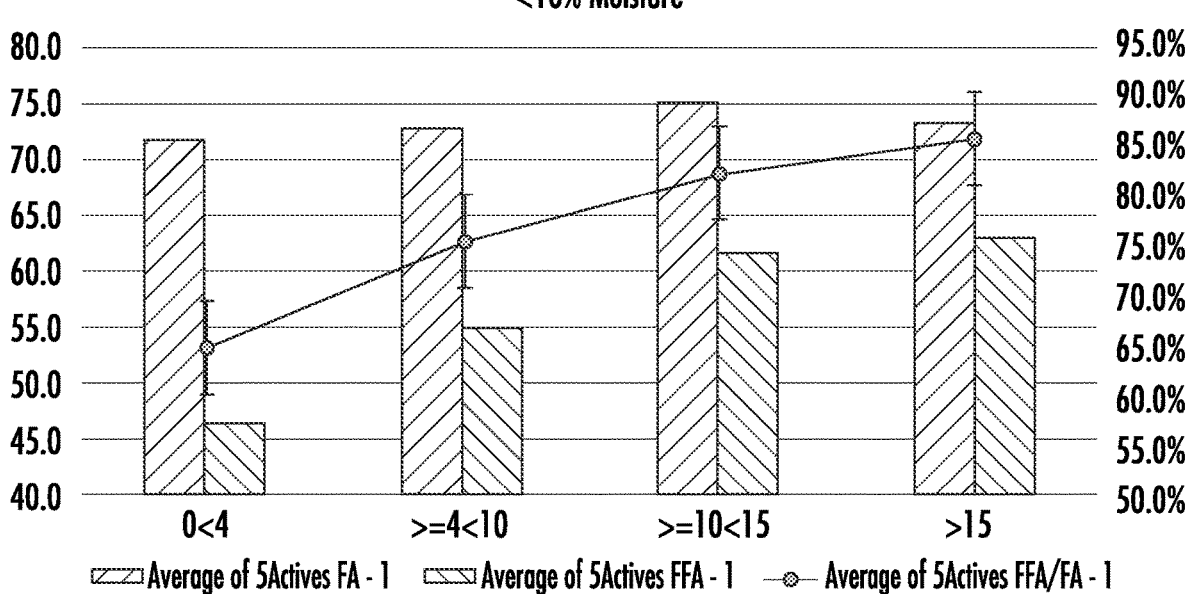
Figure 12B:
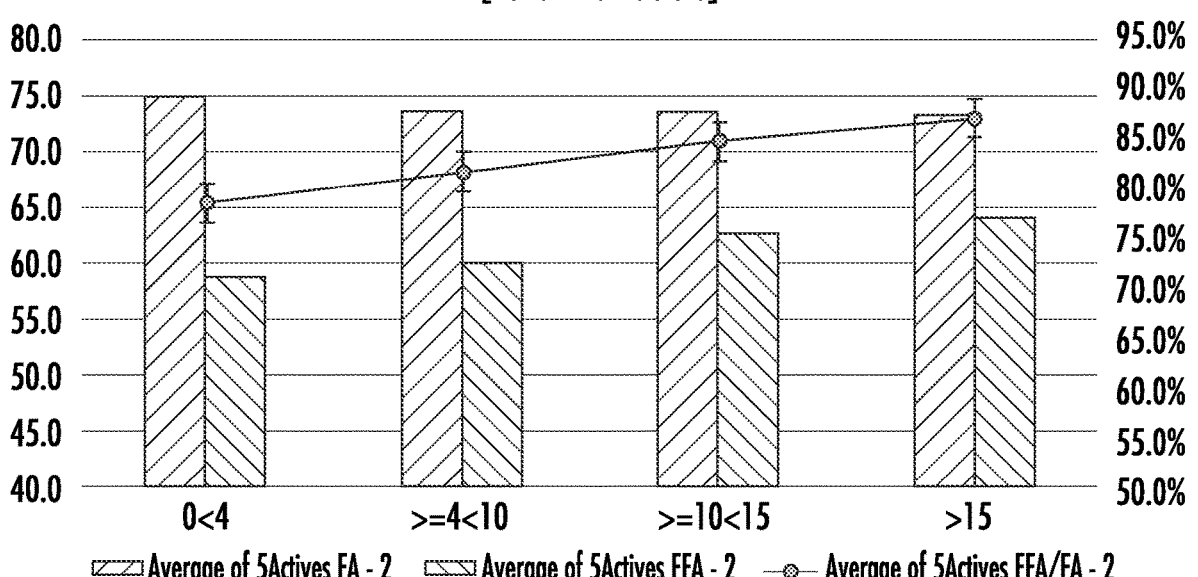

FIGS. 12A and 12B are bar charts showing the effect of processing with less than 10% moisture as below specifications (FIG. 12A) and at specifications of about 10% to 12% moisture (FIG. 12B), and showing the average of the five active free fatty acids, and the ratio of free fatty acids to fatty acids.

Figure 13:
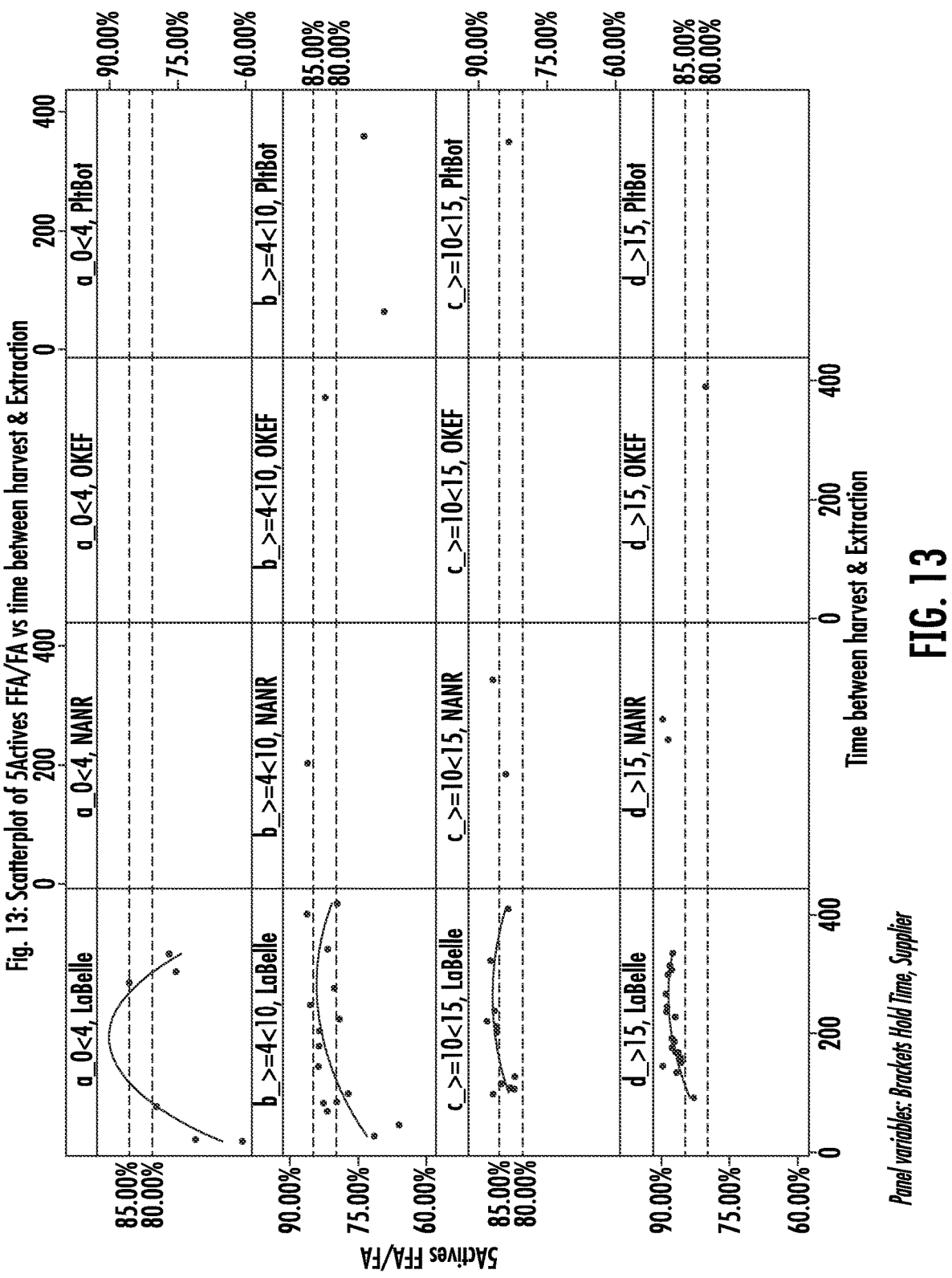

FIG. 13 is a graph showing a scatter plot of the five active free fatty acids/fatty acids versus time between harvest and extraction.

Figure 14:
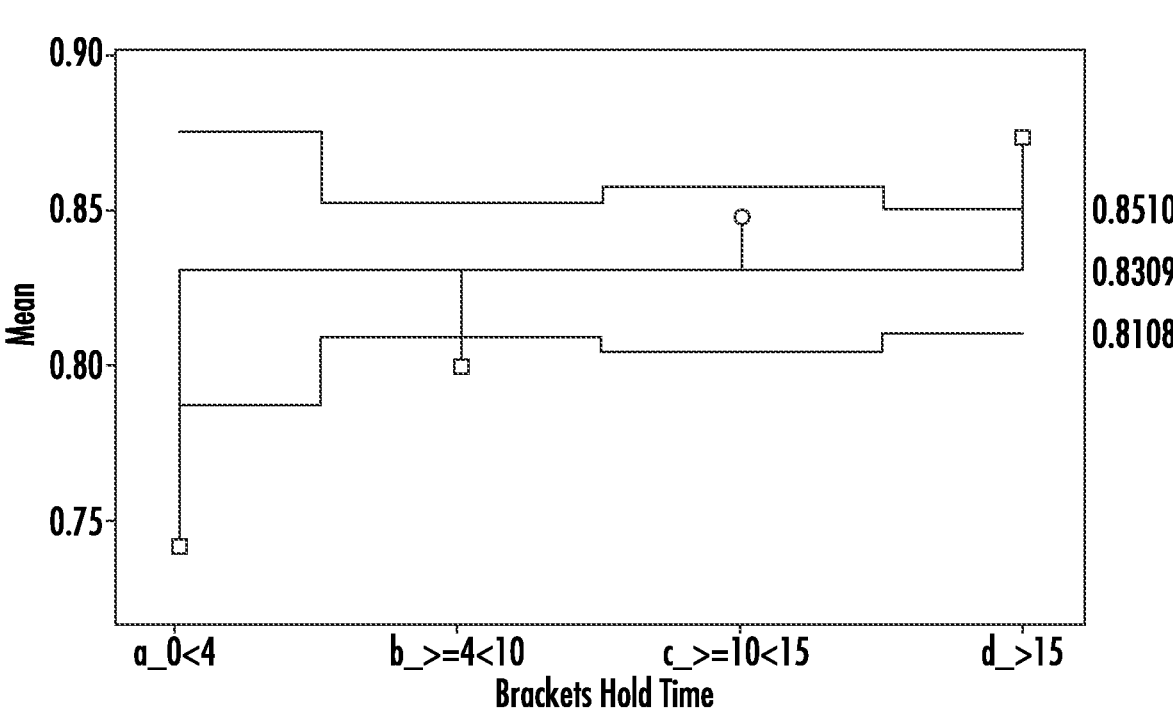
Figure 17:
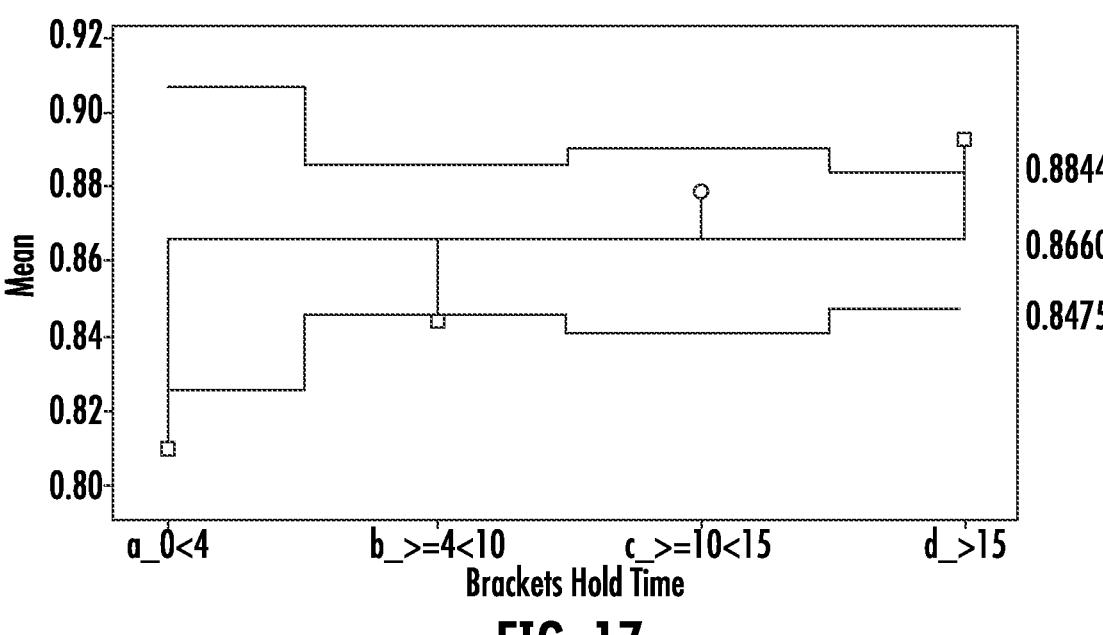
Figure 18:
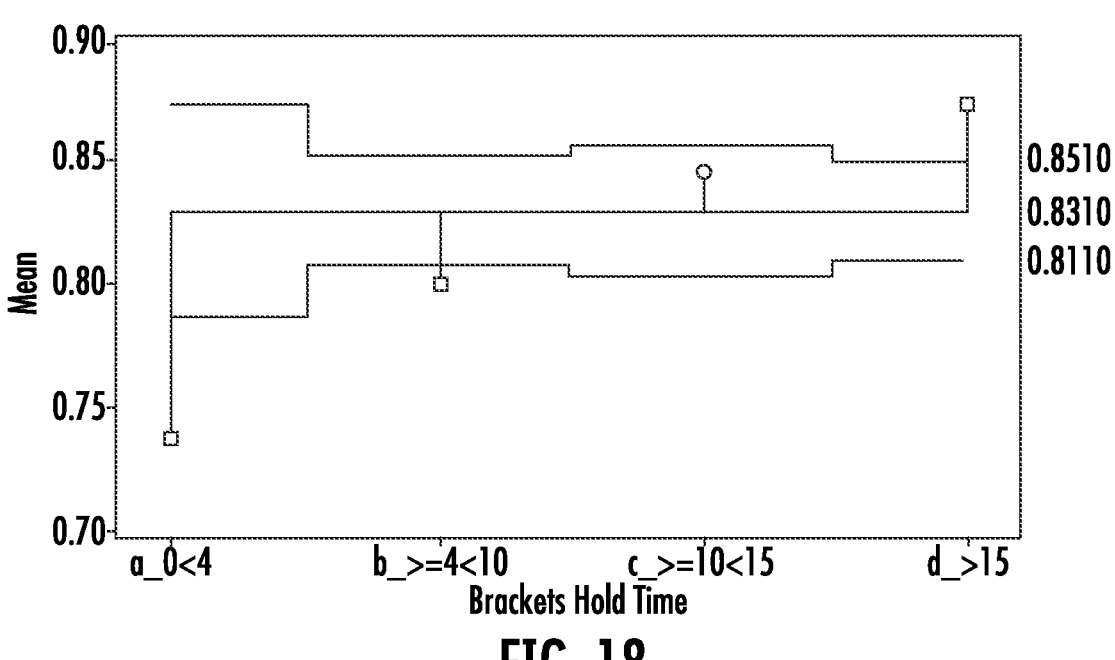
Figure 19:
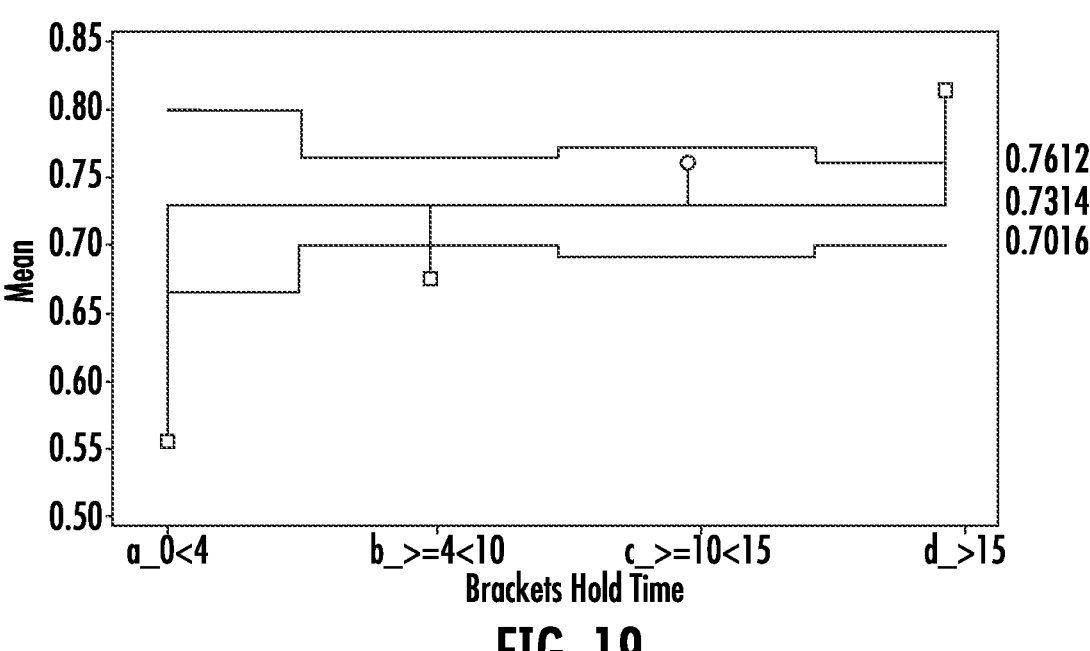
Figure 20:
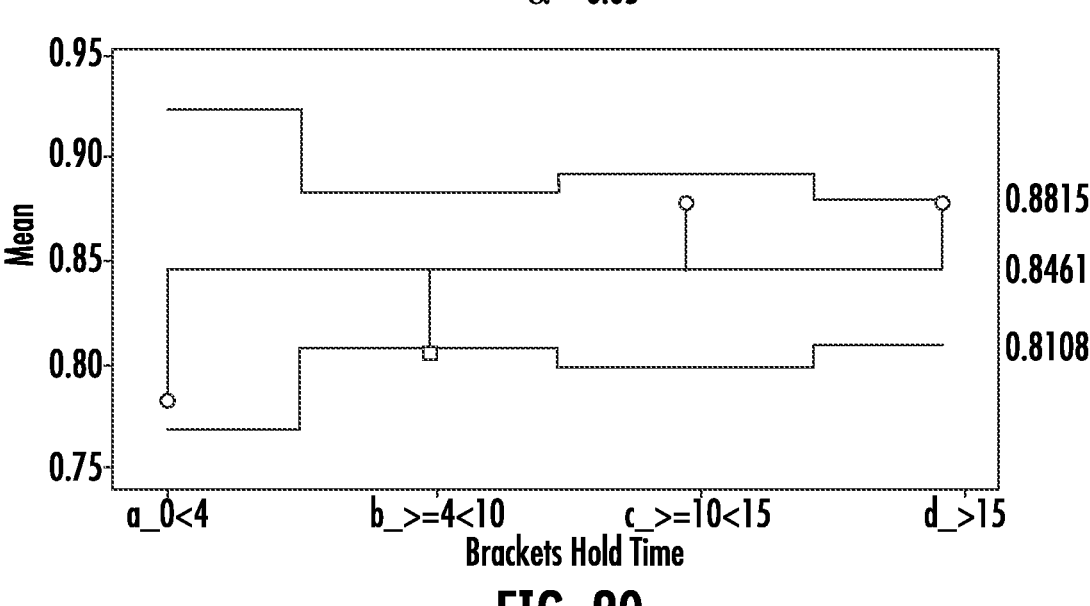

FIG. 14 is a line chart showing the analysis of variance (ANOVA) for the ratio of free fatty acids versus fatty acids on the five key free fatty acids per the mill and hold time.

FIG. 15 is a line chart showing the brackets hold time impact on the equal variances of free fatty acids/fatty acids.

FIGS. 16-20 are the analysis of variance line charts for the respective percentage of each of five actives as respective lauric, myristic, oleic, linoleic, and linolenic free fatty acids, and showing the particular individual fatty acids and percentage of the free fatty acids versus fatty acids.

FIGS. 21-26 are tables of the statistics and ranges for the respective five active fatty acids shown in the line charts of FIGS. 16-20 and showing the percentage of free fatty acids versus fatty acids and post mill hold time in days.

Figure 27:
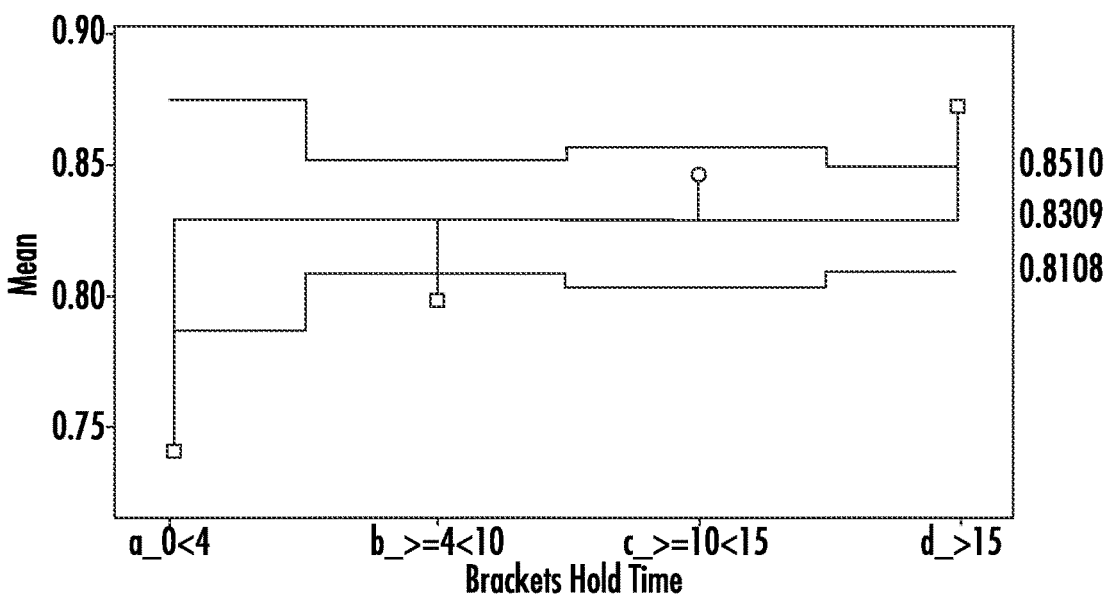

FIG. 27 is a line graph showing the post milling hold time brackets for the five active fatty acids and the ratio of free fatty acids versus fatty acids.

Figure 28:
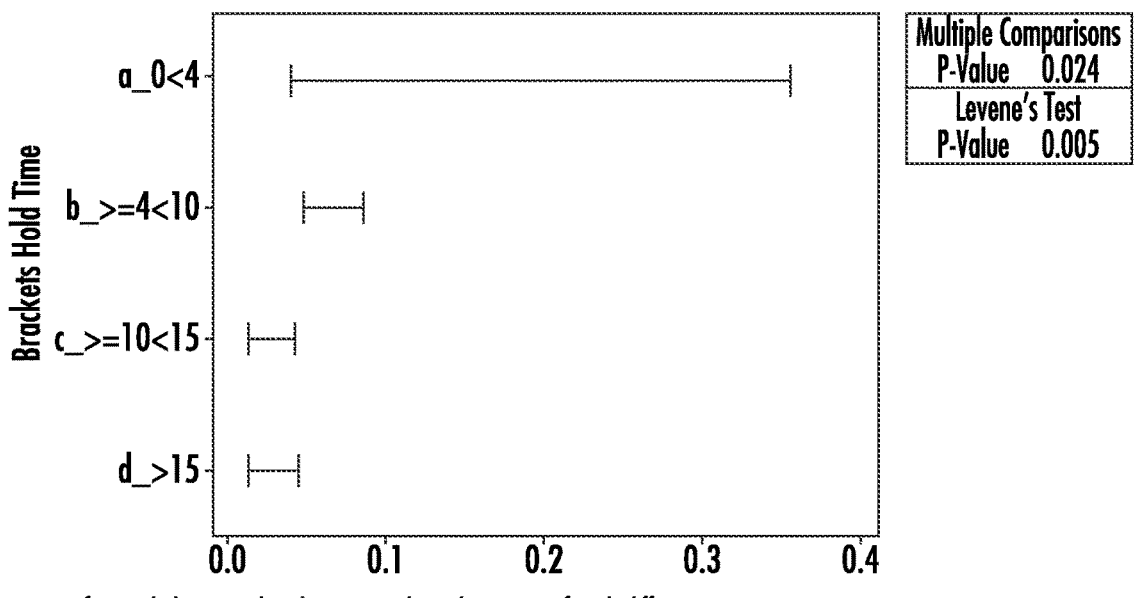

FIG. 28 is a line graph showing the test for equal variances for the five active fatty acids and the ratio of free fatty acids versus fatty acids.

FIGS. 29-33 are line graphs showing the respective five active fatty acids weight fraction versus the post mill hold time for the five actives of FIGS. 16-20.

Figure 32:
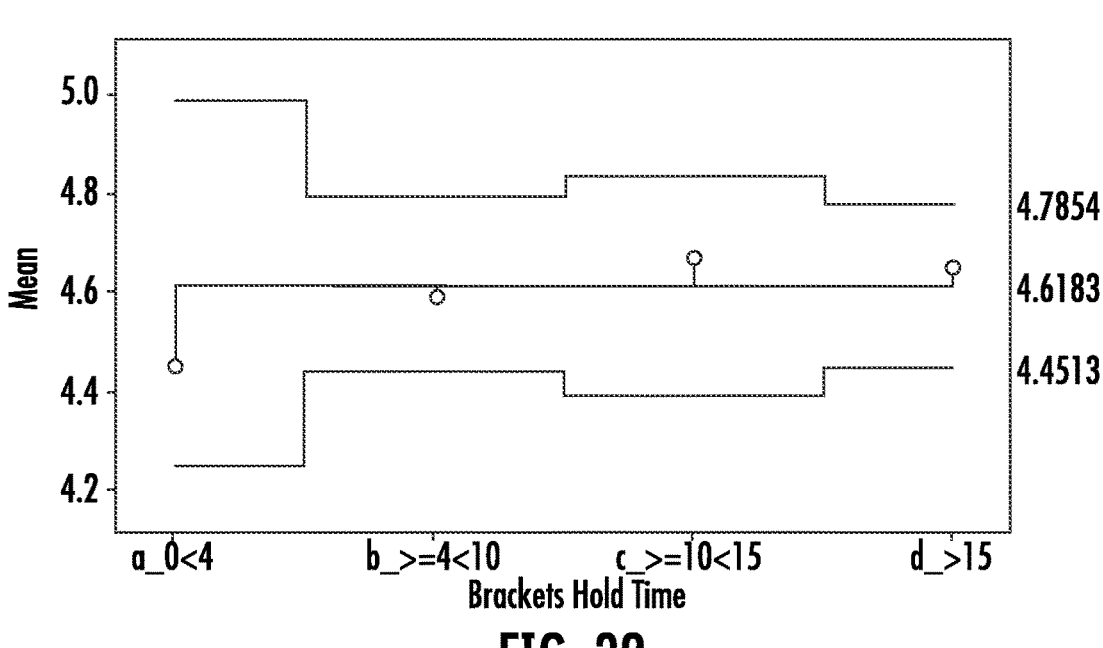
Figure 33:
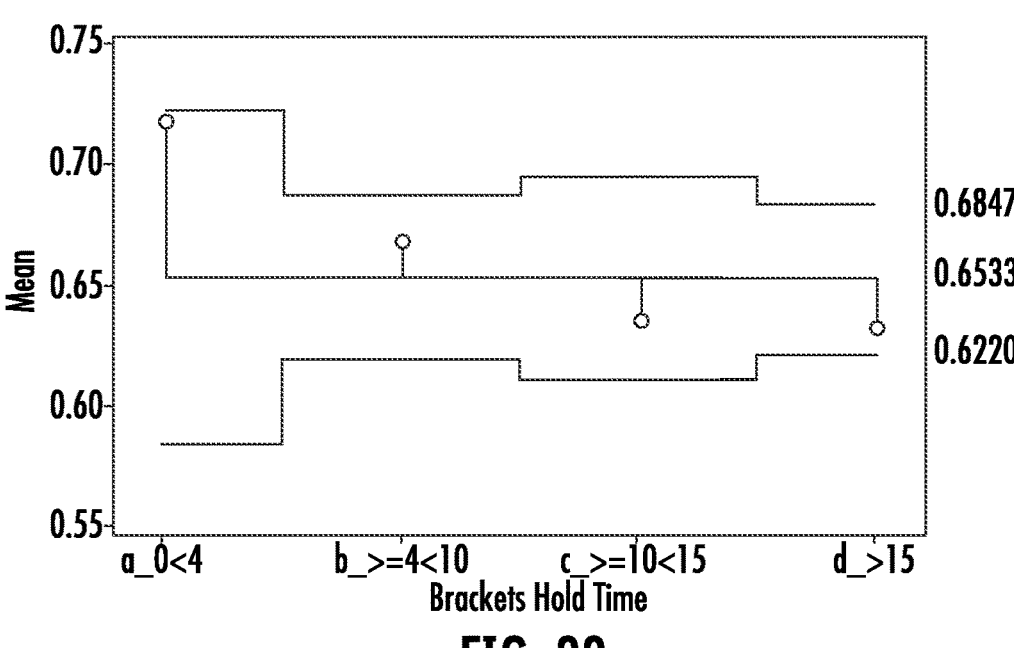
Figure 34:
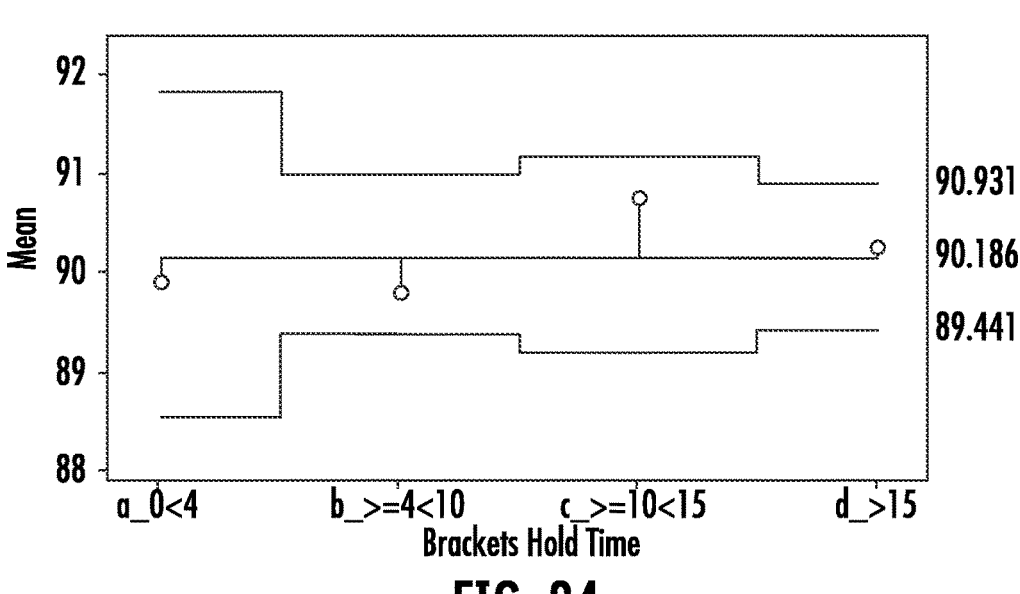

FIG. 34 is a line graph similar to that shown in FIGS. 29-33, but showing the total fatty acids weight fraction versus the post mill hold time.

FIG. 35 is a table showing the multiple regression for the total free fatty acids/fatty acids.

Figure 36:
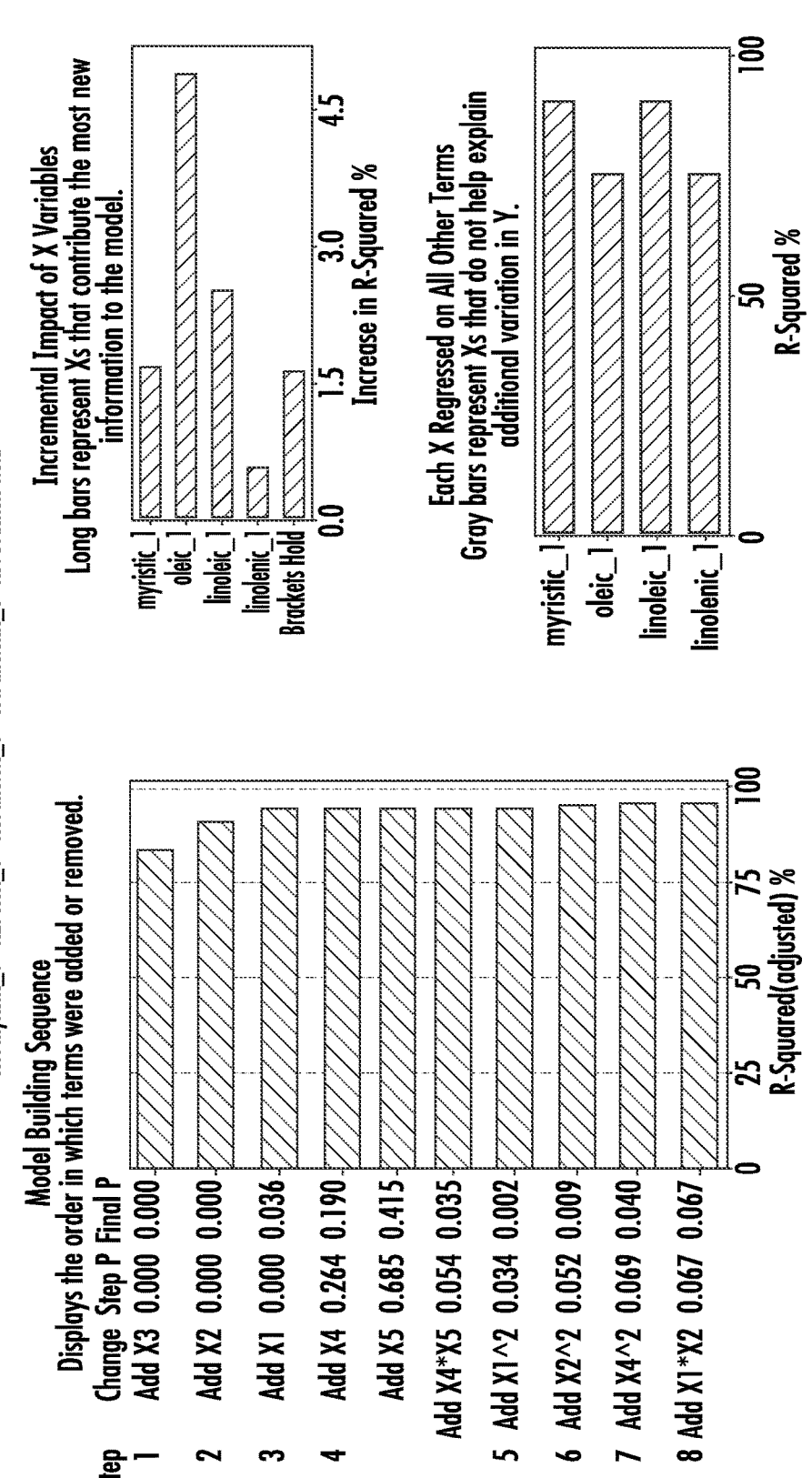

FIG. 36 are bar charts showing the multiple regression for the total free fatty acids/fatty acids.

Figure 37:
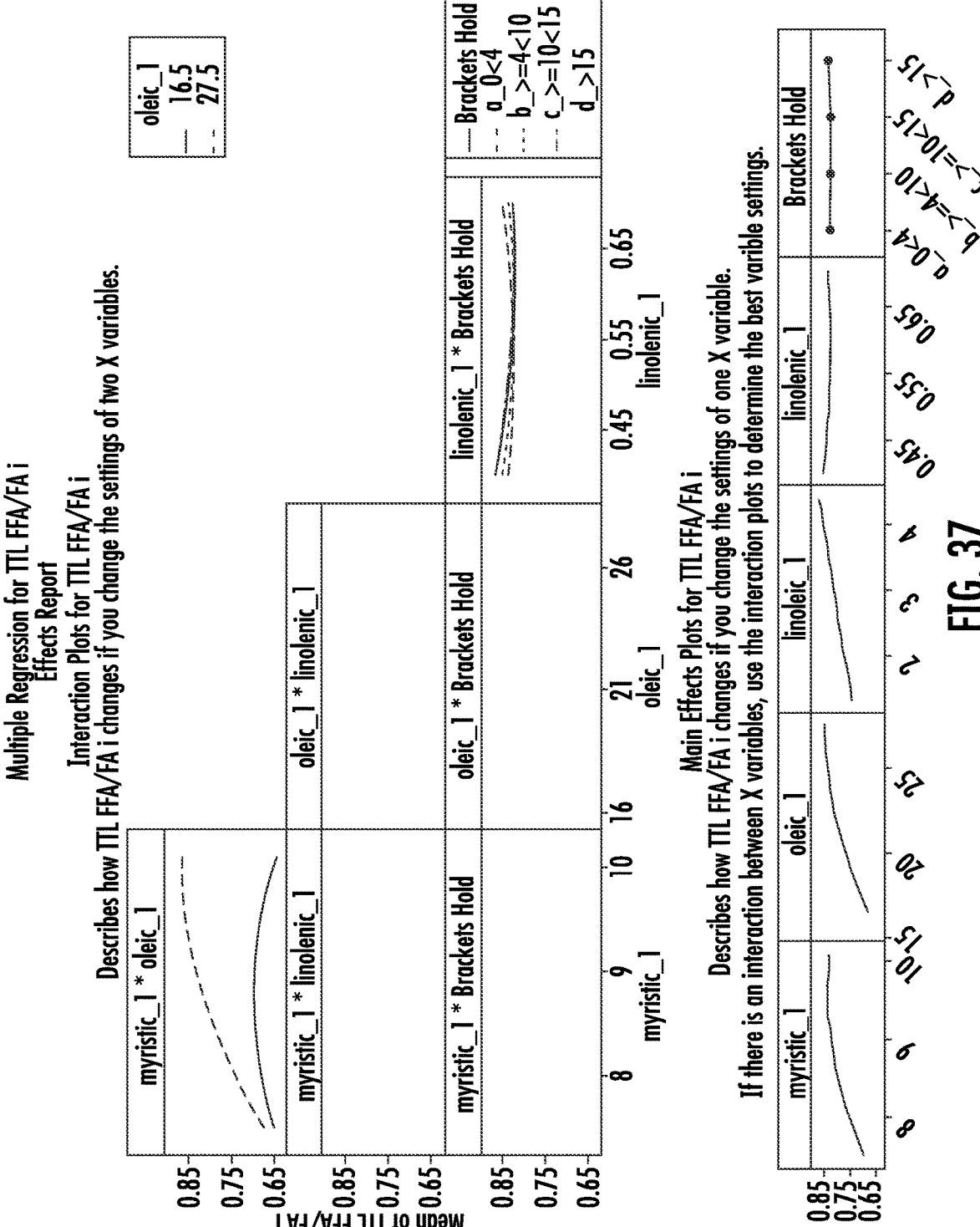

FIG. 37 are graphs showing the multiple regression for the total free fatty acids/fatty acids and hold time and the effects, and showing how the total ratio changes when settings are changed.

Figure 38:
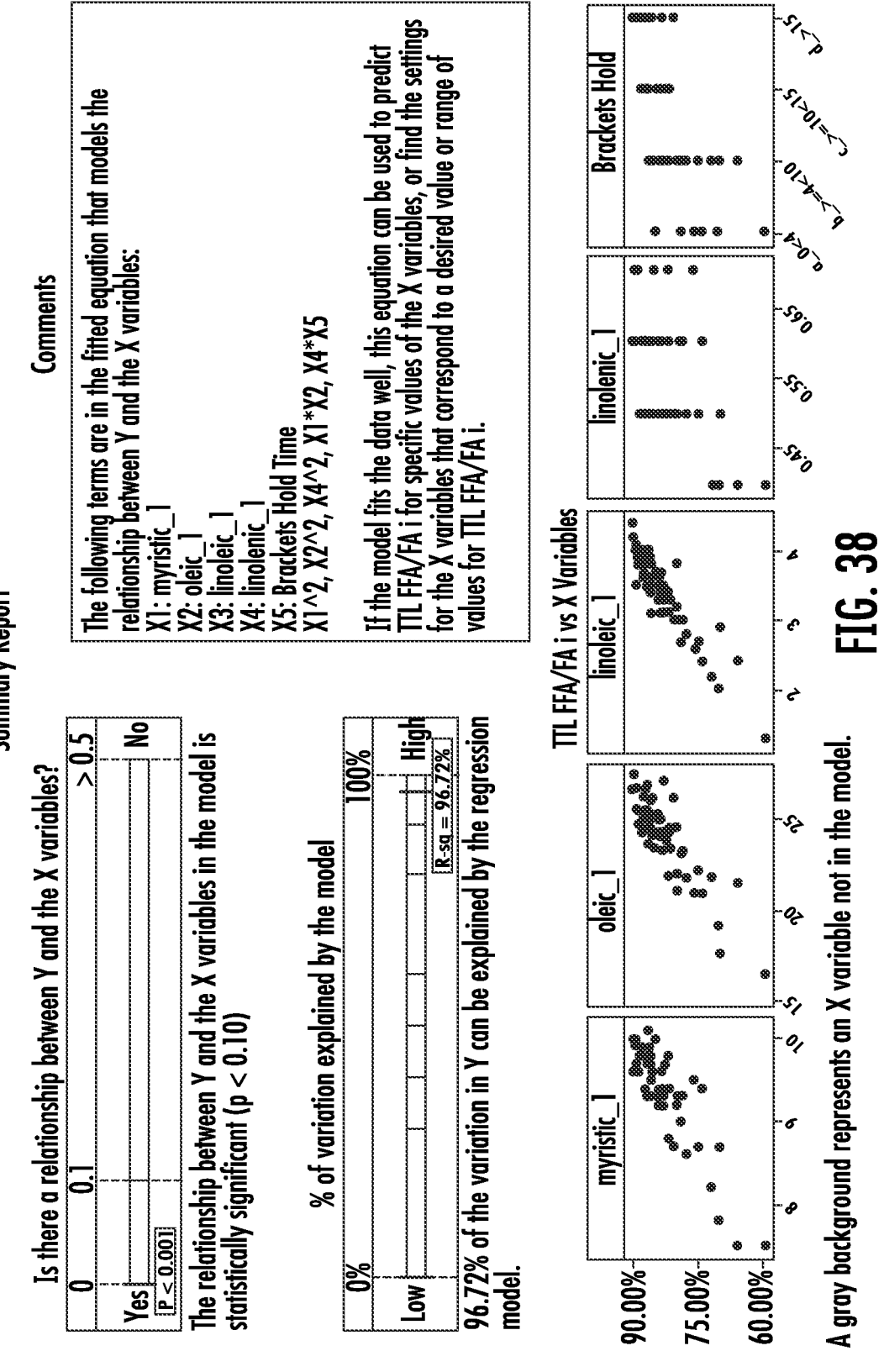

FIG. 38 are bar charts and scatter plots showing the multiple regression summary report for total free fatty acids/fatty acids and impact of x variables.

FIG. 39 are scatter plots showing the multiple regression for total free fatty acids/fatty acids as a diagnostic report of residuals versus fitted values.

FIG. 40 are bar charts showing the multiple regression for total free fatty acids and incremental impact of x variables.

Figure 41:
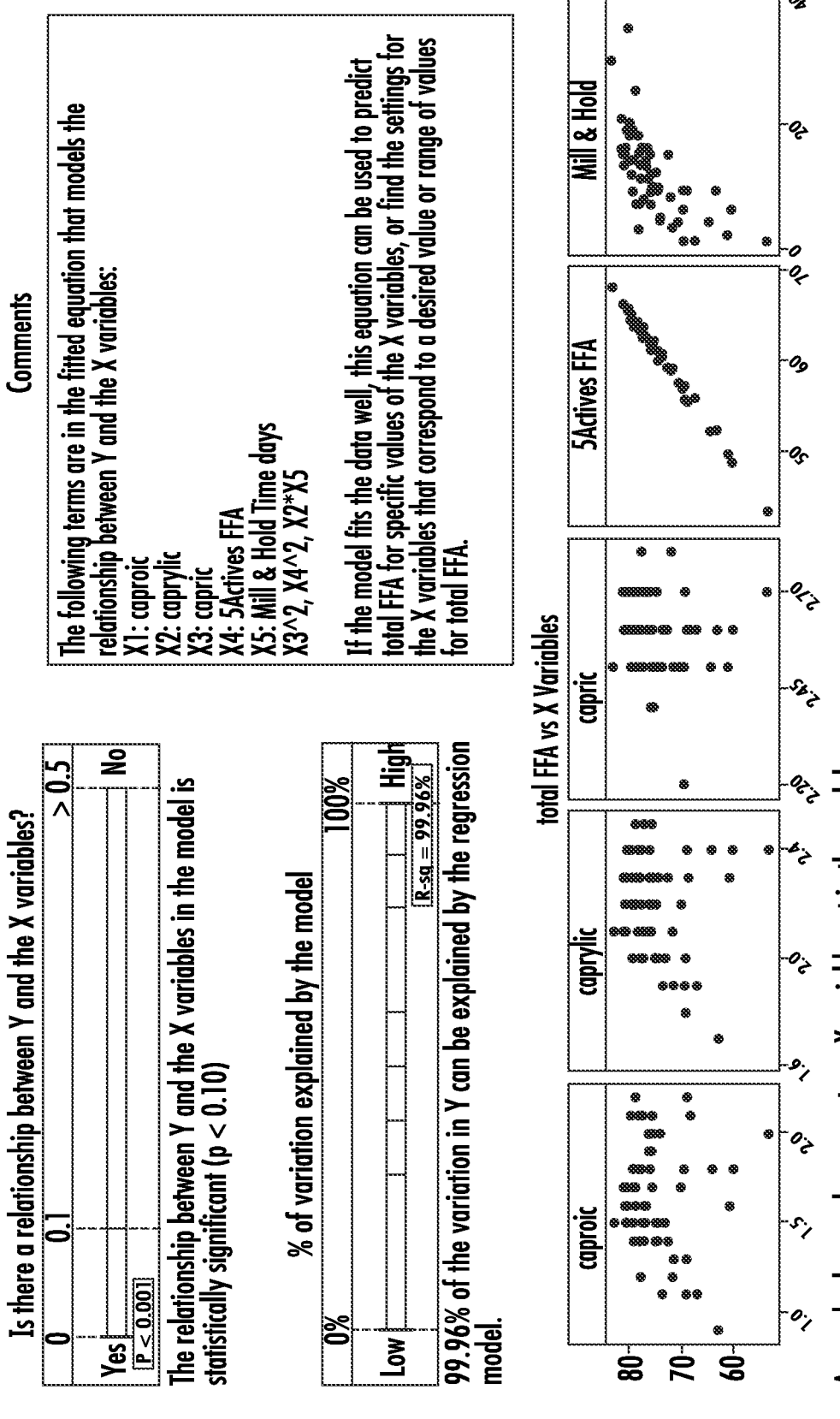

FIG. 41 are bar charts and scatter plots showing the multiple regression for total free fatty acids and impact of different variables.

Figure 42:
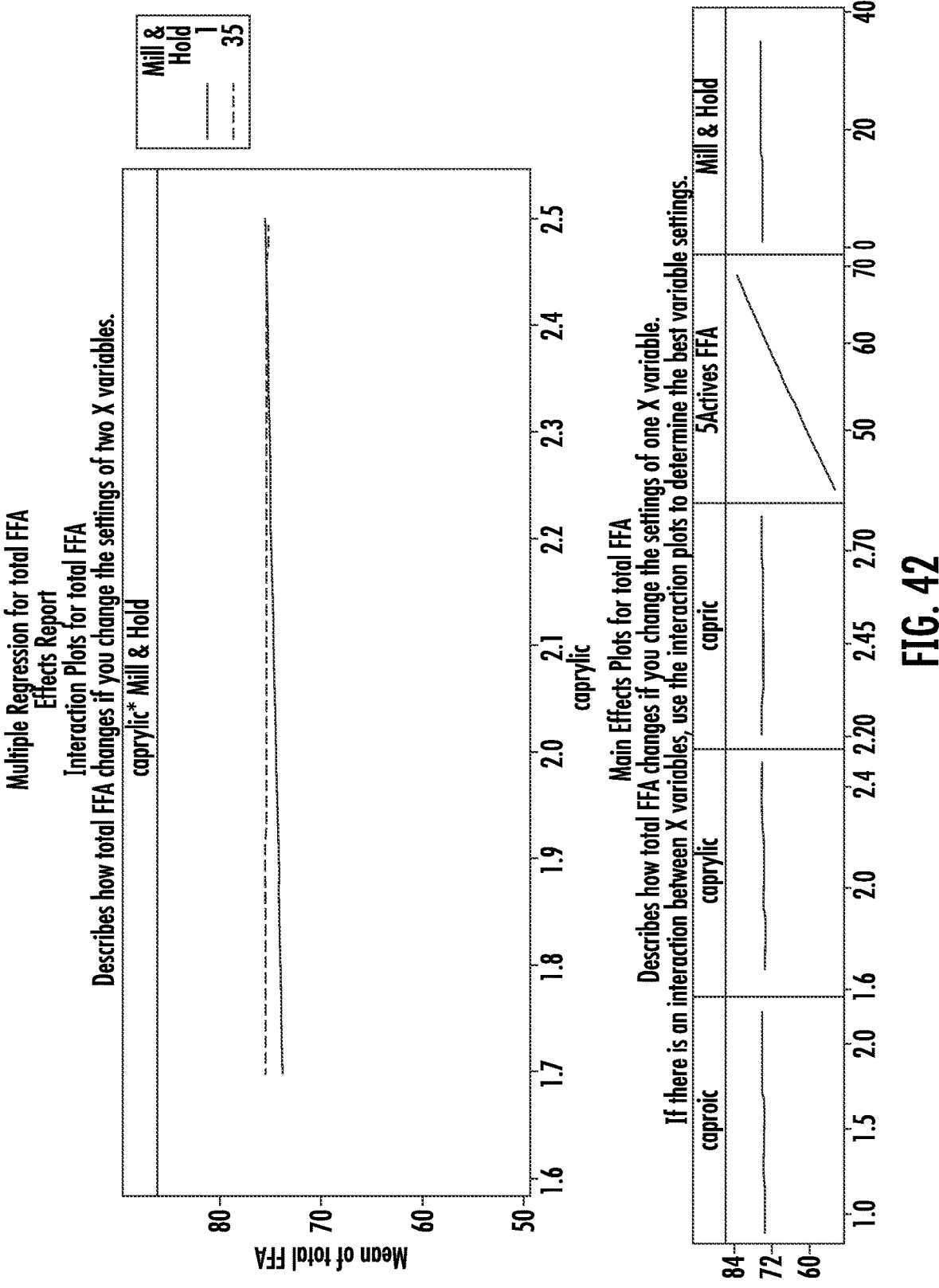

FIG. 42 are graphs showing the multiple regression for total free fatty acids and how the total free fatty acids change if the settings of two x variables are changed.

Figure 43:
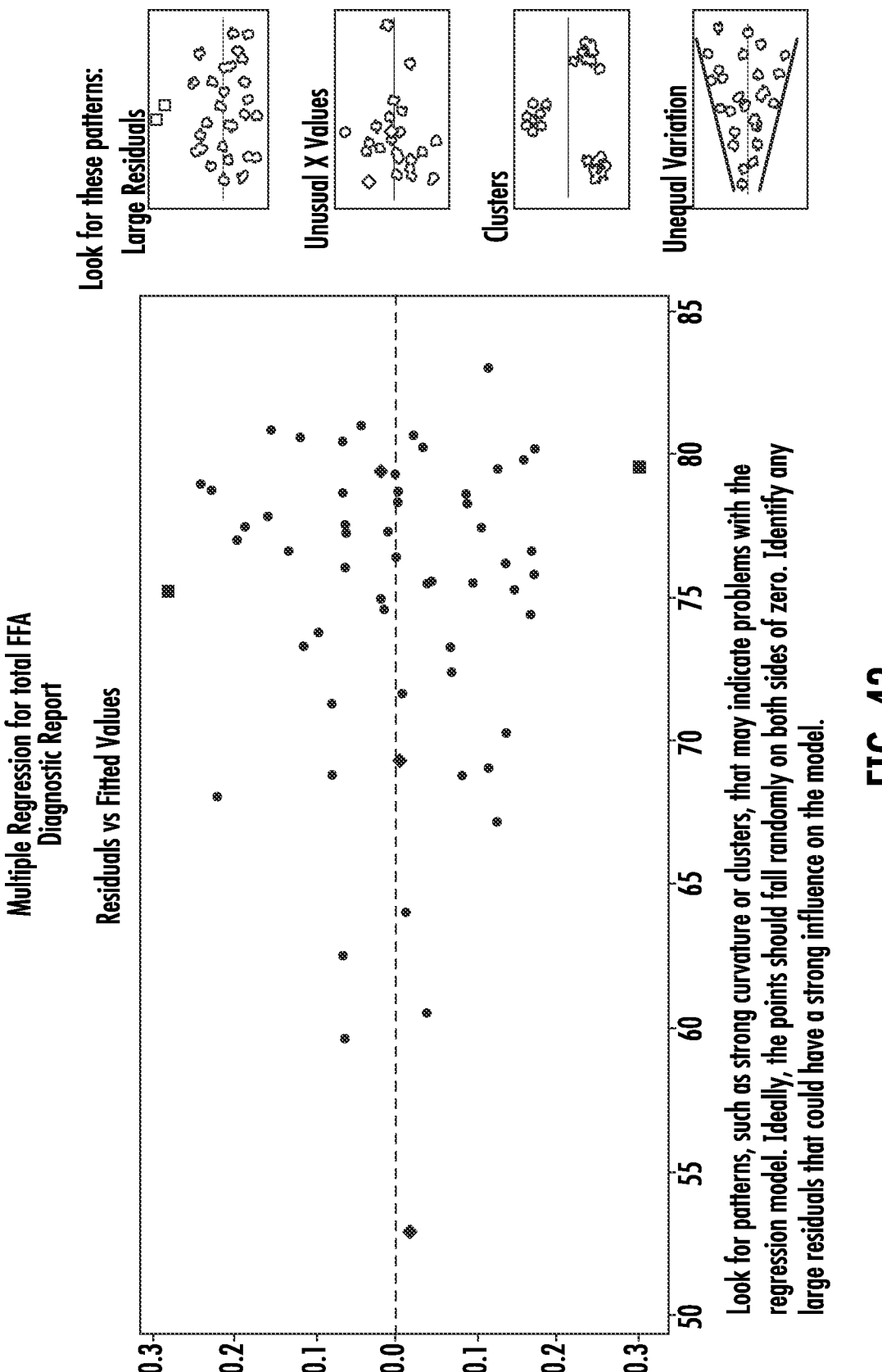

FIG. 43 are scatter plots showing the multiple regression for total free fatty acids and residuals versus fitted values.

Figure 44:
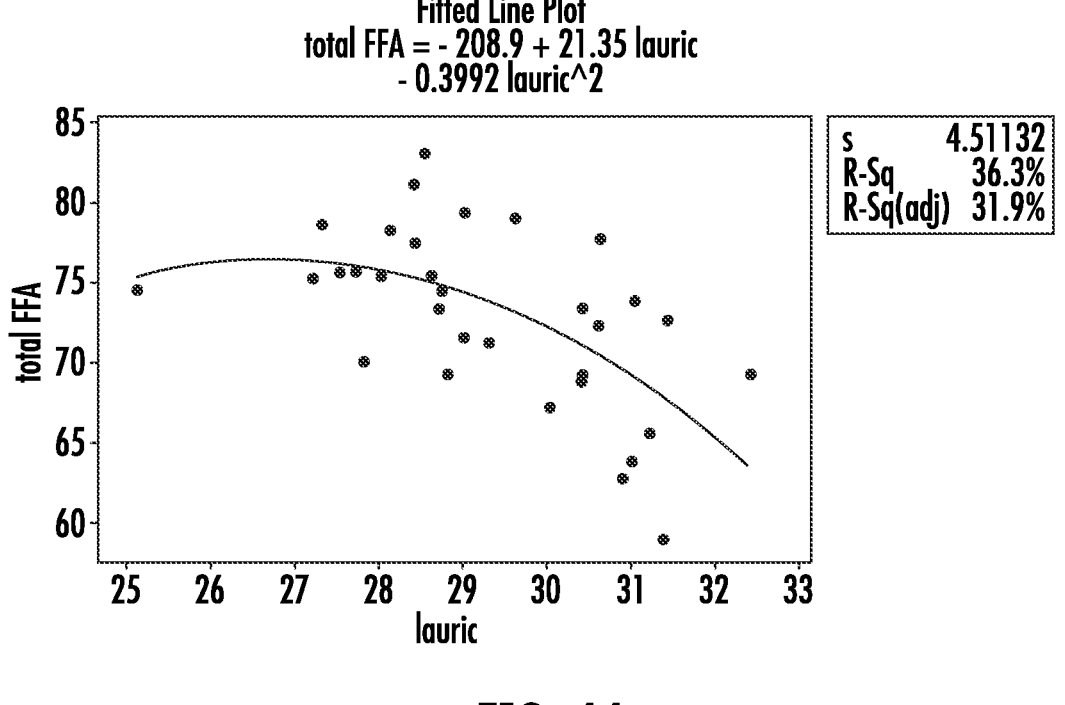

FIG. 44 is a graph of a fitted line plot showing total free fatty acids and lauric acid.

Figure 45:
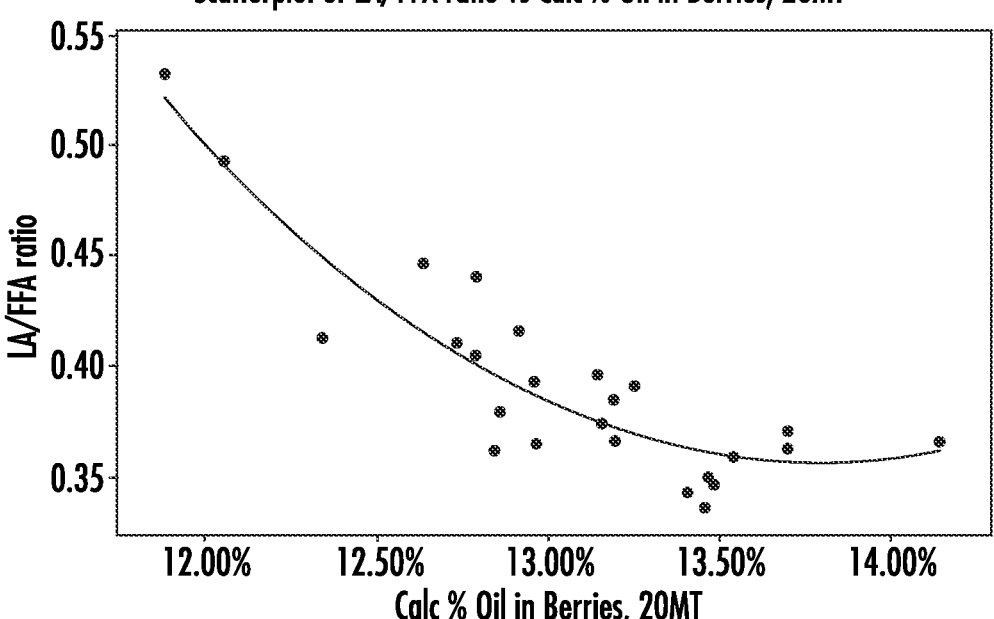

FIG. 45 is a graph showing a scatter plot of lauric acid/free fatty acid ratio versus the percent oil in berries.

Figure 46:
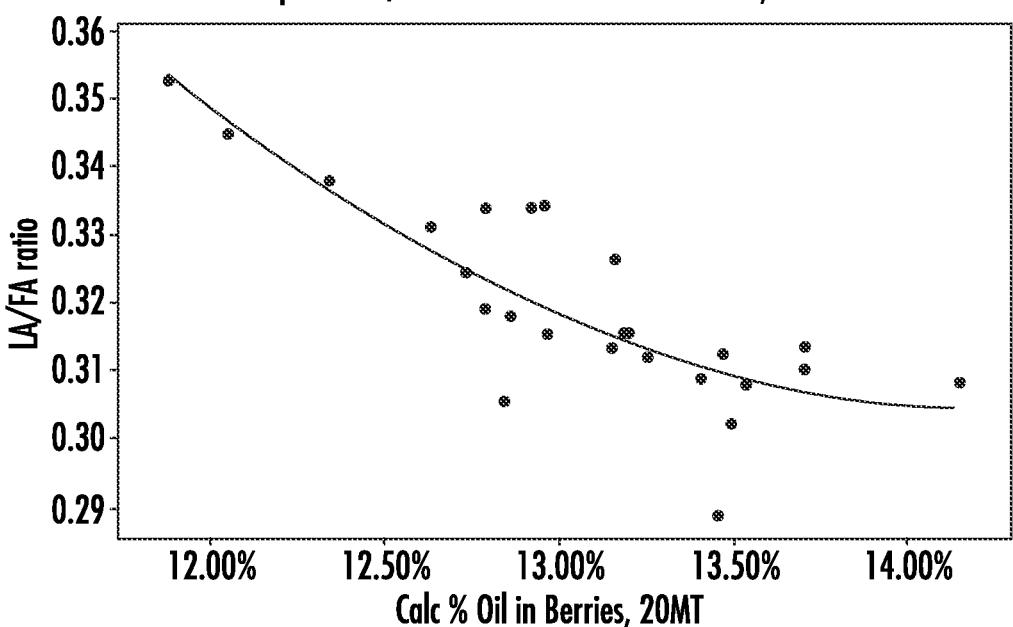

FIG. 46 is a graph similar to FIG. 45, but showing a scatter plot of the lauric acid and fatty acid ratio versus the percent oil in berries.

Figure 47:
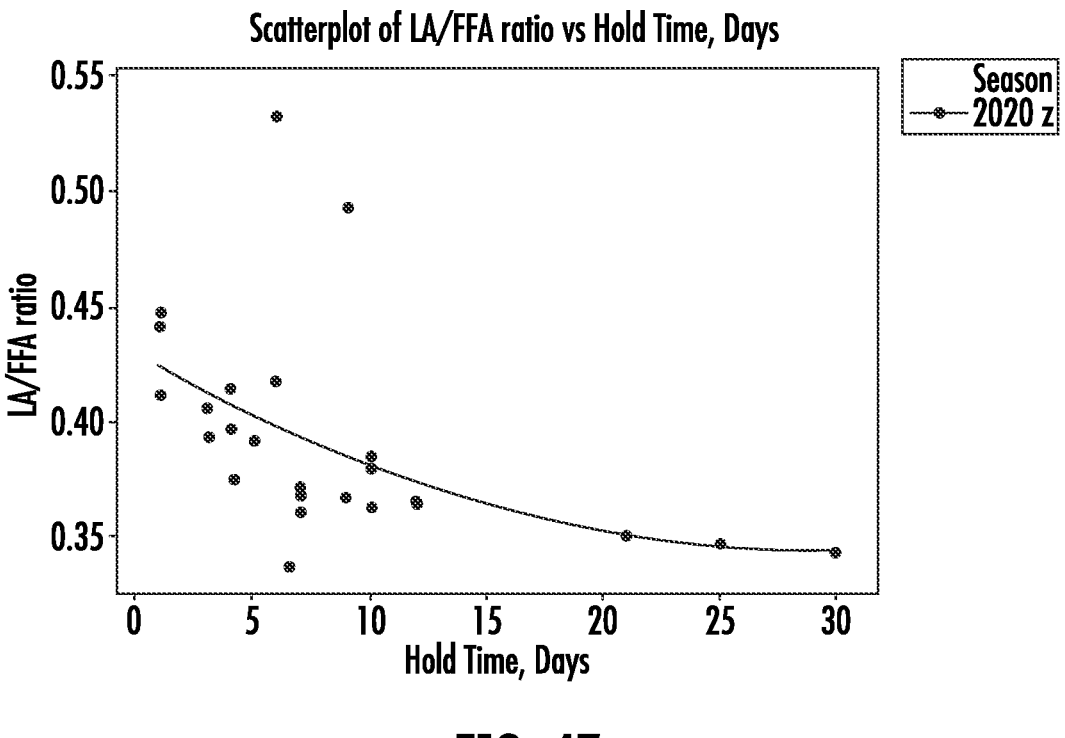

FIG. 47 is a graph showing a scatter plot of the lauric acid/free fatty acid ratio versus hold time in days.

Figure 48:
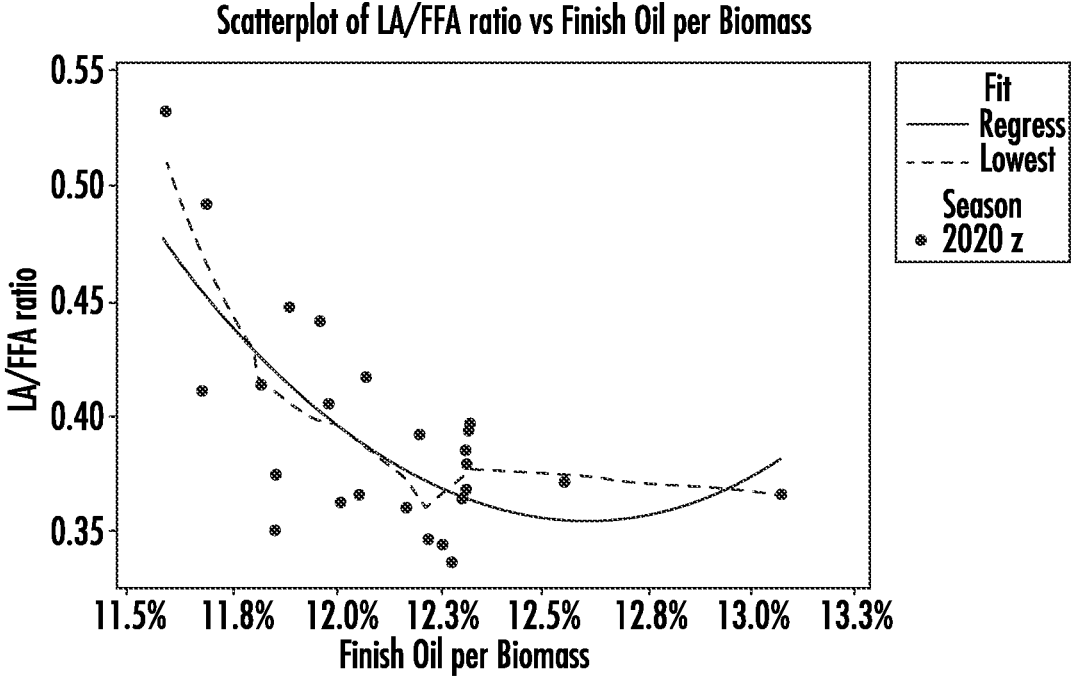

FIG. 48 is another graph of a scatter plot of the lauric acid and free fatty acid ratio versus the finish oil per biomass.

Figure 49:
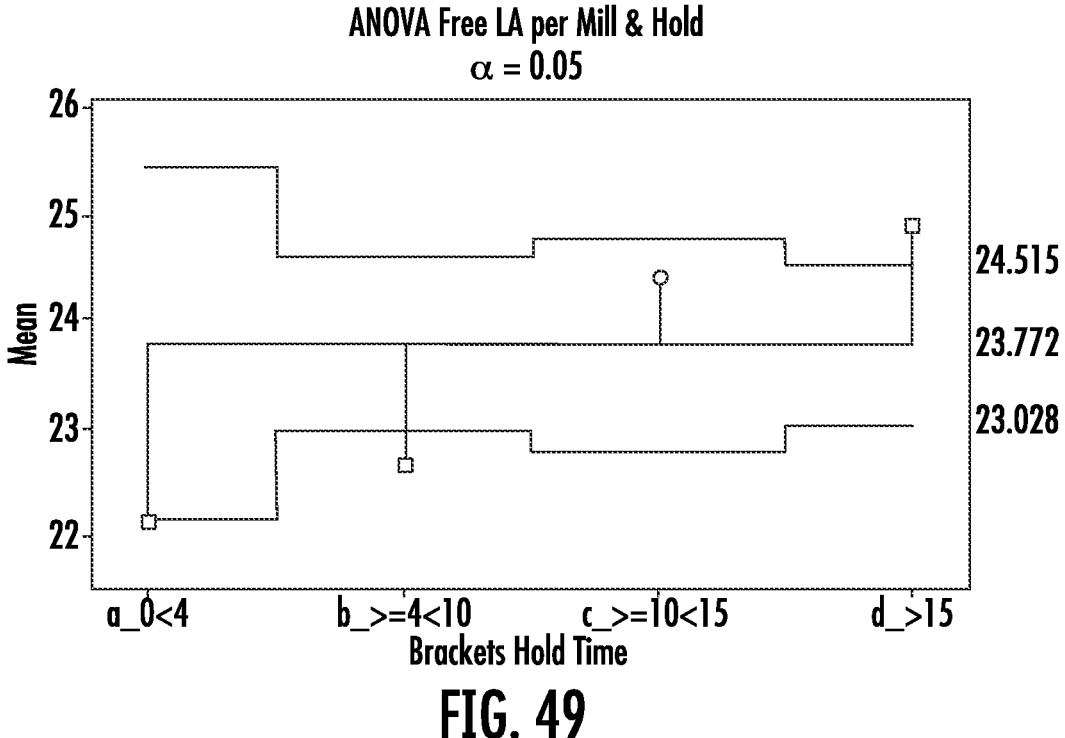

FIG. 49 is an analysis of variance line charts showing the free lauric acid per mill and hold.

Figure 50:
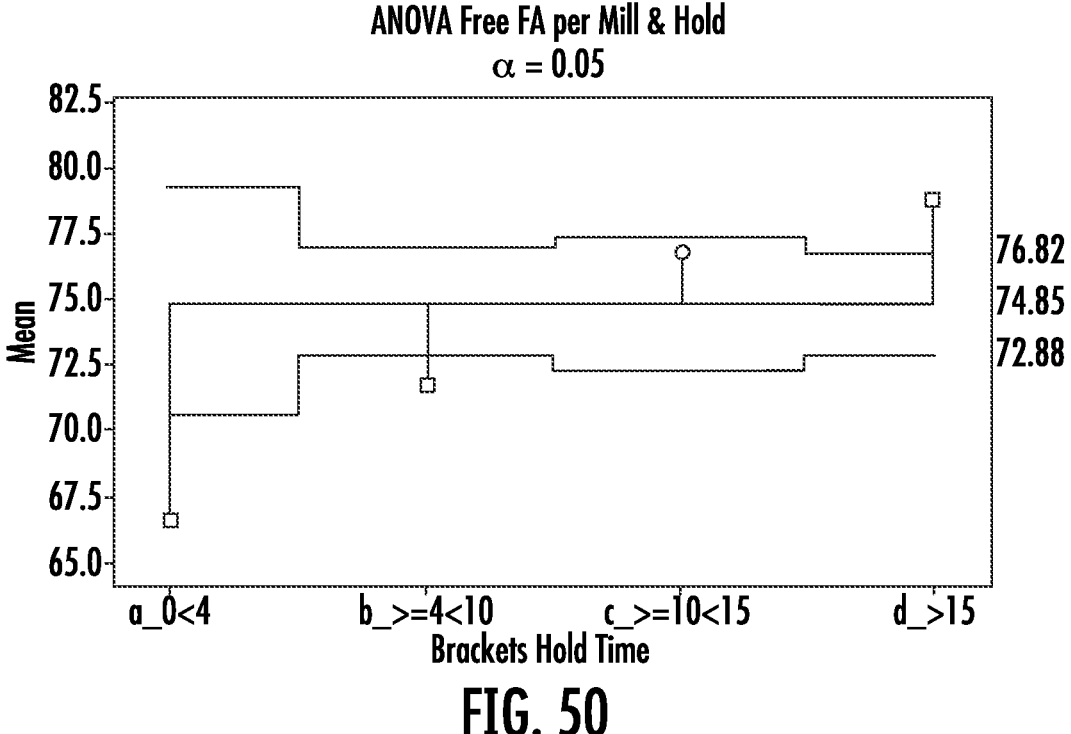

FIG. 50 is another analysis of variance line charts showing the free fatty acid per mill and hold time.

FIG. 51 are bracket line charts showing the test for equal variances of lauric acid versus the hold time.

FIG. 52 are bracket line charts similar to FIG. 51 showing the test for equal variances of total free fatty acids versus the bracket hold time.

Figure 53:
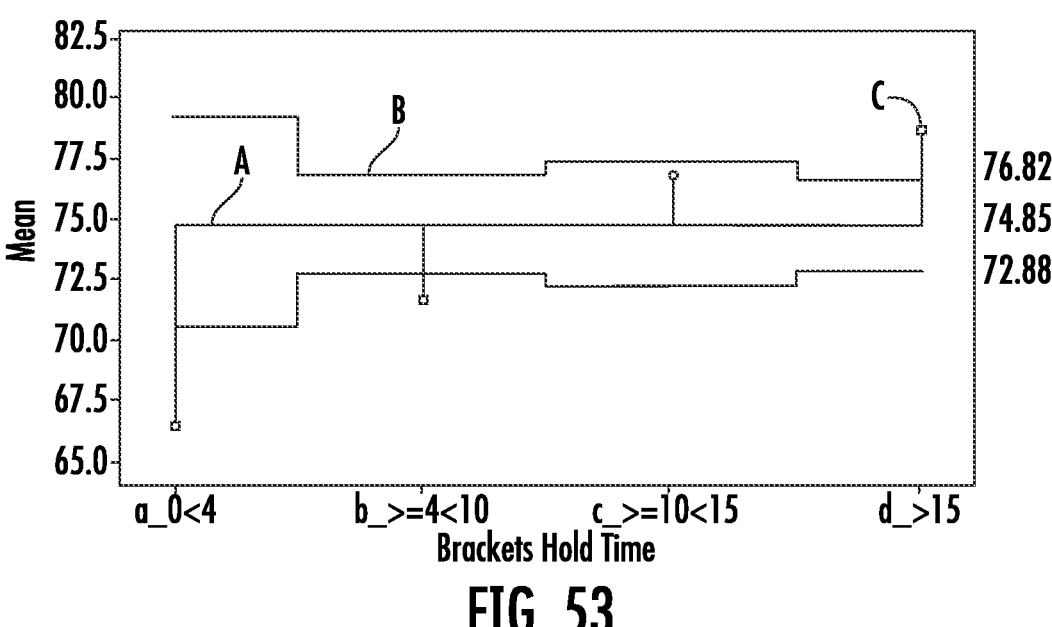

FIG. 53 is a line graph showing the analysis of variance for free fatty acids per mill and hold time.

Figure 54:
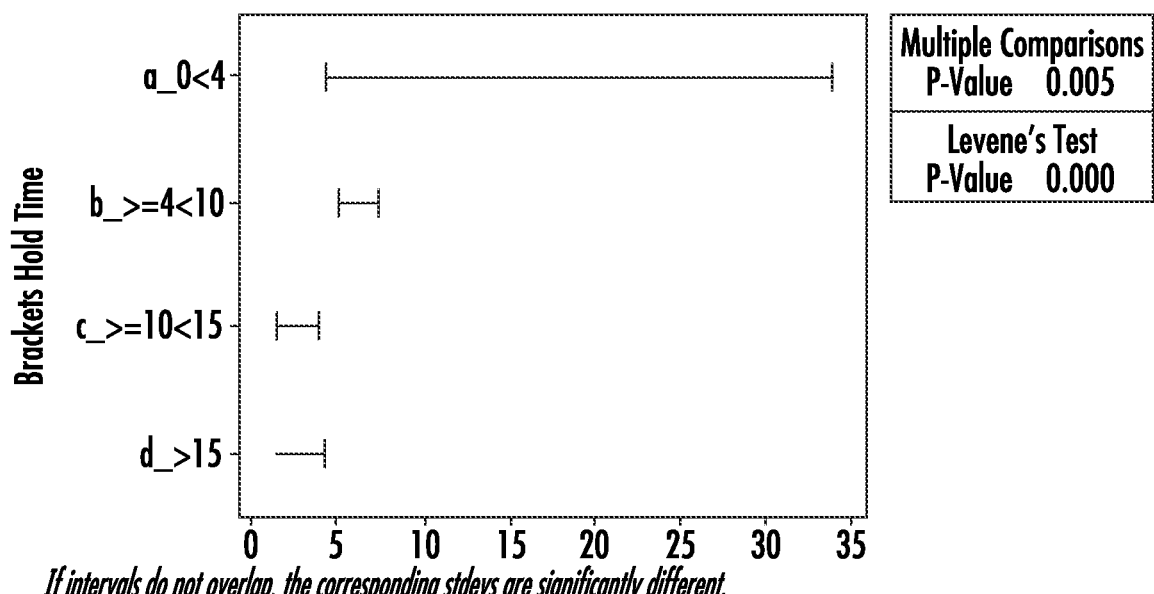

FIG. 54 is another bracket line chart showing the test for equal variances for the total free fatty acid versus the brackets hold time.

Figure 55:
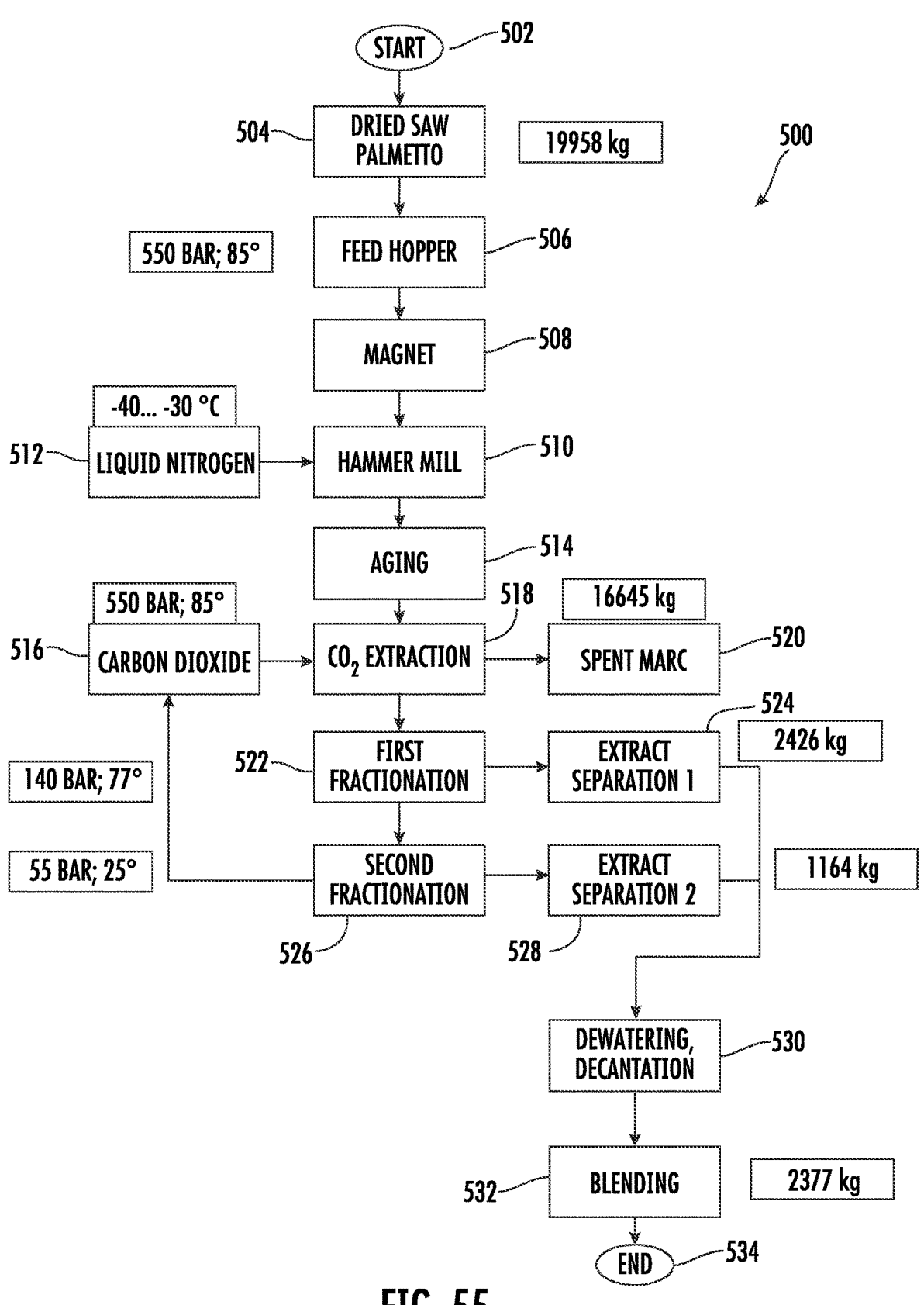

FIG. 55 is a high-level flowchart showing a method for producing the LSESr batches such as Experiments 5 and 6 as shown in FIGS. 4A and 4B using supercritical $CO_2$ extraction to produce the enhanced LSESr of the current invention.

FIG. 56 is a table of comparative data for high and low pressure extraction using the same raw material.

DETAILED DESCRIPTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art.

Figure 1:
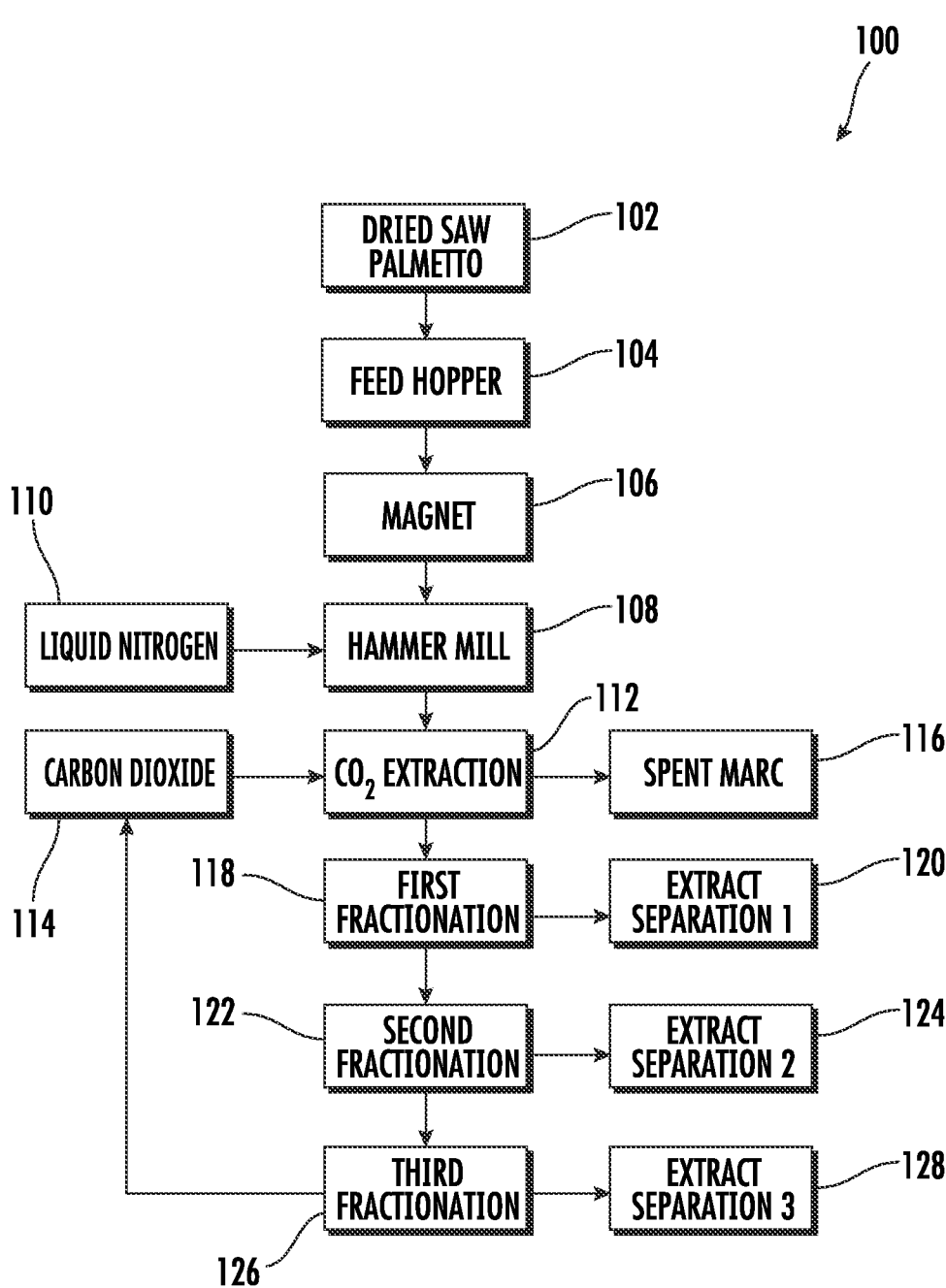
FIG. 1 is an example of a high level flowchart showing an example method of producing the lipidosterolic extract of *Serenoa repens* (LSESr).

A method of processing saw palmetto berries to form a lipidosterolic extract as a dietary supplement composition by supercritical fluid extraction using $CO_2$ under high pressure is illustrated in the high level flowchart of FIG. 1 shown generally at 100.

The LSESr of the current invention is an enhanced LSESr that is improved over hexane solvent extracts such as commercially available Permixon® that contains residue of hexane and as it is environmentally friendly process. For purposes of description, the LSESr of the current invention will be described as an enhanced LSESr and has a favorable and advantageous 1) ratio of free fatty acids to total fatty acids; 2) higher enrichment of the free fatty acids of lauric, myristic, oleic, and linoleic as free fatty acids to total free fatty acids; and 3) specific free fatty acids tailored for specific end uses, such as more enhanced linoleic and linolenic free fatty acids such as above 3.7% of total free fatty acids for hair health, and such as in uses for prostate, hair health, and skin care with other free fatty acids. It has been found as explained further below that pre-extraction processing of the saw palmetto berry before the $CO_2$ extraction has an important role in the final enhanced LSESr free fatty acid and fatty acid components that gives the best support for prostate, hair, and skin uses.

For example, hair happens to have numerous androgen receptors and the enhanced LSESr is especially useful for inhibiting the activity of 5α-Reductase-1 and 2 in certain individuals compared to the scalp of normal individuals, which has been seen to have a beneficial effect on hair health. The enhanced LSESr in an example, such as described below with reference to FIGS. 4A and 4B and the flowchart of FIG. 55, has a better profile not due to total higher fatty acids or higher free fatty acids or the level of important free fatty acids. The better profile is driven by pre-extraction handling and $CO_2$ extraction parameters for ripe berries to achieve the right balance of free fatty acids to total (greater than about 80%), and at the same time, achieve a higher enrichment of the four important bioactive fatty acids (lauric, myristic, oleic, and linoleic) as a proportion of free fatty acids (greater than about 82.0%), thus delivering the most potent enrichment of bioactive fatty acids. It has been found that the concentration of total fatty acids is less important than the ratio of free fatty acids to total fatty acids and the optimized contribution of the four bioactive free fatty acids as a percentage of total free fatty acids.

For example, enhanced berry processing and specific extraction and separation pressure, temperatures and even times may be selected to form a final product as the enhanced LSESr of the current invention as described above, which also provides for a peroxide value that is less than about 3 meq/kg and a shelf stability of at least 4 years without added antioxidants and stabilizers. Generally, the enhanced LSESr is a shelf stable, supercritical $CO_2$ fluid extracted, enhanced lipidosterolic extract of *Serenoa repens* (LSESr), the LSESr having a ratio of free fatty acids to total fatty acids that is greater than about 80.0% and an enrichment of lauric, myristic, oleic and linoleic acids as free fatty acids to total free fatty acids that is greater than about 82.0%. In an example, the enhanced LSESr may have a balance of about a preferred 90.0% of total fatty acids to about 72.0% free fatty acids, and in a specific example, about 88.9% to about 90.2% of total fatty acids to about 72.4% to about 72.6%. The enhanced LSESr may have an enrichment of lauric, myristic, oleic and linoleic free fatty acids to total free fatty acids of about 82.0% to about 84.0%. The enhanced LSESr may have a ratio of free fatty acids to total fatty acids of about 80.0% to about 82.0%. These are non-limiting ranges and the values may range from about 2 to 3% above and below these ranges.

The enhanced LSESr may be used in a composition formulated in a therapeutic amount to maintain and promote hair health and growth in a human in need thereof. In this example the composition is a shelf-stable, supercritical $CO_2$ fluid extracted, enhanced LSESr that has a ratio of free fatty acids to total fatty acids that is greater than about 80.0% and an enrichment of lauric, myristic, oleic and linoleic acids as free fatty acids to total free fatty acids that is greater than about 82.0%, and an enrichment of linoleic and linolenic acids together is greater than about 3.7%. The composition may be formulated as a topical lotion to be applied to the hair. The composition may include any one or more of zinc, vitamin D, rosemary oil and olive oil. The composition may include up to about 5.0% of Minoxidil.

The enhanced LSESr is preferably not contained on a carrier such as PEG (polyethylene glycol) to stabilize the free fatty acids, as compared to the commercially available Permixon®, which is on the PEG carrier. In addition to the four active free fatty acids listed above, a fifth as linolenic free fatty acid has been found to be advantageous to help with 5α-Reductase Type 1 as well as 5α-Reductase Type 2 as an inhibitor for hair treatment. The enhanced LSESr is produced using the inventive preprocessing, extraction and separation parameters to deliver the most active form of the free fatty acids for prostate and hair health. Use of preprocessing and pre-extraction processing, such as specific grinding and blending, gives better plating and densifies the powder. The front-end processing and aging of berries and attendant time sequencing of the saw palmetto powder after grinding allows for the exposure of the internal cell structure that helps the overall reaction and end product. These parameters include micromilling under cryogenic conditions and holding or ageing it.

Free fatty acids of the enhanced LSESr are better localized to the prostate, especially as a food source over glucose. The enhanced LSESr inhibits both the 5α-Reductase-1 and 2 enzymes that are especially beneficial for hair growth, and inhibits the 5α-Reductase-2 enzyme that is especially beneficial for prostate health. The free fatty acids of the enhanced LSESr localize to tissues with high high androgen receptor activity, like the prostate or the scalp, and can impact androgen receptors like 5α-Reductase 1 and 2. The preprocessing parameters as described below in greater detail help open up the berry matrix. The free fatty acids are better able to insert into the nuclear membrane with its attendant inhibitory effects on 5α-Reductase to prevent conversion of testosterone to DHT. Normal and routine extraction of saw palmetto berries produces usually about 70% free fatty acids or less, which is well below the percentage of free fatty acids in the enhanced LSESr of the current invention.

Androgens play an important role in prostate growth and development and in hair growth. Chief among these androgens are testosterone and dihydrotestosterone (DHT). The 5α-reductase (5αR) enzymes are responsible for converting testosterone into the more potent dihydrotestosterone (DHT). There are three different types, or isoforms, of the 5α-reductase (5αR) enzymes: 5αR-1, 5αR-2, and 5αR-3. These isoforms can be found in various tissues and in varying amounts throughout the body.

However, 5αR-2 in particular can become overexpressed in prostates of aging men leading to prostate enlargement. Meanwhile, both 5αR-1 and 5αR-2 can become overexpressed in the scalps of men or women who are genetically susceptible to androgenic hair loss. As will be explained in greater detail below with reference to FIG. 7A, the graphs show the overexpression of 5αR-1 and 5αR-2 in women with normal hair growth versus women with female pattern hair loss (FPHL).

Both testosterone and DHT can bind to and activate androgen receptors, but DHT is more potent. Activation of androgen receptors leads to gene expression. Since DHT is more potent, it induces higher levels of gene expression when it activates androgen receptors, compared to the less potent testosterone. Overexpression of 5αR enzymes in the prostates of aging men or in the scalps of individuals susceptible to androgenic hair loss leads to the overproduction of DHT. More DHT means an even greater response in gene expression. That imbalance in gene expression can then lead to abnormal function in the tissue, like prostate enlargement or hair loss.

Certain fatty acids found in saw palmetto extract can inhibit the 5αR enzymes in the prostate and scalp as shown in FIG. 3 and explained in greater detail below. Fatty acids can exist in the free, unbound form, or bound to other molecules, like to glycerol forming triglyceride, for example.

The combination of the free fatty acids plus bound fatty acids is the total fatty acid level.

Identification: Unlike animal oils or most vegetable oils which contain fatty acids mainly in the form of triglycerides, saw palmetto oil extract is rich in free fatty acids. One method of identifying authentic saw palmetto extracts from imitation or adulterated extracts is to test the free fatty acid levels as a percentage of the total fatty acid levels. High-quality saw palmetto extracts contain ≥70% free fatty acids.

Absorption: Free fatty acids are absorbed twice as well as triglycerides.

Disposition: Once absorbed into the body, free fatty acids tend to localize to the prostate and scalp. Why? Because cells with high expression of androgen receptors, like those in the prostate or scalp, also express fatty acid transporters on the cell surface. Those transporters preferentially pull free fatty acids into the cell instead of bound fatty acids.

Activity: Free fatty acids are the active ingredients in saw palmetto extracts. Certain free fatty acids are potent inhibitors of the 5αR enzymes, versus other forms of fatty acids which are inactive, as shown in FIG. 3 with the esterified fatty acids and fatty alcohols.

In particular, lauric, myristic, oleic, linoleic, and linolenic acids appear to be most effective at inhibiting 5αR enzymes in the prostate, while linoleic, linolenic, and oleic acids seem most effective at inhibiting 5αR enzymes in the scalp. Therefore, increasing the overall free fatty acid levels in an LSESr enhances the quality, the absorption, and the localization of fatty acids to the prostate and scalp. Increasing the levels of certain free fatty acids should enhance the potency of the LSESr in specific tissues.

An LSESr that is more effective at inhibiting 5αR enzymes in the prostate should be more effective in maintaining normal urinary and prostate function in aging men than a standard extract. An LSESr that is more effective at inhibiting 5αR enzymes in the scalp should be more effective in promoting healthy hair growth in individuals susceptible to androgenic hair loss than a standard extract.

The preprocessing and milling help obtain a desired particle size and surface area where about 10% is less than about 4 mesh and about 95% less than about 12 mesh powder and help open up the matrix to optimize the free fatty acids as in the enhanced LSESr. Some prior art $CO_2$ extraction parameters operate at 100-350 bar, which has not been found adequate, especially since the process may be single step. Chemical transformation and alkyl hydrolysis has not been found beneficial since it may erode quality.

The enhanced LSESr of the current invention aids in balancing androgen signaling and controlling inflammation. The free fatty acid oleic acid has been found especially effective for 5α-Reductase-1, which is important for hair health, and not as much for 5α-Reductase-2, while linoleic free fatty acid has been found beneficial for both, which is beneficial for hair health treatment. Esterified fatty acids have been found ineffective. Linolenic acid has been found beneficial for both 5α-Reductase-1 and 5α-Reductase 2, and thus effective in hair health. The preprocessing of the saw palmetto berries into the saw palmetto powder helps open up the cell structure, and the aging, such as at least 15 days, and in an example, about 15 to 30 days of ageing, together with other factors, helps give the saw palmetto powder a beneficial moisture level, which aids during the $CO_2$ extraction and separation form the enhanced LSESr. There are positive benefits such as the enhanced LSESr aiding in stem cell signaling, which helps influence hair growth and the hair growth cycle.

For hair health, the inventors have discovered that linoleic and linolenic free fatty acids are beneficial and more active than previously understood by those skilled in the art. It is known that DHT may inhibit WnT signaling, which among the signaling molecules, promotes the differentiation of hair follicle stem cells. The enhanced LSESr helps block 5α-Reductase activity thereby reducing release of DHT that would otherwise inhibit WnT signaling, which plays a key role in simulating hair follicle stem cell regeneration.

An example of producing a LSESr which may be processed for an enhanced LSESr is now described. As shown in the flowchart, dried saw palmetto berries are supplied (Block 102), fed into a feed hopper (Block 104), and metallic particles and other magnetic particles or objects may be magnetically separated from the berries (Block 106). A hammer mill may be used to crush and mill the dried saw palmetto (Block 108). Cooling may be maintained to prevent excessive heating during milling by the application of liquid nitrogen to the hammer mill as a non-limiting example (Block 110). $CO_2$ extraction begins (Block 112) using carbon dioxide in an example (Block 114). Spent marc (Block 116) may include some organic residue and have some end use purposes, and thus, may be retained or discarded. $CO_2$ extraction includes a first fractionation (Block 118) and forming a first extract (Block 120), followed by a second fractionation (Block 122), and forming a second extract (Block 124), and a third fractionation (Block 126), and forming a third extract (Block 128), with recycling of the carbon dioxide (Block 114).

The method as described generally includes drying the berries, grinding the dried berries, extracting the berries with the $CO_2$ under relatively high pressure, and separating the extracted components from the $CO_2$. When ripe berries are harvested, they may contain about 66% water and may be dried for several days at 130-140° F. In the resulting dry state, the berries may be stored for several years without further deterioration. Dried berries may be bagged and shipped to processing facilities where they are ground to a fineness where about 100% are less than about 4 mesh and about 95% less than about 12 mesh into a fine powder.

Supercritical $CO_2$ fluid extraction may be accomplished in an extractor vessel by contacting the ground saw palmetto berries as a fine saw palmetto powder with a continuous flow of $CO_2$ at an extraction pressure of at least about 300 bar, and at a temperature lower than about 85° C. to thereby extract saw palmetto components from the $CO_2$. The process includes separating the extracted saw palmetto components from the $CO_2$ in a series of separator vessels by collecting the carbon dioxide after extraction and decreasing the pressure in a decreasing, stepwise manner.

In an example, the extraction vessel may be loaded with the ground, dried saw palmetto berries as a saw palmetto powder, and the $CO_2$ may be delivered into the vessel in a manner where the $CO_2$ flows through the loaded product before being discharged from the vessel. As the high-pressure $CO_2$ flows through the product, it behaves as a lipophilic solvent and extracts those saw palmetto lipidosterolic components that are soluble in the fluid. Different extraction pressures may be used, but it has been found that an extraction pressure of about 500-550 bar is advantageous. A first separation pressure may be about 250-300 bar, and may be about 160 bar to about 350 bar. Extraction may be conducted at a temperature from about 45° C. or 50° C. to about 90° C., and preferably under a substantially continuous flow of carbon dioxide. In an example, the first fractionation (Block 118 in FIG. 1) may be about 35° C. to about 85° C.

The method may include the second fractionation (Block 122 in FIG. 1) and associated separation having a separation pressure lower than the first separation pressure to separate a second fraction of dissolved components and compounds from the carbon dioxide. The second separation may include the fractionation as a separation pressure of about 50 to about 200 bar, and in another example, about 120 to about 150 bar. The temperature may range from about 20° C. to about 80° C.

Additionally, in accordance with another embodiment, the method may include a third fractionation (Block 126 in FIG. 1) and associated separation having a separation pressure lower than the second separation pressure to separate a third fraction of extracted compounds from the carbon dioxide. Sequentially, the $CO_2$ flows into a third separation vessel and the third fraction is collected. The third separation may include a separation pressure of about 30 to about 80 bar, and in another example, about 30 to about 60 bar, wherein the $CO_2$ is in the gaseous state. Following the last separation, the $CO_2$ is returned to storage for further use.

Plural separations may be conducted sequentially and in a substantially continuous flow. Each subsequent separation may have a lower predetermined separation pressure and operate as sequential separations referred to as cascading separations. Sequential separations separate the extracted saw palmetto compounds from the carbon dioxide into a plurality of fractions. Passing the substantially continuous flow of carbon dioxide after extraction through the different separations will separate the extract into several fractions.

In a preferred technique, each individual fraction of the resulting plurality of fractions may have a different fraction of extracted saw palmetto components from the other individual fractions. For example, the first fraction may include a major fraction of saw palmetto sterol and triacylglyceride compounds, the second fraction may include a fraction of saw palmetto components similar to a whole extract, and a third fraction may include a major fraction of saw palmetto unesterified, free fatty acids. This is contrasted where acylglyceride compounds include esters derived from glycerol and 1-3 fatty acids.

An advantageous benefit of the method as described is the ability to blend the resulting extraction fractions at predetermined amounts to prepare a dietary supplement composition that includes desired proportions of different saw palmetto components, including sterols, unesterified free fatty acids and fatty alcohols. This method allows not only the preparation of custom blends to meet specific consumer demands, but also the preparation of a dietary supplement composition that has been standardized for the final end use of the product.

The resulting dietary supplement composition may be formulated for oral use and nutritional supplementation. The composition may include a pharmaceutically acceptable carrier and may be orally administered as a gel capsule containing a unit dose. In an example, the daily dose may contain about 160 mg b.i.d. to about 320 mg, or at least about 200 mg of saw palmetto lipids as an enhanced lipidosterolic extract of *Serenoa repens*, (LSERs), and in another example, the unit dose may contain about 320 mg of saw palmetto lipids as enhanced effectiveness from LSERs for a single daily unit consumption.

A method for use may include ingesting the dietary supplement composition having at least about 85% saw palmetto fatty acids as the enhanced LSESr, and preferably greater than about 90% of these fatty acids present as free, unesterified fatty acids. The method for use may include ingesting the dietary supplement composition that has essentially no solvent residue. Ingesting may be accomplished by swallowing a capsule unit dose that includes a pharmaceutically acceptable carrier. A suggested daily dose may be about 320 mg of saw palmetto lipids as a LSESr, or about minimum 200 mg per dose of enhanced LSESr, preferably having a relatively high amount of unesterified fatty acids greater than about 72%.

An example of the production parameters and resulting extraction components from the extraction and isolation of the saw palmetto lipids based upon the process described relative to the flowchart in FIG. 1 is shown in Table 1. This table summarizes an example of the chemical composition of lipidosterolic extract of *Serenoa repens* (LSESr) created by the sequential separations as described above.

TABLE 1

| Parameter | 1st Separation Fraction | 2nd Separation Fraction | 3rd Separation Fraction | All Fractions Combined |
|---|---|---|---|---|
| Separation Pressure (bar) | 290 | 140 | 55 | — |
| Separation Temperature (° C.) | 60 | 70 | 25 | — |
| Fraction Mass (kg) | 11 | 701 | 74 | 786 |
| Acid Value (mg KOH/g) | 83 | 184 | 209 | 185 |
| Fatty Acid (% w/w) | | | | |
| Caproic | 0.6 | 1.2 | 2.1 | 1.3 |
| Caprylic | 0.9 | 2.1 | 3.3 | 2.2 |
| Capric | 1.1 | 2.6 | 3.4 | 2.7 |
| Lauric | 12.5 | 26.1 | 30.9 | 26.4 |
| Myristic | 5.7 | 10.6 | 11.2 | 10.6 |
| Palmitic | 5.7 | 8.8 | 8.2 | 8.7 |
| Palmitoleic | 0.1 | 0.2 | 0.2 | 0.2 |
| Stearic | 1.2 | 1.7 | 1.4 | 1.7 |
| Oleic | 22.7 | 32.8 | 28.1 | 32.2 |
| Linoleic | 3.0 | 4.6 | 3.7 | 4.5 |
| Linolenic | 0.7 | 0.5 | 0.4 | 0.5 |
| Total Fatty Acids | 54 | 91 | 93 | 91 |
| Percent as Free Fatty Acids | 62 | 85 | 90 | 85 |
| | 0.029 | 0.010 | 0.006 | 0.010 |
| Sterols (% w/w) | | | | |
| Stigmastanol | | | | |
| Campesterol | 0.122 | 0.055 | 0.036 | 0.054 |
| Beta-Sitosterol | 0.398 | 0.166 | 0.107 | 0.164 |
| Stigmastanol | 0.054 | 0.025 | 0.017 | 0.025 |
| Total Sterols | 0.603 | 0.256 | 0.166 | 0.252 |
| Long-Chain Alcohols (% w/w) | | | | |
| Tetracosanol | 0.011 | 0.003 | 0.002 | 0.003 |
| Hexacosanol | 0.036 | 0.017 | 0.010 | 0.017 |
| Octacosanol | 0.245 | 0.162 | 0.087 | 0.156 |
| Triacontanol | 0.048 | 0.031 | 0.016 | 0.030 |
| Total Alcohols | 0.340 | 0.213 | 0.115 | 0.206 |

During the supercritical carbon dioxide fluid extraction, it may be possible to use entrainers as cosolvents, although this is not necessary to obtain the desired LSESr. It is also possible to modify the phase behavior of supercritical solvents and enhance solubility of the components in the carbon dioxide-rich phase. A cosolvent may alter the polarity, viscosity and density of any gas phases. It may be possible to use cosolvents such as alcohols and hydrocarbons (straight-chained and branched) that may have a higher molecular weight. It may be possible to use ethoxylated compounds.

The enhanced lipidosterolic extract of *Serenoa repens* (LSESr) as manufactured and described may be formulated for prostate health or hair health, including addressing androgenic hair loss. The enhanced LSESr has been shown to inhibit 5α-Reductase 1 and 2. The enhanced LSESr may specifically target prostate tissue, reduce urinary frequency, and support, maintain and promote healthy urinary and prostate function. The enhanced LSESr may support optimal urinary flow and control in men and inhibit 5α-reductase without sexual side effects.

This enhanced lipidosterolic extract of *Serenoa repens* may be formulated for hair health treatment and regrowth because the enhanced LSESr has been found to target 5α-Reductase 1 and 5α-Reductase 2, which are found in hair follicles and affect hair regrowth and thickness.

The enhanced LSESr has a high percentage of free fatty acids not commonly found in nature. The enhanced LSESr has markedly different characteristics with a marked change in function and activity to treat symptoms of prostate disorder and promote urinary and prostate function, or for hair loss in a patient to promote prostate health and hair regrowth. The different free fatty acids as fractions alone or in combination provides a marked change in function and activity compared to what is normally found in nature. These benefits are accomplished via the plurality of separations and resulting manufacture of several fractions.

The enhanced lipidosterolic extract of *Serenoa repens* (LSESr) as manufactured and described may be encapsulated in a gelatin, carrageenan or starch based soft gel for oral consumption. The enhanced LSESr may be combined with dry excipients including, but not limited to one or more of silicon dioxide, calcium silicate, calcium phosphate, magnesium oxide, magnesium carbonate, calcium carbonate, rice fiber, and maltodextrin to create a free-flowing powder form of the extract. The enhanced LSESr may also be combined with excipients and spray dried into a free-flowing powder. The enhanced LSESr may also be combined with water and emulsified using excipients to create a stable emulsion, which may be dried such as by spray drying, belt drying, vacuum drying, or freeze drying to create a powder form.

The different carriers and formulations may also impart markedly different characteristics for the enhanced LSESr to stabilize the composition and impart functions that are significantly more in function than found in nature, and help in bioavailability of the composition that includes the enhanced LSESr when orally digested. It is possible to use a carrier for contacting the skin to help reduce acne.

Other additives may be included with the enhanced LSESr and may include pumpkin seed, Vitamin D, zinc, and rosemary oil, alone or in different combinations. The enhanced LSESr has been found to be stable and not require added antioxidants and has extended shelf life. Other additives may be included, such as Valensa's O2B® Peroxidation Blocker stabilization technology and other components, including astaxanthin, phenolic additives, and natural and synthetic tocopherols and tocotrienols, carnosic acid or carnosol and/or astaxanthin, but even without these additives, the enhanced LSESr has an extended shelf life as noted before.

Other additives with the enhanced LSESr may include a mixture of selected lipophilic and hydrophilic components. Lipophilic additives may be used either alone or in combination with at least one of: a) phenolic additives including at least one of sage, oregano, and rosemary; b) tocopherol(s); c) tocotrienol(s); d) carotenoids including at least one of astaxanthin, lutein, and zeaxanthin; e) ascorbyl acetate; f) ascorbyl palmitate; g) Butylated hydroxytoluene (BHT); h) Butylated hydroxyanisole (BRA); or i) Tertiary Butyl hydroquinone (TBHQ). A hydrophilic additive may include a sequestrant and may include hydrophilic phenolic additives including at least one of grape seed extract, tea extracts, ascorbic acid, citric acid, tartaric acid, and malic acid.

The process for manufacturing the enhanced LSESr as described above, such as with reference to the flowchart of FIG. 1, may be modified, such as shown in the sequence described at FIG. 55, to break out different fatty acids and free fatty acids that are important to promote urinary and prostate functions in men with an enlarged prostate, and enhance and maintain hair health and growth and reduce androgenic loss in a susceptible individuals. It is possible that humans or animals may consume the enhanced LSESr to be treated.

An example of the enhanced LSESr is shown in the table of FIG. 4A and Experiments 5 and 6 as Lot Nos. 211022 and 211105 and a secondary enhanced LSESr as Lot No. 210908, but having a lower ratio of four active free fatty acids. For example, some fatty acids play a more important role as more active free fatty acids in enzyme inhibition, such as 5αR-1 and 5αR-2 enzymes. The inventors have discovered that there are four free fatty acids that have greater influence and activity in the enhanced lipidosterolic extract of *Serenoa repens* (LSESr), and recognize these more important and active free fatty acids as lauric, myristic, oleic, and linoleic free fatty acids, and a fifth as linolenic free fatty acid that may be enhanced even more for hair health. These five key active free fatty acids aid in prostate health, hair growth, and skin, e.g., acne prevention. Of these five free fatty acids, some skilled in the art consider linolenic to be of reduced importance, but the inventors have discovered the beneficial aspects of linolenic acid as a free fatty acid to aid in inhibiting both 5α-Reductase Type 1 and Type 2 and help in hair growth, especially in combination with the free fatty acid linoleic acid.

FIGS. 2 and 3 are tables that respectively show the total 5α-reductase 50% inhibition ($IC_{50}$ μg/ml) of the 5α-R1 and 5α-R2 enzymes to convert testosterone to DHT by various constituents found in saw palmetto extract (FIG. 2), and the magnitude of the effect by the various constituents on a comparative basis (FIG. 3). The different free fatty acids of medium and long saturated chains and long unsaturated chains are shown, together with esterified fatty acids, oxidized fatty acids, fatty alcohols, phytosterols, and other components. The magnitude of the activity is designated by "none," "moderate" or "very active" (FIG. 3). The various constituents shown in the table of FIG. 2 are also shown and listed as free fatty acid molecules with: a) medium, saturated chains, b) long, saturated chains, and c) long unsaturated chains. There are esterified fatty acids, oxidized fatty acids, and fatty alcohols. These tables support other evidence that the five active free fatty acids for prostate and hair health are lauric, myristic, oleic, linoleic and linolenic free fatty acids.

The major contributors of active fatty acids unique to the enhanced LSESr are largely free fatty acids. The free fatty acids in the enhanced LSESr are uniquely intensified compared to other forms of fatty acids found in other sources. Vegetable oils contain fatty acids primarily in the triglyceride form, whereas LSESr contain primarily free fatty acids. In addition, LSESr contain high levels of lauric acid. Most vegetable oils, with the exception of coconut oil, typically do not contain lauric acid.

It is known that free fatty acids, such as derived from fish oil, are better absorbed and more bioavailable than corresponding triacylglycerides or ethyl esters that may be found in fish and similar oils. For example, absorption may occur at greater than 95% for the free fatty acids, versus 57% to 68% for the triacylglycerides, or versus 20% to 21% for the ethyl esters, respectively. There are some saw palmetto extracts that have high levels of free fatty acids, while other saw palmetto extracts have lower levels of free fatty acids. For example, depending on the type of extraction technique applied to saw palmetto berries or ground saw palmetto, the levels of free fatty acids in saw palmetto extracts may vary from 40% to 80%, but typically never beyond 80% even with supercritical $CO_2$ extraction. Saw palmetto extracts can be expensive to produce, and for that reason, there are known vegetable oils that are commonly used to adulterate or imitate saw palmetto extracts, but these oils contain high levels of triglycerides. Those saw palmetto extracts having higher free fatty acid concentrations are better absorbed and made more bioavailable than saw palmetto extracts having lower levels of free fatty acids and vegetable oil comparators. Once absorbed in the body, some free fatty acids specifically target the prostate, or the scalp to aid in hair health and hair growth.

There are some factors making free fatty acids undesirable in vegetable oils, even though they are made more bioavailable when ingested, for example. Free fatty acids are highly reactive and may create stability issues, and vegetable oils may degrade quickly. For example, heat and frying may degrade vegetable oils, and thus, quality is monitored by testing peroxide value as a measure of oxidative degradation.

This issue of oxidative degradation is not as challenging with saw palmetto extracts because the oil extracted from the saw palmetto is acidic, unlike vegetable oils, which has a more neutral pH. This benefit has been realized by the inventors with the enhanced LSESr of the invention. For example, the enhanced LSESr has a four-year shelf life that is a technical achievement for an oil that is high in free fatty acids, and especially with the higher ratio of free fatty acids to total fatty acids. This higher ratio of free fatty acids to total fatty acids and especially the contribution of four free fatty acids of lauric, myristic, oleic and linoleic was accomplished by the unique preprocessing of saw palmetto berries in combination with the unique supercritical $CO_2$ processing parameters. It is feasible to achieve high free fatty acid oil concentrations with an acidic pH, and this benefit of higher concentration is aided because the saw palmetto berries act as a natural oil protection, while excluding oxygen, without having to artificially stabilize the free fatty acids. For example, in an example of the enhanced LSESr, the peroxide value (PV) specification is below 5.0 meq/kg, and is below 1.0, so oxidative damage is controlled as well.

Based on a lipid chemistry perspective, the higher the free fatty acids are driven, the more likely there will be stability issues encountered. However, in accordance with a non-limiting example of the invention, the preprocessing of saw palmetto berries as described with the improved supercritical $CO_2$ extraction and enhanced processing parameters, the stability issue because a more minor issue because the supercritical $CO_2$ extraction process is a closed system in the absence of oxygen and used without organic solvents, such as hexane. This may be distinguished with a known commercial extraction with the organic solvent hexane as used to manufacture the commercially available European extract known as Permixon® with its attendant technical drawbacks as explained below.

Enhanced processing parameters for supercritical carbon dioxide extraction is employed when manufacturing the enhanced LSESr of the current invention rather than hexane, and this permits the process to achieve a stable extract which is "naturally/non-organic solvent" stable. Together with unique preprocessing of the saw palmetto berries, the enhanced LSESr is produced. Thus, any composition that includes the enhanced LSESr achieves a balanced fatty acid profile that is rich in free fatty acids, room temperature stable and stable for years.

Referring now to the tables shown in FIGS. 4A and 4B, and the graphs and bar charts of FIGS. 5 and 6, and Inhibition Experiment 1 (FIG. 5) and Inhibition Experiment 2 (FIG. 6), the inhibition of 5α-Reductase 2 is shown, which is the primary 5α-Reductase isoenzyme active in prostate tissue. The tables of FIGS. 4A and 4B show the results for a lipid profile comparison of a commercially available hexane extract Permixon®, and six further experiments of supercritical $CO_2$ extraction with varying parameters. Experiments 1, 5 and 6 had similar preprocessing of berries, but Experiment 1 used a low-pressure $CO_2$ extraction process typically used for extraction of hops. This lower pressure extraction extracted fewer mono- and diglycerides and unsaponifiable matter than the unique high pressure $CO_2$ extraction process such as with Experiments 5 and 6.

The conclusions for the biological assay are shown in FIG. 4B, which indicate that Experiments 5 and 6 as Lot Nos. 211022 and 211105 produce the enhanced LSESr and has the better profile to achieve the desirable range and percentage of total fatty acids and the better proportion of free fatty acids with their proper balance, ratio and enrichment of selected free fatty acids as lauric, myristic, oleic and linoleic free fatty acids. Their percentage was greater than 82.0%. Experiment 4 is a secondary enhanced LSESr with the lower ratio of the four active free fatty acids, but was still found to be effective, but not as much as the LSESr from Experiments 5 and 6.

If the concentration of free fatty acids is too high, it may be more difficult to obtain enough enrichment in the four important fatty acids that drive biological activity, i.e., lauric, myristic, oleic, and linoleic free fatty acids. For that reason, one goal was to achieve the range of about 82.0% to about 84.0% for these four bioactive free fatty acids. This can range from about 82.0% to as high as 86.0%, but preferably about 82.0% to about 84.0%. The better optimization comes from supercritical $CO_2$ extraction control and balance, such as described with reference to the process shown and described relative for the process shown in FIG. 55, that can be achieved with the right enrichment. In an example, the enhanced LSESr may have a balance of about 90.0%, and in a specific example, about 88.9% to about 90.2% of total fatty acids to about 72.0%, and in a specific example, about 72.4% to about 72.6% of free fatty acids. The enhanced LSESr had a ratio of free fatty acids to total fatty acids of about 80.0% to about 82.0%.

Experiment 1 as U4868 was a lower pressure and temperature extraction process such as typically used for extraction of hops products, e.g., around 150 bar and 40° C. The Experiment 1 low pressure process had quality issues by not removing all components, such as the mono and diglycerides and unsaponifiable matter. Although it may develop a ratio of free fatty acids to total fatty acids greater than the commercially available Permixon® and even some fatty acid ratios similar to the enhanced LSESr of Experiments 5 and 6, the lower pressure process produced an extract product differing from the invention in Experiments 5 and 6. The greater than 80% ratio of free fatty acids to total fatty acids and higher percentage of the four active free fatty acids was achieved for the enhanced LSESr shown by Experiments 5 and 6 as Lot Nos. 211022 and 211105, and had excellent shelf stability and as much as 4 years stability without added antioxidants and stabilizers. This was also achieved by the enhanced berry preprocessing with aging of the cryogenically milled saw palmetto berries and the $CO_2$ extraction parameters as later described.

Experiment 3 had similar $CO_2$ extraction processing parameters with slight differences, but no enhanced preprocessing of berries with specific cryogenic milling and aging of saw palmetto powder as with Experiments 5 and 6. Thus from those test results, it was evident that biological activity for the LSESr of Experiments 5 and 6 was not driven by simple factors of total fatty acids, free fatty acids, or the level of the important fatty acids as free fatty acids. The better profile of the enhanced LSESr was driven by the more desirable and inventive pre-extraction handling parameters described below and the inventive supercritical $CO_2$ extraction and separation parameters on the ripe berries, such as described relative to the flowchart of FIG. 55, to achieve: 1) a higher ratio of delivered free fatty acids to total fatty acids, which also aids in inflammation reduction; and 2) at the same time, a higher enrichment of the four important fatty acids as free fatty acids to total free fatty acids, which value is higher than the other compared products, including the commercially available Permixon®. The product obtained from Experiment 1 as the extracted product from the low-pressure process (U4868) has a lower ratio of the four beneficial free fatty acids compared to the enhanced LSESr of greater than 82.0%.

Comparing the percentages across the different lots, the total fatty acids is less important than the ratio of total fatty acids to free fatty acids. What is also important is the optimization of the contribution of the four bioactive fatty acids (lauric, myristic, oleic, and linoleic) as a percentage of total free fatty acids. These beneficial values in the enhanced LSESr are driven by the inventive preprocessing parameters for the saw palmetto berry and supercritical $CO_2$ extraction parameters. A fifth bioactive free fatty acid, linolenic, also contributes especially for hair health and operates to help reduce inflammation and aid signaling. It is possible to achieve a similar percentage of free fatty acids to total fatty acids from proportionally lower total fatty acids or higher free fatty acids. For example, Experiment 1 as the low pressure process (U4868) delivered more of these total free fatty acids at 87.0% and the contribution of free fatty acids to total fatty acids at a higher 94%, but less than 82.0% for the active four free fatty acids as in Experiments 5 and 6.

The aging, milling, and particle size deliver the optimum ratio of 4 (four) critical free fatty acids to total fatty acids via the supercritical $CO_2$ extraction. The invention and optimized aging/moisture, particle size and extraction parameters drive the value of the four active free fatty acids to total free fatty acids, not dependent on achieving highest total fatty acids or free fatty acids. The preconditioning of the berries allows the extraction process to achieve the inherently beneficial profile.

The 5α-Reductase Type 2 50% ($IC_{50}$) inhibition data are evident in the graphs and bar charts of FIGS. 5 and 6 for the two 5α-Reductase 2 Inhibition experiments, which compared Experiment 2 (U4602) as a more conventional $CO_2$ extract for an LSESr to inhibit 5α-Reductase 2 versus commercially available Permixon®, and the saw palmetto extract as Experiment 1 (U4868) corresponding to the low pressure. Data are shown in the graphs and bar charts of FIGS. 5 and 6 where data are reported as the effectiveness to inhibit enzyme activity ($IC_{50}$). Inhibition Experiment 2 (FIG. 6) examined the possible impact of the commercially available Permixon® product formulated on a pegylated (PEG) base or matrix with the conventional $CO_2$ extracted product in Experiment 2 that had been also formulated with polyethylene glycol (U4602-PEG).

In Inhibition Experiment 1 (FIG. 5), it should be understood that the use of the extract from Experiment 2 (4602-1) was a high-pressure supercritical $CO_2$ extract and the extract derived from a modified supercritical $CO_2$ extraction in Experiment 1 was produced at a lower extractor temperature and pressure, but used berries that had been preprocessed in a similar manner as used to produce the enhanced LSESr of the current invention and described below. Even though there was a lower ratio of the four active free fatty acids, it did have a high contribution of free fatty acids to total fatty acids of about 94.0%, but that did not make up for effectiveness. The Permixon® product was a hexane saw palmetto extract sold as a commercial product on a pegylated matrix as indicated. At concentrations of about 1.0 to 70 μg/ml, it is evident that the supercritical $CO_2$ extracts have greater percentage of inhibition than the commercially available hexane extract preparation, Permixon®, but at above 70 μg/ml, the percentage inhibition is about the same for all three saw palmetto extracts.

Inhibition Experiment 2 shown in FIG. 6 determined the possible impact of Permixon® product matrix (PEG) on an in vitro assay and the pegylated and conventional ultra-high purity supercritical $CO_2$ extract having the PEG matrix (U4602-PEG) was compared to the commercially available Permixon® and the conventional unpegylated product (U4602) for their ability to inhibit the 5α-Reductase 2 enzyme. The differences in inhibition were not as pronounced as compared to the samples of FIG. 5, indicating that the PEG matrix has an effect.

Lipid extracts manufactured using conventional techniques such as hexane extraction (Permixon®) or ethanol extraction (SABALSELECT®) from ripe saw palmetto berries typically contain over about ca. 70% free fatty acids. The experiments and studies show that ripe saw palmetto berries that have been preprocessed using techniques of milling and grinding as developed by the inventors and coupled with selected $CO_2$ extraction and separation pressures and temperatures as developed by the inventors may be employed to optimize the free fatty acids, which has been found to be a key to effectiveness, such as accomplished with the enhanced LSESr of Experiments 5 and 6 as Lot Nos. 211022 and 211105. Both the total and free fatty acids are important, but the higher level of free fatty acids and especially the four bioactive free fatty acids of lauric, myristic, oleic and linoleic are more biologically more relevant. Experiments have also shown that only certain types of fatty acids inhibit 5α-Reductase isoenzymes Type 1 and Type 2, such as the four primary more bioactive free fatty acids of lauric, myristic, oleic, and linoleic acids, and with a fifth as linolenic free fatty acid in combination with linoleic acid, and each of the free fatty acids having a different effect whether it is 5α-Reductase Type 1 or Type 2 enzyme.

Linolenic acid has been found advantageous for hair health in combination with linoleic acid as free fatty acids and inhibiting 5α-Reductase Type 1 enzyme and as an aid in signaling. These free fatty acids are believed to act synergistically in inhibiting 5α-Reductase both Type 1 and Type 2. The overall lipid profile of the enhanced LSESr confirms authenticity. By establishing pre-extraction processing parameters of ripe berries, together with the production parameters for supercritical $CO_2$ extraction, it is possible to ensure that the desired free fatty acid concentrations and ratios, especially with the four bioactive free fatty acids, are met to form the enhanced LSESr. Thus, a quality product may be produced such as the enhanced LSESr. Biological assays will not be required for every production lot since the repeated use of the preprocessing parameters of the saw palmetto berries and the specific supercritical $CO_2$ extraction parameters will repeatedly produce the enhanced LSESr having a ratio of free fatty acids to total fatty acids that is greater than about 80.0% and an enrichment of lauric, myristic, oleic and linoleic free fatty acids that is greater than about 82.0%.

In an example, this enhanced LSESr may have a balance of about 90.0% of total fatty acids to about 72.0% of free fatty acids, and an enrichment of the four active free fatty acids of about 82.0% to about 84.0%. It has been found the ratio of free fatty acids to total fatty acids of about 80.0% to about 82.0% is effective with about 82.0% to about 84.0% of the four bioactive free fatty acids.

The fatty acids in the LSESr target the prostate. The 5α-Reductase enzymes are found in several different tissues in the body. However, the free fatty acids in the enhanced LSESr target the prostate cells, and unlike most cells in the body, the prostate cells preferentially uptake these free fatty acids instead of glucose. The androgen receptors up regulate fatty acid transporters on the surface of prostate cells.

It has been found that there is a difference in function between Finasteride as a 5α-Reductase inhibitor and the enhanced LSESr bioactive free fatty acids. Finasteride permanently locks the enzyme closed, and competitively blocks the binding sites. The enhanced LSESr bioactive free fatty acids, on the other hand, temporarily change the make-up of the nuclear membrane, which disrupts the stability of the enzyme, and non-competitively blocks the binding sites. This is one reason why the type, quantity and ratio of the free fatty acids relative to fatty acids can be important and slight variations, such as found with the enhanced LSESr of the invention as compared to other $CO_2$ extracted products or Permixon® or other hexane extracted saw palmetto extracts can have such a positive difference in function.

By specifically targeting prostate cells, the enhanced LSESr has no effect on circulating DHT (Dihydrotestosterone) levels and has low side effects, including low sexual side effects. The free fatty acids in the enhanced LSESr change the lipid composition of the nuclear membrane, which disrupts 5α-Reductase activity. The impact on the 5α-Reductase enzymes is reversible and non-competitive, while the biological function of the 5α-Reductase enzyme is conserved. These effects are not seen with vegetable oils or saw palmetto imitators because these oils have the wrong forms of fatty acids and free fatty acids, the wrong ratios, and the wrong lipid profile. Powdered saw palmetto products are very common, but they do not have enough lipid content, and often have an inferior level and type of fatty acids.

The free fatty acids are inserted into the prostate cell nuclear membrane and impact functionality of that cell nuclear membrane, disrupt 5α-Reductase enzyme activity, lead to no further or limited enlargement of the prostate, lead to less inflammation with a resultant improvement in urinary flow and control, and no delayed progression of the condition. Small changes in amounts, ratios and specific free fatty acids make large differences as the inventors have determined, such as with the four bioactive free fatty acids, enabling peak results for the enhanced LSESr. The free fatty acids of the enhanced LSESr operate as active ingredients for clinically proven anti-inflammatory and anti-proliferative effects, which are likely due to reduced inflammatory enzyme activity such as 5-lipoxygenase, COX-2, Phospholipase $A_2$, and similar enzymes via disruption of the cell nuclear membrane. The inhibition of the NF-kB activation reduces inflammatory gene expression.

These effects and functions can be explained when comparing a balanced immune system and an unbalanced immune system. For example, a balanced immune system responds to triggers such as an infection or injury and activates pro-inflammatory enzymes and pro-inflammatory mediators to deal with the threat. A balanced immune system also resolves inflammation after the threat has been neutralized, which promotes healing of tissues by increasing production of growth factors. An unbalanced immune system, on the other hand, does not resolve inflammation, even after the threat is no longer present. An unbalanced immune system may have an uncontrolled activation of pro-inflammatory mediators, which leads to tissue damage and dysregulates production of growth factors, resulting in abnormal cell proliferation and tissue remodeling. Hypoxemia may occur from rampant cell growth that leads to angiogenesis and production of more growth factors.

The enhanced LSESr of the current invention disrupts the activity of pro-inflammatory enzymes and the expression of inflammatory genes. Similar to 5α-Reductase, the enhanced LSESr changes the composition of the cell nuclear membrane, which disrupts the activity of pro-inflammatory enzymes. By blocking activation of NF-kB, the enhanced LSESr reduces the expression of numerous inflammatory mediators such as pro-inflammatory enzymes, adhesion molecules, cytokines, chemokines, growth factors, receptors, and transcription factors.

It is understood that the fatty acid transporters on prostate cells preferentially take up the free fatty acids instead of glucose, unlike most cells in the body. Thus, the free fatty acids of the enhanced LSESr inhibit the 5α-Reductase and are anti-inflammatory. The enhanced LSESr of the current invention is rich in free fatty acids and their specific combination and ratio. An example is the enhanced LSESr of Experiments 5 and 6 (FIG. 4A), which is able to support prostate and urinary health by restoring balance in the androgen signaling such as caused by the static obstruction and DHT mediated prostate enlargement, and address inflammatory pathways in the prostate. The enhanced LSESr of the current invention has a sexual side effect level similar to baseline or placebos used in other trials. Concerning possible drug-drug interactions, the enhanced LSESr of the current invention does not appear to affect the majority of the cytochrome P450 isoenzymes and does not interfere with PSA antigen testing. The enhanced LSESr does not reduce the secretion of PSA, even in long-term studies.

Reference is made again to FIGS. 4A, 4B, 5 and 6 and the discussion of Inhibition Experiments 1 and 2. In Inhibition Experiment 1 (FIG. 5), two $CO_2$ extraction procedures were employed, i.e., one using the lower pressure $CO_2$ extraction (U4868) as Experiment 1 in FIG. 4A and a conventional $CO_2$ extraction of Experiment 2 in FIG. 4A (U4602) and compared to Permixon®, and studied for the inhibition of 5α-Reductase Type 2 enzyme as primarily reflected in prostate tissue. It is believed that the difference in inhibition rates may be due to the presence of the polyethylene glycol (PEG) in the Permixon® formulation, which may bind to the free fatty acids and subsequently reduce the amount that can be extracted in test samples.

Inhibition Experiment 2 (FIG. 6) further showed the differences between conventional supercritical $CO_2$ saw palmetto extracts complexed with PEG versus that saw palmetto without PEG where the pegylated sample (U4602_PEG) was generated. The pegylated sample had an $IC_{50}$ of 7.47+/−0.07 micrograms per milliliter (μg/ml), similar to the $IC_{50}$ of 7.72+/−0.05 μg/ml for the commercially available hexane extracted Permixon®, where the p-value was not significant. The unpegylated sample (U4602-1) had an $IC_{50}$ of 4.54+/−0.23 μg/ml with a p-value less than 0.0001 compared to each. These results show the beneficial aspects of a supercritical $CO_2$ extract over conventional hexane extraction, such as the commercially available Permixon.

It should be understood that the enhanced LSESr is also beneficial for hair treatment of androgenic hair loss and reduces inflammation and aids in stem cell signaling. Hair growth and loss is a natural occurrence with the growth phase referred to as Anagen where the follicles are anchored at the base. This stage occurs for about 2-6 years duration and about 90% to about 95% of the follicles are at this stage of the hair growth cycle. The transition phase (Catagen) is about 2-3 weeks and less than 1% of hair follicles are at that stage. In this Catagen stage, the hair follicles slowly detach from nourishing blood supply and stop growing. The resting phase known as Telogen is about 2-3 months and about 5% to 10% of follicles are in this stage, where there is no nourishment and the hair dies and falls out. The early Anagen phase follows where the hair follicle re-establishes and hair regrowth begins. The duration of the growth phase imparts hair length and can be 2-6 years in duration. Blood flow provides nourishment that enables growth.

When the hair growth cycle is impacted, the result is hair thinning and resultant shorter and finer hair follicles over time, such as occurs with miniaturization and alopecia. Thus, any hair loss remedy must balance the cycle of growth, loss, and the resting phase before growth begins again. Humans are typically born with all hair follicles, e.g., about 100,000 on the scalp. More hair follicles are not produced, but hair growth and hair health can be supported.

Androgens are considered the main regulators of the hair follicle. Normal hair growth cycle takes place in the presence of androgens. However, androgens may inhibit hair follicle growth in genetically susceptible individuals, leading to small, thin hair and hair loss, also known as Androgenic Alopecia (AGA). Usually AGA is a hereditary thinning of the hair induced by androgens and may begin between the ages of 12 and 40 in both sexes, but it is less severe in women due to the lower levels of androgens.

There is an interplay between androgens and the androgen receptor and the hair follicle. Androgens from the blood, such as circulating testosterone, may enter the hair follicle via the dermal papilla's blood supply and may be converted by 5α-Reductase to the more potent androgen DHT, which may bind to the androgen receptors in the dermal papilla cells, causing changes in their production of regulatory paracrine factors. This directly alters the activity of dermal papilla cells. Keratinocytes and melanocytes may also be affected. The complex then binds to elements in the DNA, altering the expression of specific androgen-dependent genes.

If both testosterone and DHT are present in similar quantities, the androgen receptor will bind 5α-dihydrotestosterone (DHT) rather than testosterone. Once the 5α-DHT complex is formed, the receptor complex undergoes conformational change. Along with co-activating proteins, the 5α-DHT complex binds to elements in the DNA, altering expression of specific androgen-dependent genes. The effect is the hormone-receptor complex-activated genes change large terminal follicles to miniaturized follicles. Each successive hair cycle undergoes a shorter growth phase and the follicles become smaller, producing shorter, finer hair that poorly covers the scalp.

Signaling is indicative that the hair follicle stem cells move from the resting phase and start the growth phase. DHT interferes with the signaling that begins the hair growth cycle and can activate expression of an important gene (DKK-1), a major hair loss factor secreted from dermal papilla (DP) cells that may induce and accelerate AGA. DHT up-regulates Catagen inducers, and the dermal papilla cells produce DKK-1 in response to DHT in the AGA scalp.

DKK-1 is a Catagen inducer and suppresses dermal papilla cells and keratinocyte proliferation and slows the differentiation of hair follicle stem cells. DHT also up-regulates the secretion of IL-6 and T6F-β1 by dermal papilla cells. This suppresses keratinocyte proliferation and inhibits hair shaft elongation. Scalp DKK-1 is much higher in individuals with AGA than evident with others serving as controls. Men have more 5α-Reductase enzymes and androgen receptors in the scalp than women, which leads to higher levels of DHT-AR complex and higher DKK-1 levels in scalps. For that reason, androgenic hair loss in men is more severe than for women.

The 5α-Reductase enzymes Type 1 and Type 2 are located within hair follicles, where they influence hair growth and hair miniaturization. The 5α-Reductase Type 1 enzyme is almost everywhere, while the 5α-Reductase Type 2 is very localized. 5α-Reductase 1 and 2 are present in higher levels in women with female pattern hair loss and the 5α-Reductase inhibitor therapy has been shown to be effective in men with androgenic hair loss. The hair structure includes different components. The inner root sheath anchors and protects the hair shaft and the outer root sheath surrounds the entire hair follicle and is a source of stem cells. The matrix cells generate hair and the papilla allow for vasculature for blood supply. The more localized 5α-Reductase Type 2 enzyme is not typically located in the outer root sheath and papilla. For this reason, the enhanced LSESr may affect 5α-Reductase Type 1 enzyme, and having enhanced linolenic and linoleic free fatty acids, may be better suited for hair health.

Saw palmetto extract of about 320 milligrams per day versus finasteride of 1 milligram per day had been studied in 100 men with mild to moderate androgenic alopecia to assess changing hair density over 24 months. Both treatments increased hair growth but finasteride was found more effective. The saw palmetto extract stabilized hair loss in 52% of men, and 38% of men treated with the saw palmetto extract had increased hair growth, and 68% of men treated with finasteride noted an improvement.

However, as is well known, finasteride comes with side effects not seen with saw palmetto extracts. Inhibiting the 5α-Reductase Type 1 enzyme helps limit the production of DHT and supports hair health. The graphs in FIG. 7A show a comparison between a control and female pattern hair loss (FPHL) and how the number of molecules of 5α-Reductase Type 1 enzyme increase with those having FHPL compared to a normal control as the left-hand graph, and the right-hand graph showing that 5α-Reductase Type 2 enzymes are also overexpressed in women with FPHL.

Reference is now made to FIGS. 7B and 7C showing the use of a supercritical $CO_2$ extracted LSESr and Permixon®. The inhibition of the 5α-Reductase Type 1 enzyme displayed in the graph and bar charts of FIG. 7B show the mean percent inhibition relative to concentration (μg/ml) and mean $IC_{50}$ (μg/ml) in the bar chart on the right. FIG. 7C is a graph and bar chart showing the inhibition of 5α-Reductase Type 2 enzyme for the supercritical $CO_2$ extract product as compared with Permixon®. These and other studies lead to the conclusion that a greater effect will be enabled from the enhanced LSESr, such as Experiments 5 and 6 (FIG. 4A), and will restore hair growth even more in AGA mouse models to block DHT effects to an even greater degree than conventional hexane extracts or conventional $CO_2$ extracted saw palmetto extracts.

The hair follicle includes lipids and especially fatty acids and free fatty acids. The highest concentration of lipids in human hair is about 4.3 mg/g of free fatty acids. For example, the medulla of the hair follicle includes squalene, triglycerides, cholesterol, wax esters, and free fatty acids such as oleic acid and palmitic acid. The cortex of the hair follicle includes integral fatty acids such as linoleic acid and alpha-linoleic acid and non-covalently attached fatty acids, triglycerides, cholesterol, wax esters, and squalene. The interface between the cortex and cuticle includes a lipid containing N-acetylglucosamine. The entire cuticle contains ceramides and cholesterol. An epicuticle includes 18-methyl eicosanoic acid (18-MEA) and an exocuticle includes free fatty acids and covalently-attached fatty acids. An endocuticle includes free fatty acids and covalently-attached fatty acids. Free fatty acids are common lipids in hair, mainly in the hair matrix cells.

Recent studies show that linoleic acid promotes hair growth in normal mice, and promotes the Anagen phase in normal shaved mice by up-regulating hair growth related proteins. After about 20 days, linoleic acid operated better than controls and equivalent to Minoxidil with about 100% hair growth.

Referring now to FIG. 7D, there is illustrated a bar chart showing the distribution of oral alpha-linolenic acid in guinea pigs. Linolenic acid was mainly distributed in the fur and skin at about 46% total, of which 54% was found in fur and 46% in skin. Over 70% of that lipid was found in the free fatty acid form. There were 16 times more linolenic acid in the fur and skin of the head than in the fur and skin of the rest of the body. The authors of the study by Fu et al. entitled, "Novel Pathway of Metabolism of α-Linolenic Acid in the Guinea Pig," Pediatric Research, 47, 414-417 (2000), assumed that linolenic acid was being secreted by the sebaceous glands in the skin onto the fur. However, the authors do not test this assumption. This study stresses that the preprocessing and $CO_2$ extraction parameters that enhance linoleic and linolenic free fatty acids and include the higher ratio of the four bioactive free fatty acids would be beneficial over conventional hexane or $CO_2$ extracts.

It is known that oral free fatty acids may be localized to the skin and hair follicles in addition to the prostate where the five alpha-reductase enzymes are located. The human hair contains a high percentage of fatty acids, mainly in the free fatty acid form. Thus, it is possible that some of the linolenic acid may have instead become incorporated into the fur of the guinea pigs. The enhanced benefit of the free fatty acid linolenic acid for hair health and hair growth is evident.

The enhanced LSESr of the current invention may also be used to reduce acne since there is localization of 5α-Reductase enzyme in inflammatory acne lesions and inhibition of 5α-Reductase has been shown to improve acne in men with androgenic hair loss. 5α-Reductase Type 1 enzymes are the predominant isotype in acne lesions and are localized in the sebaceous glands. 5α-Reductase Type 2 enzymes are the minor isotype in acne lesions and are localized to sebaceous duct and endothelial cells.

The enhanced LSESr of the current invention inhibits 5α-Reductase 1 and 2 enzymes that play an important role in androgenic hair thinning and eventually hair loss. The enhanced LSESr of the current invention interferes with DHT production in the scalp. The DHT impacts the hair growth cycle in genetically susceptible individuals, causing the hair follicle to miniaturize, which results in hair thinning and eventually hair loss. Thus, the enhanced LSESr of the current invention inhibits 5α-Reductase 1 and 2 enzymes that convert testosterone to DHT, and thus, supports a healthy hair growth cycle, hair health, and becomes an important active ingredient to be used for supplements that help inhibit thinning hair.

The enhanced LSESr of the current invention has a high ratio of free fatty acids to total fatty acids that is greater than about 80.0% and enrichment of lauric, myristic, oleic and linoleic free fatty acids greater than about 82.0%, and inhibits 5α-Reductase types 1 and 2 enzymes that play an important role in androgenic hair thinning and eventually hair loss. The enhanced LSESr of the current invention interferes with DHT production and reduces the amount of DHT that may accumulate in the scalp, and which impacts the hair growth cycle. DHT may accumulate in the scalp and impact the hair growth cycle, causing the hair follicle to miniaturize in genetically susceptible individuals and result in hair thinning and eventually hair loss. The enhanced LSESr of the current invention inhibits 5α-Reductase type 1 and type 2 enzymes that convert testosterone to DHT and supports a healthy hair growth cycle and hair health. The enhanced LSESr may be an important active ingredient added to dietary supplements for addressing thinning hair and helping to make hair thicker. The enhanced LSESr of the current invention has a higher ratio of free fatty acids to total fatty acids as shown by experiments and will support hair thickness and hair fullness, and operate as a natural and safe ingredient for hair health.

It is possible to add vitamin D with the enhanced LSESr of the current invention. The vitamin D receptor expressed in dermal papilla cells will maintain hair follicle homeostasis, and especially anagen initiation. The dermal papilla cells are an important site for DHT impact on hair. The vitamin D receptor in both serums and tissues are significantly different in adults with androgenic hair loss than other controls (p=0). An insufficient amount of vitamin D may mean that keratinocytes in hair follicles are not able to regulate hair growth and shedding. It is known that women with mild-to-moderate female pattern hair loss (FPHL) have significantly higher mean serum vitamin D levels than women with severe hair loss. The micro-inflammation that does not lead to scarring of the scalp has been evident in women with FPHL and may be related to the hair follicle miniaturization process.

There are also synergies using the enhanced LSESr of the current invention with zinc because it has been shown to increase the proportion of follicles in anagen, hair volume, and hair appearance in men with AGA. Zinc deficiency may reduce the efficacy of Minoxidil treatment in men with AGA. Zinc may inhibit DHT production by limiting production of NADPH, which is necessary for the function of 5α-Reductase enzymes. A combination topical lotion containing the enhanced LSESr of the current invention and an herbal supplement containing zinc may be 50% more effective than either alone in male and female AGA. Some studies have shown that treatment with a topical saw palmetto combination product for four weeks increased the average hair count and terminal hair count at 12 and 24 weeks in 50 men with androgenic alopecia. The enhanced LSESr of the current invention will provide greater enhancements.

It also possible to formulate the enhanced LSESr of the current invention with rosemary oil, and optionally in combination with 5% Minoxidil. This combination should be significantly better than Minoxidil alone and improve the mean hair diameter and hair mass. The enhanced LSESr of the current invention may be combined with one or more of vitamin D, zinc and rosemary oil to address androgenic-mediated hair thinning and loss, support hair growth and regrowth, and address micro-inflammation in the hair follicle in adults suffering from androgen-mediated hair loss. Zinc, which inhibits 5α-Reductase through a different mechanism of action than LSESr, may also act synergistically with the enhanced LSESr of the current invention to support hair follicle health, growth of new hair, hair volume and fullness, and overall hair health and appearance. The rosemary oil may act synergistically to support optimal hair growth in patients already using Minoxidil.

The enhanced LSESr of the current invention is produced using pre-extraction processing parameters for saw palmetto berries and specific processing parameters of ultra-high-pressure, supercritical $CO_2$ extraction, which creates a hexane-like extract but without the harsh organic chemicals. It is rich in the free fatty acids which have good bioavailability and are absorbed twice as well as triglycerides, and includes better localization to the site of activity, such as the scalp or prostate as compared to triglycerides.

There now follows a description of parameters associated with the preprocessing of ripe saw palmetto berries as pre-extraction parameters, which in combination with specific processing parameters in the supercritical $CO_2$ extraction, will produce the enhanced LSESr as in Experiments 5 and 6 in FIG. 4A. A regression model may be described on the reaction and interactions of the pre-extraction process for total free fatty acids, followed by a description of the supercritical $CO_2$ extraction process used in conjunction with the saw palmetto berry processing to produce the enhanced LSESr. Together the pre-extraction processing and processing parameters of the $CO_2$ extraction, such as described in the flowchart of FIG. 55, will obtain the beneficial ratio of free fatty acids to total fatty acids as in Experiments 5 and 6 (FIG. 4A), Lot Nos. 211022 and 211105. Free fatty acid consistency and maximization is achieved by preprocessing the ripe saw palmetto berries before the supercritical carbon dioxide extraction. A regression model may be established based on the reaction and interactions of the process to the total free fatty acids.

In an example, dried mature saw palmetto berries of less than about 12% to about 13% moisture, and preferably ranging from 10% to 12% moisture, were released for the production process by a batch reference number. The saw palmetto berries by batch were introduced to a cryogenic milling system to create a consistent fine powder. The cryogenic milling system included a control feeder, and in an example, a 50 horsepower chopper mill with ½ inch screen openings. Different horsepower ratings may be used depending on the type of machine. A cryogenic conveyor included a liquid nitrogen addition to create chopped berries at about −40° C. In an example, the temperature was no greater than −20° C. This range can vary as much as 10-20 degrees (F or C) above and below the −40° C. value.

Frozen material was dropped by gravity into a 50 horsepower pulverizing mill with a 3/16 inch screen opening. The feed rate was typically about 119+/−6 kilograms per hour (kg/hr) with a resulting mill amperage of about 4 amps, and an amperage range preferably of about 2.5 to 5.5 amps. The 50 horsepower chopper amperage had a similar amperage range and is in-line with the process at a consistent feed rate. The liquid nitrogen requirements were about 20+/−1 standard cubic feet (SCF) cryogenic nitrogen per kilogram of chopped and dried saw palmetto berries to achieve a recommended process temperature of feed into the mill on a continuous basis. This can vary by about 10% to 20% above and below these values.

The fine, milled saw palmetto powder about 100% less than about 4 mesh and about 95% less than about 12 mesh was fed into super sacks at about 600 to about 900 kilograms each on pallets. The entire lots once completed were stored by lot in a warehouse under hold, until aged to a target time. The aging was greater than about 15 days, and may preferably about 15 days to about 30 days, and in another example, be greater than 20 days, but not excessive such as beyond 40 day aging, and in an example, about 15 days to about 30 days for best results. The cryogenic milling followed by at least 15 days aging was found important with the $CO_2$ extraction parameters. The completed milled and aged saw palmetto powder by lot was released to an extraction and separation process.

Referring now to FIG. 8, there are shown a graph and chart of the cryogenic mill AC amperage used for the saw palmetto production, and showing a histogram of the density versus the AC current amperage. The density versus AC current curve is the amperage of the primary cryogenic mill in operation on frozen, chopped saw palmetto berries. A smaller occurrence of amperage greater than about 5.5 may be associated with a start-up of short duration, but it is not as important to product quality since 100% of material passes through a screen. Mill loading may be about 262.4+/−13.2 pounds per hour with a 50 horsepower motor or about 119+/−6 kilograms per hour with a 37.3 kilowatt (kw) motor. The chopper processing with ambient temperature saw palmetto berries has a similar loading rate on a 50 horsepower motor.

The aging impact on the free fatty acids (FFA) with fine milled berries as processed above was determined at a central Florida location having ambient warehouse conditions. An average temperature is shown in FIG. 9A for December through June, reflecting a typical average year for that time period, and showing the normal test temperature and the percent versus the temperature Fahrenheit. The graph in FIG. 9B shows the normal test relative humidity percent on the horizontal line and percentage on the vertical line.

Ambient aging conditions have an effect on the saw palmetto berries. Thus, various warehouse ambient conditions are important for the milled saw palmetto, and aging is appropriate prior to extraction. FIG. 10A is a table showing various months and the temperature in degrees Fahrenheit, and the months from December (12) to June (6) as an average cycle. The table shows the mean, standard error mean, standard deviation, the C variation, the median, the total remuneration (TR) for the mean, the minimum, the maximum, the range, and N as the population size. The temperature may range in this example from about 59° F. to 79° F. and in a wider range, about a minimum of 40° F. to maximum of about 87° F., and a mean of about 59° F. to about 78° for best results. FIG. 10B is a similar table as in FIG. 10A, but showing the percentage of relative humidity and showing a range from about 30% to about 97%, and a mean of about 67% to about 78% for best results.

The mature, dried, and milled saw palmetto berries that are aged are then extracted with the enhanced processing parameters. The scatter plot graph data shown in FIG. 11 represents the data for over 60 campaigns of 1200 MT dried berries or over 9 MM pounds of harvested berries. Free fatty acids versus fatty acids for the five actives of lauric, myristic, oleic, linoleic, and linolenic acids are shown as the scatter plot in FIG. 11 showing on the vertical axis the five actives FFA/FA versus the mill and hold time in days on the horizontal, and showing the relative flat line curve at about 20-35 days and the peak at about 28 days. Aging should occur at greater than 15 days, but it is evident that beyond 30 days in this example, the results and effectiveness were decreased slightly.

Referring now to FIGS. 12A and 12B, the statistics for the active five fatty acids and the active five free fatty acids that result from the processing of the dried saw palmetto berries relative to starting berry moisture are shown. In FIG. 12A, the bar chart for the key fatty acids and five active free fatty acids are shown when the starting berry moisture is below the desired specifications corresponding to less than 10% moisture. This bar chart also shows the graph line for the average of the five actives and ratio FFA/FA. In FIG. 12B, the bar chart shows the average of the five key fatty acids and free fatty acids similar to FIG. 12A when the starting berry moisture is in specification of about 10% to 12% moisture and showing the graph line similar to that shown in FIG. 12A for the average of five actives FFA/FA.

Referring now to FIG. 13, a series of graphs as scatter plots are shown that relate to the process conditions and parameters to resolve quality for the percentage of free fatty acids relative to fatty acids versus the time between harvest and extraction. The scatter plots are illustrated for the five active free fatty acids relative to fatty acids versus time between harvest and extraction. The graphs on the left show an average hold time between initial harvest and extraction via the supercritical $CO_2$ extraction of about 200 days. This includes the post-mill hold time. Thus berries are selected and dried, then ground and held for at least 15 days.

In FIG. 14, a line graph is shown for the analysis of the variance (ANOVA) for the percentage of free fatty acids/fatty acids on the five key fatty acids in the saw palmetto per the mill and hold time and showing an alpha ($\alpha$) of 0.05. The mean is shown on the vertical axis and brackets hold time on the horizontal axis. Less than 10 days is statistically significant with 95% less than average. A greater than 15 days hold time is statistically improved with a 95% confidence versus all hold times less than 15 days.

The hold time impact on the variance of the percentage of free fatty acids and the fatty acids are shown in the test results as a bracketed line of FIG. 15, showing a test for equal variances for the five actives of free fatty acids/fatty acids versus the brackets hold time. There are multiple intervals for the standard deviation of alpha ($\alpha$) equal to 0.05. The longer hold time greater than 10 days is statistically improved at a 95% confidence on the variance versus less than 10 days. The analysis of variance (ANOVA) for the specific five active fatty acids as lauric acid, myristic acid, oleic acid, linoleic acid, and linolenic acid are shown in the line graphs of FIGS. 16-20 respectively, and showing the brackets hold time in the horizontal axis and the mean in the vertical axis. In each graph, the specific acid is identified as a percentage of free fatty acid/fatty acid in the saw palmetto per mill and hold with alpha ($\alpha$)=0.05. The graph lines show the benefits of milling and holding as described above and with the better results at about 15 days and greater.

Different fatty acid statistical tables with ranges are shown in FIGS. 21-26. In FIG. 21, the statistics for the five active fatty acids identified above for prostate health are shown, followed by the statistical tables for lauric acid (FIG. 21), myristic acid (FIG. 22), oleic acid (FIG. 23), linoleic acid (FIG. 24), and linoleic acid (FIG. 26). The post mill hold time in days is illustrated with the values as in the tables of FIGS. 10A and 10B. The benefits of the longer hold time are evident with both the mean and median have the better values for all examples above 15 days. For example, in FIG. 21, the highest percentage of FFA/FA is 87.80% at greater than 15 days, post-hold time, which was used to obtain the advantageous results for the enhanced LSESr such as shown with Experiments 5 and 6 of FIG. 4A, giving the four major active FFA's greater than 82.0%, and close to that with Experiment 4.

This evidence also shows that the saw palmetto berries that are harvested and dried have various levels of fatty acids in a specific relationship to each other. The free fatty acid quality for the same fatty acids varies naturally over the season and region of harvest. By selecting specific berry preprocessing conditions and parameters and specific supercritical $CO_2$ extraction parameters, it is possible to maximize and standardize to a tight variance the individual free fatty acid levels and their ratio relative to fatty acids that are important for prostate health and hair health. These results also add insight into the interactions and reactions occurring with the fatty acids and free fatty acids as based on the processing parameters and the post mill hold time.

FIG. 27 is a graph showing the percentage of the actives for the free fatty acids/fatty acids versus the post mill hold time of the five active fatty acids as the lauric, myristic, oleic, linoleic, and linolenic fatty acids where alpha ($\alpha$)=0.05, and showing the benefits of hold times at about 15 days compared to a lesser hold time. The test for equal variances for the five actives as free fatty acids/fatty acids versus the brackets hold time is shown in the bracket line graph of FIG. 28 where the lower standard deviation bracket is better. When the brackets do not overlap with other conditions than statistically different at 95% confidence, it is evident that the longer hold time of post-milling of about 15 days is better. There are multiple comparison intervals for the standard deviation or alpha ($\alpha$) when it is equal to 0.05. Multiple comparisons are shown where the p-value is equal to 0.024 and Leverne's test has a p-value of 0.005.

Figure 29:
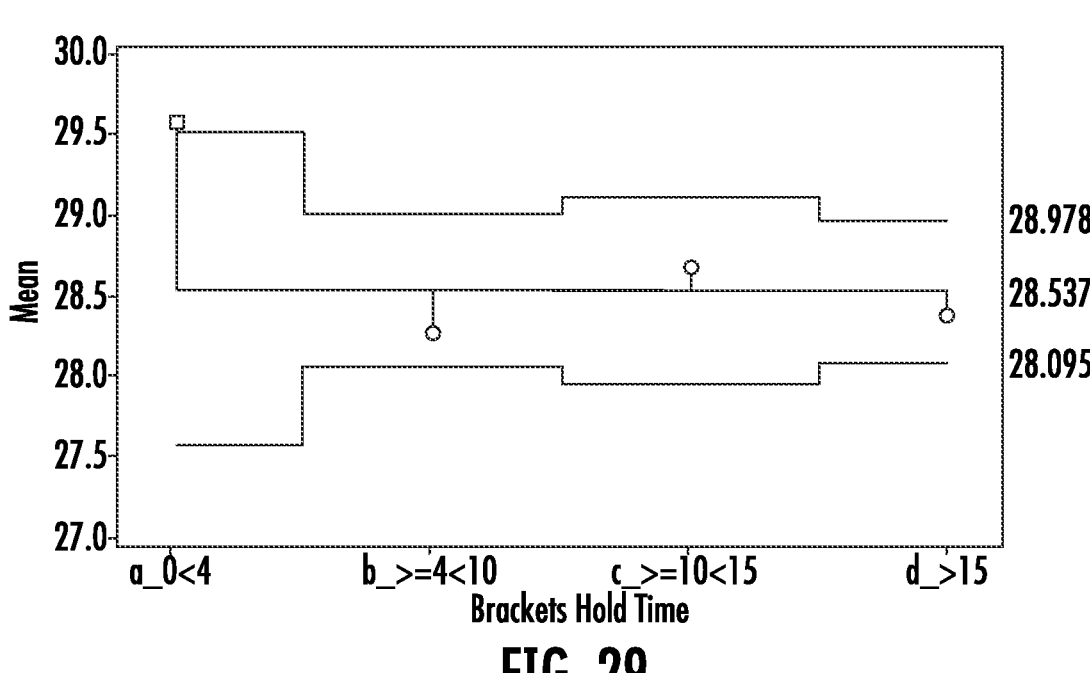
Figure 30:
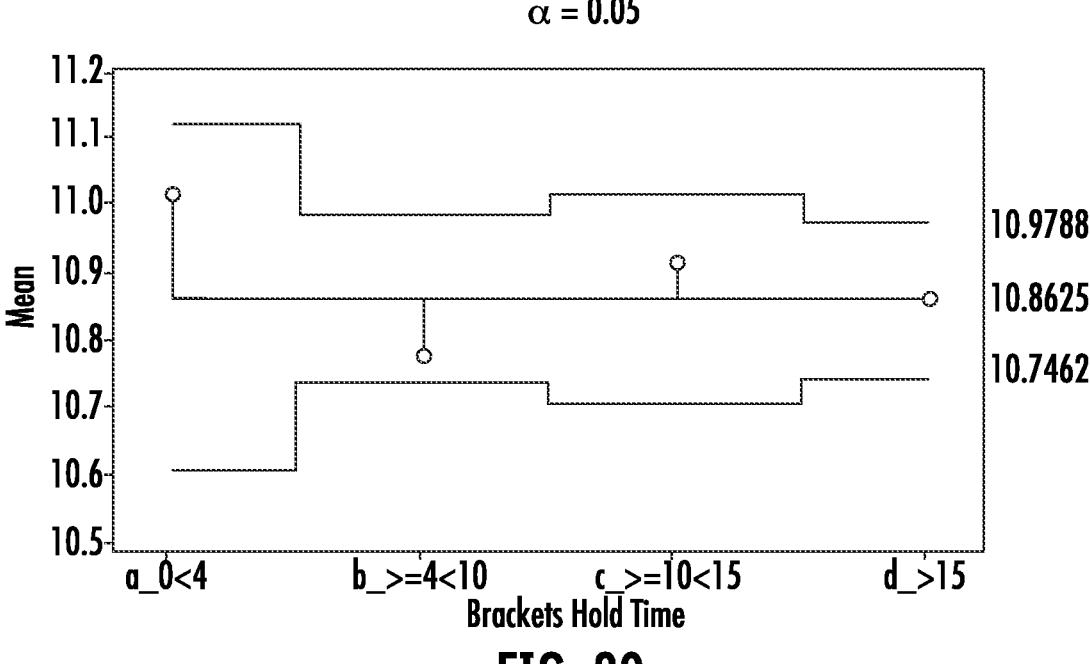
Figure 31:
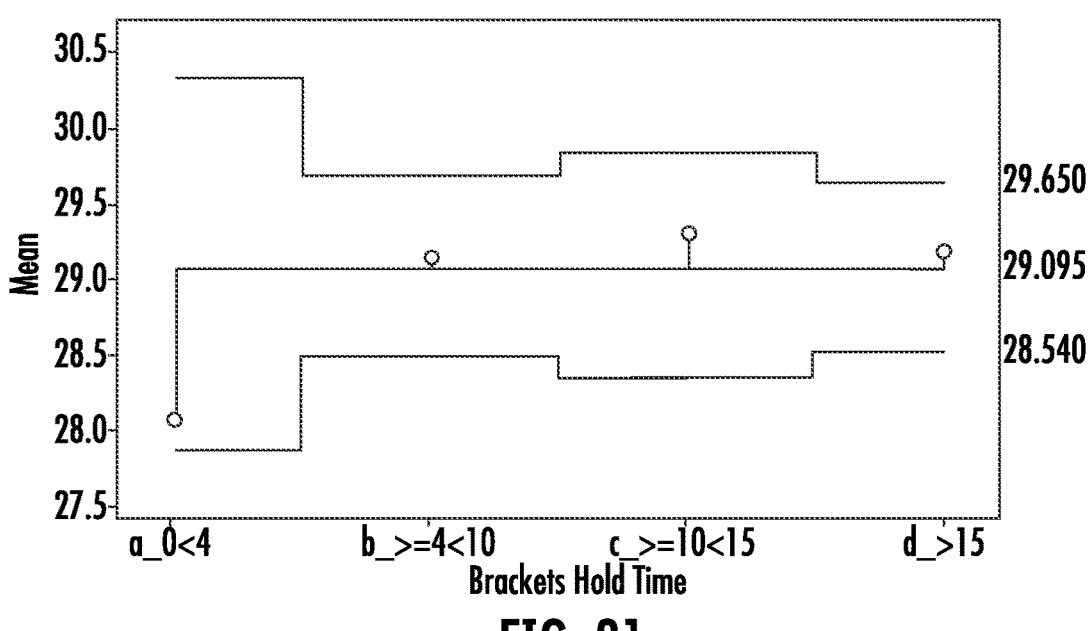

Referring now to FIGS. 29-34, the different interactions and reactions that occur based on processing conditions and notably the post mill hold time are shown with the five actives starting with lauric acid in FIG. 29, followed by myristic acid (FIG. 30), oleic acid (FIG. 31), linoleic acid (FIG. 32), and linolenic acid (FIG. 33). The total fatty acids weight fraction versus the post mill hold time is shown in the line graph of FIG. 34. In all graphs, alpha ($\alpha$)=0.05 and brackets hold time is on the horizontal axis and the mean on the vertical axis. The lauric fatty acid may be statistically higher on average when the hold time is short (FIG. 29). The myristic acid weight fraction is shown in FIG. 30 and it is not evident that the myristic fatty acid is different on average across time.

The oleic acid weight fraction is shown in FIG. 31 and the oleic fatty acid increases directionally and then standardizes over the hold time. The linoleic acid weight fraction versus the post milling hold time is shown in FIG. 32 and it is not evident that the linoleic fatty acid is different on average over the hold time, but the direction pattern is evident on average and then stabilizes.

The linolenic acid weight fraction versus the post milling hold time is shown in FIG. 33 and it is not evident that the linolenic fatty acid is different on the average over the hold time, but the direction pattern is strongly evident on average and then stabilizes. The total fatty acids weight fraction versus the post mill hold time is shown in FIG. 34 and from that and other graphs. The data from preceding graphs and charts display generally that the preprocessing parameters aid in obtaining the enhanced LSESr to obtain the higher percentage of four active free fatty acids (lauric, myristic, oleic and linoleic) when there are specific milling parameters and post-mill aging greater than 15 days.

There are probable interactions as one of the active fatty acids shift. An analysis is helpful about which fatty acid shifts the most and which fatty acids are important to the total free fatty acids and total fatty acids. The data may be analyzed by doing a regression analysis to determine which fatty acids and free fatty acids interact the most to the total free fatty acid in the process with the saw palmetto extract.

The table in FIG. 35 shows a multiple regression for the total free fatty acids versus the fatty acids and showing a model equations report with the four active free fatty acids myristic X1, oleic X2, linoleic X4, linolenic X4, and X5 as bracket hold time in days. The equation uses mass fractions for the individual free fatty acids, and the hold time is days after milling. Lauric acid did not show up as a major contributor that accounts for variance, and thus, it was dropped from the model and in FIG. 35, it is not shown. Myristic, oleic, linoleic and linolenic are illustrated. Lauric acid is considered important to the total free fatty acids, however. It is evident that there are interactions between free fatty acids and the higher order activity on some free fatty acids. The sign of the terms are important since interactions are reducing and others are increasing the total free fatty acid levels. This can be expected as the reactions are occurring during the process.

Referring now to the bar charts in FIG. 36, a multiple regression for total free fatty acids/fatty acids is shown with a model building report. The bar charts show the model building sequence and the incremental impact of x variables and each x regressed on all other terms. The model building sequence on the left displays the order in which the items were added or removed. The bar chart on the upper right shows the incremental impact of oleic acid as compared to linolenic acid as the smallest increase for the R-squared percentage.

The graphs in FIG. 37 show the interactions effect for free fatty acids, where only significant effects are shown. As illustrated, the multiple regressions for the total free fatty acids/fatty acids effect report are shown. The interaction plots show how the total free fatty acids/fatty acids changes if you change the settings of two "X" variables. The main effects plots for total free fatty acids/fatty acids are shown with changes in an "X" variable. The power and significance are highly significant with the low P-value and very high $R^2$ as shown in FIG. 38, which shows a summary report for multiple regressions for the total free fatty acids/fatty acids. The model may be diagnosed with the multiple regression shown in FIG. 39. There is a notable similarity in the short time from harvest to extraction and short hold time post milling.

The multiple regression for the total free fatty acids and model building report are shown. The variables for maximizing total free fatty acids and the reactions and interaction of the fatty acids and free fatty acids are shown as they contribute to total free fatty acid and can be analyzed to determine any maximizing behavior. The five active fatty acids are grouped together as one factor (with free fatty acids as lauric, myristic, oleic, linoleic, and linolenic) and the volatile short chain fatty acids then analyzed. The $R^2$ adjusted is 99.96% and the P-value is about 0.006 on the regression, which are very good values. The interactions and second order reactions with the shorter chains operating towards maximizing the total free acid.

The multiple regression for free fatty acids is shown in FIG. 40. All five factors contribute to the model and do not correlate with one another. A highly significant relationship occurs between the X factors and the percentage of total fatty acids, with a P-value less than about 0.001. With the $R^2$ adjusted at 99.96%, the model of factors account for 99.96% of the variations seen in the saw palmetto extract for total free fatty acids. The summary of the results are shown in the chart and graphs of FIGS. 41-43 and the symmetry of the model is good, so there are no special causes in the data, which is accepted. This data points to the acceptable conclusion that the preprocessing of berries in a specific manner before $CO_2$ extraction has a significant effect on the final LSESr.

The results of the various experiments, such as described relative to the data of FIGS. 4A, 4B, 5 and 6 and the statistical analysis of the various graphs and charts described above, indicate that the key fatty acids as lauric, myristic, oleic, and linoleic free fatty acids are important. It is possible to have lower total fatty acids of greater total and free fatty acids, but the more important aspect is how much of the free fatty acid percentage is contributed by the important four active free fatty acids. The data also reinforces that the preprocessing of the saw palmetto berries is important. A typical hops style extraction can have low free fatty acids in some cases.

The fitted line plot of FIG. 44 shows a relationship between the lauric acid percentage weight/weight and total percentage of free fatty acids. There is variability in the data that would make the difference between about 75% to about 77% insignificant. Directionally, it is known that green berry oil has higher lauric acid versus ripe mature berries. With the mature berries and the aging, the lauric acid is lower in terms of maturity, but the free fatty acids are higher and more consistent around an average. This example applies especially compared to green berry oil.

Another scatter plot of the lauric acid and free fatty acid ratio versus the calculated percentage of oil in berries is shown in the graph of FIG. 45. A goal was to maximize the percentage of free fatty acids and the total oil content for extraction. The lower ratio values are better for saw palmetto oil effectiveness. Similar results are shown in the scatter plot graphs of FIGS. 46, 47, and 48. The hold time in days of FIG. 47 illustrates the lower ratio and tighter consistency with age post-milling and showing an aging of around 25 to 26 days as effective, and thus, greater than 15 days and preferably about 15 to 30 days aging as post-milling. In one aspect, a goal is to age post-milling to 20 days or later for full aging. As shown in FIG. 48, the finished oil for the biomass of around 12.6% to 12.7% is effective.

Referring now to FIGS. 49-52, an analysis of variance for free lauric acid per mill hold time in FIG. 49 is shown with the analysis of variance for free fatty acids for the mill and hold time shown in FIG. 50, and the test for equal variances shown for lauric acid (FIG. 51) and the total free fatty acids (FIG. 52). The mean value of free lauric acid is significantly improved and higher when aging is greater than 15 days and shows a 95% confidence in the data as shown in FIG. 49. The data is statistically and significantly lower when less than 10 days (FIG. 49). The mean value of total free fatty acids is significantly improved and higher when aging is greater than 15 days and showing a 95% confidence (FIG. 50) and significantly and statistically lower when less than 10 days. As shown in FIG. 51, the standard deviation of free lauric acid is improved as a result of the aging process, such as greater than 15 days, and there is a significantly statistical improvement in the standard deviation of the percentage of free fatty acids when aging is greater than 15 days and showing a 95% confidence.

Referring now to FIG. 53, there is illustrated an analysis of variance of free fatty acids per mill and hold for a harvest season and showing the mean by bracketed for post-cryo-milling and aging. The dots in this graph and other similar graphs as described before represent the mean value for these conditions. The first line labeled A is the overall mean value for the data set. The lines labeled B show the 95% confidence lines as function of product variance and sample size. The dots labeled C indicate the mean value is 95% confident as a different higher or lower, and in this specific case, when the post-mill aging is greater than 15 days, the mean value for percentage of free fatty acids is 95% confidently higher than the lower aging times.

Using the same data as above, the test for equal variance (FIG. 54) suggests that the estimate range for the standard deviation across aged time brackets is different and lower than 95% confidence level when the aging is greater than 10 days. Visually, when the brackets in the charge do not overlap, then it is possible to state that it significantly different with an alpha of equal to about 0.05. The practical implication is that the variance of the finished product will be significantly reduced when the percentage of free fatty acids is maximized, thus, creating a high quality extract.

Referring now to FIG. 55, there is illustrated a high level flowchart generally at 500 showing the sequence used to manufacture the supercritical $CO_2$ enhanced LSESr as in Experiments 5 and 6 of FIG. 4A. These examples of the enhanced LSESr have a high ratio of free fatty acids to total fatty acids of greater than about 80.0% and maximizing the four bioactive free fatty acids described above. This better profile is driven by the pre-extraction handling of the ripe berries as described above and the supercritical $CO_2$ extraction parameters as explained in the flowchart of FIG. 55 and relative to the flowchart of FIG. 1. The total fatty acids is less important than the ratio of free versus total fatty acids in order to optimize the contribution of the four major bioactive fatty acids as a percentage of total fatty acids, with the four bioactive fatty acids in this case identified as lauric, myristic, oleic, and linoleic. For hair growth, linolenic free fatty acid also becomes an important contributor.

In this example, the process starts (Block 502) where 19,958 kilogram (kg) of dried saw palmetto (Block 504) was fed through a feed hopper (Block 506). A magnet extracted any magnetic particles or contaminants (Block 508). The product was fed into the hammer mill (Block 510) where liquid nitrogen (Block 512) was applied at about −40° C. to about −30° C., which could possibly range from about −44° C. to about −27° C., a variation of about 10%. The product was aged (Block 514) as noted above, up to about 15 days at least, and preferably at least greater than 15-20 days and up to about 15 to 30 days, or even 15 to 40 days. The temperature may vary during ageing as noted above with a desired mean of about 59° F. to about 78° F. As noted in the data above, aging to greater than 15 days has been found important together with the unique $CO_2$ extraction parameters to optimize the contribution of the four bioactive free fatty acids.

Reference is made to some of the aging parameters described above that were followed. After aging, the aged and milled dried saw palmetto powder was placed into the supercritical $CO_2$ extractor and carbon dioxide used as the supercritical fluid (Block 516) was applied at about 550 bar at 85° C. for $CO_2$ extraction (Block 518). These values can range from about 495 bar to about 605 bar and 77° C. to about 94° C. In this example, based upon the 19958 kg initial amount, the spent marc for the solid waste leftover (Block 520) was obtained at about 16,645 kg.

The first fractionation (Block 522) occurred and the extract was separated at a first stage and the amount as the first separated extract (Block 524) was about 2,426 kg. This first fractionation occurred at about 140 bar at about 77° C. in this example. This pressure could range from about 126 bar to about 350 bar, and the temperature range from about 35° C. to about 85° C. A second fractionation (Block 526) occurred at about 55 bar and at about 25° C. and the second separated extract (Block 528) was about 1,164 kg. The pressure range may be about 30 bar to about 80 bar, and a temperature range may be about 12° C. to about 28° C. The first and second separated extracts may be dewatered and decanted (Block 530), followed by blending to form a final product of about 2,377 kg (Block 532) corresponding to the enhanced LSESr. The process ends (Block 534).

FIG. 56 is a table of comparative data for high and low pressure extraction (250 bar at 70 degrees Centigrade vs. 500 bar at 85 degrees Centigrade) of two lot numbers using the same raw material such as described above. There are differences in concentrations of total free fatty acids, but the proportion of lauric, myristic, oleic, and linoleic to all free fatty acids is the same (81%) between the extraction conditions since the fractionation conditions were similar. This table shows support to the inventive fractionation requirement described above relative to the flowcharts of FIGS. 1 and 55.

This application is related to copending patent applications entitled, "DIETARY SUPPLEMENT COMPOSITION HAVING ENHANCED LSESr AND METHOD OF MAKING," and "COMPOSITION AND METHOD HAVING ENHANCED LSESr TO MAINTAIN AND PROMOTE URINARY AND PROSTATE FUNCTION IN A HUMAN," which are filed on the same date and by the same assignee and inventors, the disclosures which are hereby incorporated by reference.

Many modifications and other embodiments of the invention will come to the mind of one skilled in the art having the benefit of the teachings presented in the foregoing descriptions and the associated drawings. Therefore, it is to be understood that the invention is not to be limited to the specific embodiments disclosed, and that the modifications and embodiments are intended to be included within the scope of the dependent claims.

The invention claimed is:

1. A composition formulated in a therapeutic amount to maintain and promote hair health and growth in a human in need thereof, comprising:

a shelf stable, supercritical $CO_2$ fluid extracted, enhanced lipidosterolic extract of *Serenoa repens* (LSESr), the enhanced LSESr having a ratio of non-esterified free fatty acids to total fatty acids that is about 80.0% to about 82.0% and an enrichment of lauric, myristic, oleic and linoleic acids as non-esterified free fatty acids to total non-esterified free fatty acids that is about 82.0% to about 86.0%, and an enrichment of linoleic and linolenic non-esterified free fatty acids together that is greater than about 3.7%, wherein the enhanced LSESr has a peroxide value of less than 3 meq/kg and a shelf stability of at least about 4 years without added antioxidants and stabilizers.

2. The composition of claim 1 wherein the composition further includes any one or more of zinc, vitamin D, rosemary oil and olive oil.

3. The composition of claim 1 wherein the composition further includes up to about 5.0% of Minoxidil.

4. The composition of claim 1 wherein the enhanced LSESr has an enrichment of lauric, myristic, oleic and linoleic non-esterified free fatty acids to total non-esterified free fatty acids of about 82.0% to about 84.0%.

5. The composition of claim 1 wherein the composition is formulated into an oral dosage form and in a capsule of about 160 mg b.i.d. to about 320 mg, or about minimum 200 mg per dose of enhanced LSESr.

6. The composition of claim 1 wherein the composition includes less than about 0.2 percent w/w of saw palmetto sterols.

7. A composition formulated in a therapeutic amount to maintain and promote hair health and growth in a human in need thereof, comprising:

a shelf stable, supercritical $CO_2$ fluid extracted, enhanced lipidosterolic extract of *Serenoa repens* (LSESr), the enhanced LSESr having a peroxide value of less than 3 meq/kg and a shelf stability of at least about 4 years without added antioxidants and stabilizers, the LSESr comprising, an enrichment of lauric, myristic, oleic and linoleic non-esterified free fatty acids to total non-esterified free fatty acids of about 82.0% to about 84.0%;

a ratio of non-esterified free fatty acids to total fatty acids of about 80.0% to about 82.0%; and an enrichment of linoleic and linolenic non-esterified free fatty acids together that is greater than about 3.7%.

8. The composition of claim 7 wherein the composition further includes any one or more of zinc, vitamin D, rosemary oil and olive oil.

9. The composition of claim 7 wherein the composition further includes up to about 5.0% of Minoxidil.

10. The composition of claim 7 wherein the composition is formulated into an oral dosage form and in a capsule of about 160 mg b.i.d. to about 320 mg, or about minimum 200 mg per dose of enhanced LSESr.

11. The composition of claim 7 wherein the composition includes less than about 0.2 percent w/w of saw palmetto sterols.

12. The composition of claim 7 wherein the composition further includes a dry excipient comprising at least one of silicon dioxide, calcium silicate, calcium phosphate, magnesium oxide, magnesium carbonate, calcium carbonate, rice fiber, and maltodextrin.

13. A method to maintain and promote hair health and growth in a human by administering to the human in need thereof a therapeutic amount of a composition, the composition comprising:

a shelf stable, supercritical $CO_2$ fluid extracted, enhanced lipidosterolic extract of *Serenoa repens* (LSESr), the enhanced LSESr having a ratio of non-esterified free fatty acids to total fatty acids that is about 80.0% to about 82.0% and an enrichment of lauric, myristic, oleic and linoleic acids as non-esterified free fatty acids to total non-esterified free fatty acids that is about 82.0% to about 86.0%, and an enrichment of non-esterified free fatty acids linoleic and linolenic acids together that is greater than about 3.7%, wherein the enhanced LSESr has a peroxide value of less than 3 meq/kg and a shelf stability of at least about 4 years without added antioxidants and stabilizers.

14. The method of claim 13 wherein the composition further includes any one or more of zinc, vitamin D, rosemary oil and olive oil.

15. The method of claim 13 wherein the composition further includes up to about 5.0% of Minoxidil.

16. The method of claim 13 wherein the enhanced LSESr has an enrichment of lauric, myristic, oleic and linoleic non-esterified free fatty acids to total non-esterified free fatty acids of about 82.0% to about 84.0%.

17. The method of claim 13 wherein the composition is formulated into an oral dosage form.

18. The method of claim 17 wherein the composition is formulated into an oral dosage form and in a capsule of about 160 mg b.i.d. to about 320 mg, or about minimum 200 mg per dose of enhanced LSESr.

19. The method of claim 13 wherein the composition includes less than about 0.2 percent w/w of saw palmetto sterols.

20. The method of claim 13 wherein the composition further includes a dry excipient comprising at least one of silicon dioxide, calcium silicate, calcium phosphate, magnesium oxide, magnesium carbonate, calcium carbonate, rice fiber, and maltodextrin.

21. The composition of claim 1 wherein the composition further includes a dry excipient comprising at least one of silicon dioxide, calcium silicate, calcium phosphate, magnesium oxide, magnesium carbonate, calcium carbonate, rice fiber, and maltodextrin.

* * * * *